(12) United States Patent
Tyvoll et al.

(10) Patent No.: US 11,643,743 B2
(45) Date of Patent: May 9, 2023

(54) METHODS AND APPARATUSES FOR FORMING METAL OXIDE NANOSTRUCTURES

(71) Applicant: ALFRED E. MANN INSTITUTE FOR BIOMEDICAL ENGINEERING AT THE UNIVERSITY OF SOUTHERN CALIFORNIA, Los Angeles, CA (US)

(72) Inventors: David Alvin Tyvoll, Los Angeles, CA (US); Bharat Kumar Menon, Los Angeles, CA (US); Nan Chen, Los Angeles, CA (US); Heather Michelle Grandin, Los Angeles, CA (US); Harald Nuhn, Los Angeles, CA (US); Jenna Brynne Lubet, Los Angeles, CA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 125 days.

(21) Appl. No.: 17/274,084

(22) PCT Filed: Sep. 13, 2019

(86) PCT No.: PCT/US2019/051118
§ 371 (c)(1),
(2) Date: Mar. 5, 2021

(87) PCT Pub. No.: WO2020/060874
PCT Pub. Date: Mar. 26, 2020

(65) Prior Publication Data
US 2021/0238764 A1    Aug. 5, 2021

Related U.S. Application Data

(60) Provisional application No. 62/733,203, filed on Sep. 19, 2018.

(51) Int. Cl.
*C25D 11/26* (2006.01)
*A61L 31/02* (2006.01)
(Continued)

(52) U.S. Cl.
CPC ............ *C25D 11/26* (2013.01); *A61L 31/022* (2013.01); *A61L 31/088* (2013.01);
(Continued)

(58) Field of Classification Search
CPC ... C25D 5/02; C25D 11/26; A61F 2/06; A61L 31/022; A61L 31/16; A61L 31/148
See application file for complete search history.

(56) References Cited

U.S. PATENT DOCUMENTS

| 11,230,787 B2 * | 1/2022 | Tyvoll ................... C25D 11/12 |
| 2005/0060021 A1 * | 3/2005 | O'Brien ................ A61L 31/148 205/333 |

(Continued)

OTHER PUBLICATIONS

EPO—International Search Report dated Dec. 10, 2019 from related International Application No. PCT/US2019/051118; 4pgs.
(Continued)

*Primary Examiner* — Dah-Wei D. Yuan
*Assistant Examiner* — Andrew J Bowman
(74) *Attorney, Agent, or Firm* — McDermott Will & Emery LLP

(57) ABSTRACT

Embodiments of methods and apparatuses for forming the metal oxide nanostructure on surfaces are disclosed. In certain embodiments, the nanostructures can be formed on a substrate made of a nickel titanium alloy, resulting in a nanostructure that can include both titanium oxide and nickel oxide. The nanostructure can be formed on the surface(s) of an implantable medical device, such as a stent.

13 Claims, 46 Drawing Sheets

(51) Int. Cl.
*A61L 31/08* (2006.01)
*C25D 11/00* (2006.01)
*B82Y 30/00* (2011.01)
*B82Y 40/00* (2011.01)

(52) U.S. Cl.
CPC ......... *C25D 11/005* (2013.01); *A61L 2400/12* (2013.01); *A61L 2400/18* (2013.01); *A61L 2420/02* (2013.01); *B82Y 30/00* (2013.01); *B82Y 40/00* (2013.01)

(56) References Cited

U.S. PATENT DOCUMENTS

2009/0297581 A1* 12/2009 Atanasoska ............. A61L 31/16
                                                    623/1.46
2015/0322583 A1* 11/2015 Desai .................... A61L 27/306
                                                    205/134

OTHER PUBLICATIONS

EPO—Written Opinion dated Dec. 10, 2019 from related International Application No. PCT/US2019/051118; 6 pgs.

* cited by examiner

METHODS AND APPARATUSES FOR FORMING METAL OXIDE NANOSTRUCTURES

CROSS-REFERENCE TO RELATED APPLICATION

This application is a U.S. National Phase under 35 U.S.C. § 371 of International Application No. PCT/US2019/051118, filed on Sep. 13, 2019, which is a non-provisional of and claims benefit priority under 35 U.S.C. § 119(e) to U.S. Provisional Application No. 62/733,203, entitled "Methods and Apparatuses for Forming Metal Oxide Nanostructures," filed on Sep. 19, 2018, the entire contents of which are incorporated herein by reference.

FIELD

Embodiments of the present application relate to methods and apparatuses for forming metal oxide nanostructures.

BACKGROUND

Surface modifications have been explored to provide beneficial characteristics to a variety of devices. One of the methods that has been explored for preparing such surface modifications is electrochemical anodization. In electrochemical anodization, the surface being modified forms an anode electrode. The anode is generally then placed into electrical contact with at least one cathode through an electrolyte solution. A voltage is then applied across the anode and cathode for a period of time.

SUMMARY

The present application relates to methods and apparatuses for forming metal oxide nanostructures on the surface of substrates. In some examples, the substrates can be titanium or any titanium alloy, such as a nickel titanium alloy. The resulting metal oxide nanostructures may or may not comprise a nanotube layer formed on the surface of a substrate. The nanotube layer may be formed during an anodization process. Embodiments of the methods and apparatuses for forming the nanostructures on surfaces have several features, no single one of which is solely responsible for their desirable attributes.

While the methods and apparatuses for forming metal oxide nanostructures disclosed herein provide numerous advantages over other known metal oxide layers, they may be particularly beneficial when used with implantable medical devices because they may promote healing by enhancing the integration of the medical device with the surrounding biological tissue. An example is the promotion of endothelial cell migration and proliferation and the inhibition of smooth muscle cell migration and proliferation in the cardiovascular and systemic vascular systems. With a medical device such as a stent, for example, some embodiments may promote the growth of a confluent endothelial layer while inhibiting the growth of the neointima, thus reducing restenosis and leading to long-term patency at the site of implantation.

In some embodiments, the method comprises placing an anode and one or more cathode(s) in electrical contact through an electrolyte solution, and applying a voltage across the anode and cathode(s) through the electrolyte solution for a time period. In some embodiments, the time period is between 15 seconds and 30 minutes, and the voltage is between 10 and 60 V. In some embodiments, the time period is longer than 30 minutes.

In some embodiments, the method comprises providing an anode and one or more cathodes, placing the anode and cathode(s) in electrical contact through an electrolyte solution, and applying a voltage across the anode and cathode(s) through the electrolyte solution for a time period. In some embodiments, the time period is between 15 seconds and 30 minutes, and the voltage is between 10 and 60 V. In some embodiments, the time period is longer than 30 minutes.

In some embodiments, the method comprises placing an anode and at least two cathodes in electrical contact through an electrolyte solution, applying a voltage across the anode and each of the at least two cathodes through the electrolyte solution for a time period. In some embodiments, the voltage applied across the anode and each cathode is controlled independently from the voltage(s) applied across the anode and the other cathode(s). In some embodiments, the anode can be generally cylindrical in shape (e.g., a hollow cylinder, a stent) and one of the at least two cathode(s) is positioned inside the generally cylindrical anode (e.g., the cathode can be positioned along a center axis of the cylindrical anode) and one of the at least two cathodes is positioned outside the generally cylindrical anode.

In some embodiments, the method comprises providing an anode and at least two cathodes, placing the anode and at least two cathodes in electrical contact through an electrolyte solution, applying a voltage across the anode and each of the at least two cathodes through the electrolyte solution for a time period. In some embodiments, the voltage applied across the anode and each cathode is controlled independently from the voltage(s) applied across the anode and the other cathode(s). In some embodiments, the anode can be generally cylindrical in shape (e.g., a hollow cylinder, a stent) and one of the at least two cathode(s) is positioned inside the generally cylindrical anode (e.g., the cathode can be positioned along a center axis of the cylindrical anode) and one of the at least two cathodes is positioned outside the generally cylindrical anode.

In some embodiments, the method comprises placing an anode and one or more cathodes in electrical contact through an electrolyte solution, applying a voltage across the anode and the cathode(s) through the electrolyte solution for a time period, wherein the voltage applied across the anode and the cathode(s) is a waveform (e.g., variable potential over time).

In some embodiments, the method comprises providing an anode and one or more cathodes, placing the anode and cathode(s) in electrical contact through an electrolyte solution, applying a voltage across the anode and the cathode(s) through the electrolyte solution for a time period, wherein the voltage applied across the anode and the cathode(s) is a waveform (e.g., variable potential over time).

In some embodiments, the method comprises placing an anode and one or more cathodes in electrical contact through an electrolyte solution, wherein the anode comprises a substrate and one or more guard electrodes, and applying a first voltage across the anode and cathode(s) through the electrolyte solution for a time period. In some embodiments, the anode and guard electrode(s) are not in direct physical contact. In other embodiments, the anode and guard electrode(s) are in direct physical contact.

In some embodiments, the method comprises providing an anode and one or more cathodes, wherein the anode comprises a substrate and one or more guard electrodes, placing the anode and cathode(s) in electrical contact through an electrolyte solution, and applying a first voltage across the anode and cathode(s) through the electrolyte solution for a time period. In some embodiments, the anode and guard electrode(s) are not in direct physical contact. In other embodiments, the anode and guard electrode(s) are in direct physical contact.

In some embodiments, the method comprises placing an anode and one or more cathodes in electrical contact through a first electrolyte solution, applying a first voltage across the anode and cathode(s) through the first electrolyte solution for a first time period, removing at least part of an oxide layer formed on the surface of the anode during the first time period, and applying a second voltage across the anode and cathode(s) through the second electrolyte solution for a second time period. The first and second voltages can be the same or different. The first and second time periods can be the same or different.

In some embodiments, the method comprises providing an anode and one or more cathodes, placing the anode and cathode(s) in electrical contact through a first electrolyte solution, applying a first voltage across the anode and cathode(s) through the first electrolyte solution for a first time period, removing at least part of an oxide layer formed on the surface of the anode during the first time period, and applying a second voltage across the anode and cathode(s) through the second electrolyte solution for a second time period. The first and second voltages can be the same or different. The first and second time periods can be the same or different.

In some embodiments, the method comprises pretreating an anode, placing the pretreated anode in electrical contact with one or more cathodes through an electrolyte solution, and applying a voltage across the pretreated anode and cathode(s) through the electrolyte solution for a time period. The voltage may be constant, or it may comprise a more complex function, such as a ramp, a step function, or a waveform. In some embodiments, the pretreated anode has a nanotextured surface comprising a plurality of nanopits. In some embodiments, the anode can be pretreated by an anodization step followed by removal of the oxide layer created during the anodization step.

In some embodiments, the method comprises placing an anode and one or more cathodes in electrical contact through an electrolyte solution, applying a voltage across the anode and the cathode(s) through the electrolyte solution for a time period, wherein the anode and/or the cathode(s) are moved relative to one another during the time period. In some embodiments, the movement of the anode relative to the cathode(s) is rotational.

In some embodiments, the method comprises providing an anode and one or more cathodes, placing the anode and cathode(s) in electrical contact through an electrolyte solution, applying a voltage across the anode and the cathode(s) through the electrolyte solution for a time period, wherein the anode and/or the cathode(s) are moved relative to one another during the time period. In some embodiments, the movement of the anode relative to the cathode(s) is rotational.

In some embodiments of the methods described herein, the electrolyte solution(s) described herein may or may not be exchanged during or in between periods of anodization. In some embodiments, a first electrolyte solution includes an ethylene glycol-based electrolyte with ammonium fluoride and water. In some embodiments, for example, the first step can be an anodization with a constant voltage $V_1$. This anodization can be run for several minutes, and then the first electrolyte solution is exchanged with a second electrolyte solution comprising an aprotic solvent, a non-fluoride bearing salt, and an oxygen source. In other embodiments, the aprotic solvent is propylene carbonate, the non-fluoride bearing salt is ammonium sulfate, and the oxygen source is N-methyl-morpholine-N-oxide. Simultaneously, or nearly so, the voltage can be ramped down or reduced in a step function to a voltage $V_2$, and the anodization can be continued for a period of time. In some embodiments, another optional step can include the exchange of the propylene carbonate-based electrolyte solution with a salt-free, aprotic solvent. Suitable solvents include those listed above, as well as others capable of dissolving the non-fluoride bearing salt and the oxygen source. Simultaneously, or nearly so, the voltage is reduced to zero. An optional fourth step can include the exchange of the aprotic solvent in the previous step with an aprotic solvent with a higher vapor pressure. These include, but are not limited to, ethyl acetate, ethers such as diethyl ether, tetrahydrofuran, acetonitrile, benzene, toluene, methylene chloride, hexanes, petroleum ether, and the like. In some embodiments, hexanes can be used. In some embodiments, the anode is allowed to soak in the aprotic solvent for a limited period of time, typically between 5-60 minutes. In some embodiments, the anode is allowed to soak in the solvent for less than 5 minutes. The anode is then removed from the solvent and allowed to dry.

In some embodiments of the methods described herein, the voltage(s) applied across the anode and cathode(s) may or may not vary over time, and may or may not include an initial ramp, a terminating ramp, and/or one or more step functions. As an example, at time zero a voltage applied across the anode and cathode(s) can be ramped or stepped up from zero volts to 25 volts, maintained at 25 volts for a duration, and then the voltage can be ramped or stepped down. In some embodiments, the rate of the voltage ramp(s) can be between about 0.04 volts per second and about 2.5 volts per second. In some embodiments, during the terminating ramp or the step function to a second, lower voltage, the electrolyte solution may or may not be changed or modified such that it does not contain a source of fluoride. In some embodiments, during the terminating ramp or the step function to a second, lower voltage, the electrolyte may or may not be changed or modified to comprise an aprotic solvent. Any aprotic solvent may be used, including but not limited to acetonitrile, tetrahydrofuran, formamide, dimethylformamide, acetamide, dimethylsulfoxide, methylsulonylmethane, tetramethylene sulfone, pyrrolidone, N-methylpyrrolidone, ethylene carbonate, and propylene carbonate. For example, propylene carbonate can be used due to a combination of being a liquid at or near room temperature, low vapor pressure, limited toxicity, and its ability to dissolve sufficient amounts of salts. In some embodiments, the exchange of ethylene glycol for an aprotic solvent may reduce surface cracking of the anode upon the termination of the anodization.

In some embodiments of the methods described herein, a source of oxygen other than water is used in the electrolyte solution(s). In the cases of a terminating ramp or the step function to a lower voltage across the anode and cathode(s), water may or may not be replaced in part or in its entirety in the electrolyte solution(s) by an aprotic oxygen source. Single atom sources of oxygen may be used since oxygen sources that already contain an oxygen-oxygen bond such as hydrogen peroxide are more readily oxidized to molecular oxygen. A small amount of hydrogen peroxide (e.g. about 1 wt % or less) may or may not be present, however, as long as its presence does not lead to degradation of the anode. Other single atom sources of oxygen such as the halogen bleaches are not preferred, since the presence of the halogen can lead to degradation of the anode. In some embodiments, the single atom sources of oxygen can be N-alkyl-N-oxides. In other embodiments, the single atom source of oxygen can be N-methyl-morpholine-N-oxide. To increase the rate of the reaction, the anode and/or electrolyte can be exposed to ultrasonic energy. In other embodiments, the single atom source of oxygen may be nitrous oxide. In embodiments where the single atom source of oxygen is nitrous oxide, the nitrous oxide can be bubbled through the electrolyte.

In some embodiments of the methods described herein, a base is added to the electrolyte solution(s) near the end of the anodization period(s). In some embodiments, the addition of a base to the electrolyte solution may reduce the surface cracking of the anode upon the termination of the anodization. Suitable bases include triethanolamine, trialkylamines such as triethylamine, and the like. The base may be added near the end of the anodization period(s), within, for example, about one minute of the end of the anodization period(s), or, for example, within about 30 seconds of the end of the anodization period(s). The amount of base to be added depends upon the basicity of the base, but in general the amount should exceed the molar amount of the fluoride salt present.

In some embodiments of the methods described herein, as an alternative or in addition to the addition of a base to the electrolyte solution(s), molecular sieves may be added to the electrolyte solution(s) near the end of the reaction. The purpose of the addition of the sieves is to sequester water, which can provide another source of protons. Since the electrolyte typically contains ethylene glycol, 3-4 Å molecular sieves can be used. In some embodiments, the electrolyte solution is gently stirred or agitated after addition of the molecular sieves.

In some embodiments of the methods described herein, the method comprises placing an anode and one or more cathodes in electrical contact through an electrolyte solution, and applying a voltage across the anode and the cathode(s) through the electrolyte solution for a time period, wherein the electrolyte solution contains a surface-active species.

In some embodiments of the methods described herein, the method comprises providing an anode and one or more cathodes, placing the anode and cathode(s) in electrical contact through an electrolyte solution, and applying a voltage across the anode and the cathode(s) through the electrolyte solution for a time period, wherein the electrolyte solution contains a surface-active species.

In some embodiments, titanium oxide may be deposited on the anode after the anodization. The anodizations described herein may or may not yield a nanostructured surface. Due to the microscopic features present on, for example, a vascular nitinol stent, and due to a Pilling-Bedworth ratio greater than one for the nanostructured surface, some surface cracks may be present after the anodization. Such cracks are generally undesirable for most applications, since they may lack the thin, integral $TiO_2$ passivating layer which is normally present on a nitinol stent. Methods available to deposit titanium oxides onto nitinol include physical vapor deposition methods and atomic layer deposition ("ALD"). The deposition temperature is sufficiently high such that the nitinol is present in the austenitic, or parent, phase.

In some embodiments of the methods discussed above, the anode or substrate can be an implantable medical device, including but not limited to a stent. The cathode(s) can be platinum, iron, stainless steel, graphite, or any other conductive material.

An apparatus for forming metal oxide nanostructures is also disclosed herein. In some embodiments, the apparatus comprises at least one cathode and is configured to hold an anode (e.g., a stent) such that the at least one cathode and the anode can be placed into electrical contact through an electrolyte solution. The at least one cathode can be made from any suitable material, including but not limited to platinum, iron, stainless steel, or graphite. In some embodiments, the apparatus comprises at least two cathodes, wherein the voltage of each of the at least two cathodes may or may not be controlled independently of one another. In some embodiments with at least two cathodes, at least one of the cathodes is positioned outside of a cylindrical anode (e.g., a stent), and at least one of the cathodes is positioned inside of (e.g., coaxially) the cylindrical anode. In some embodiments, the apparatus further comprises at least one guard electrode. The guard electrode(s) can be made of noble metals, such as platinum or iridium, or reactive metals, such as iron, or metal alloys, such as nitinol or stainless steel. In some embodiments, the apparatus is configured such that the cathode(s) and anode are able to be moved (e.g., rotated or translated) relative to one another.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
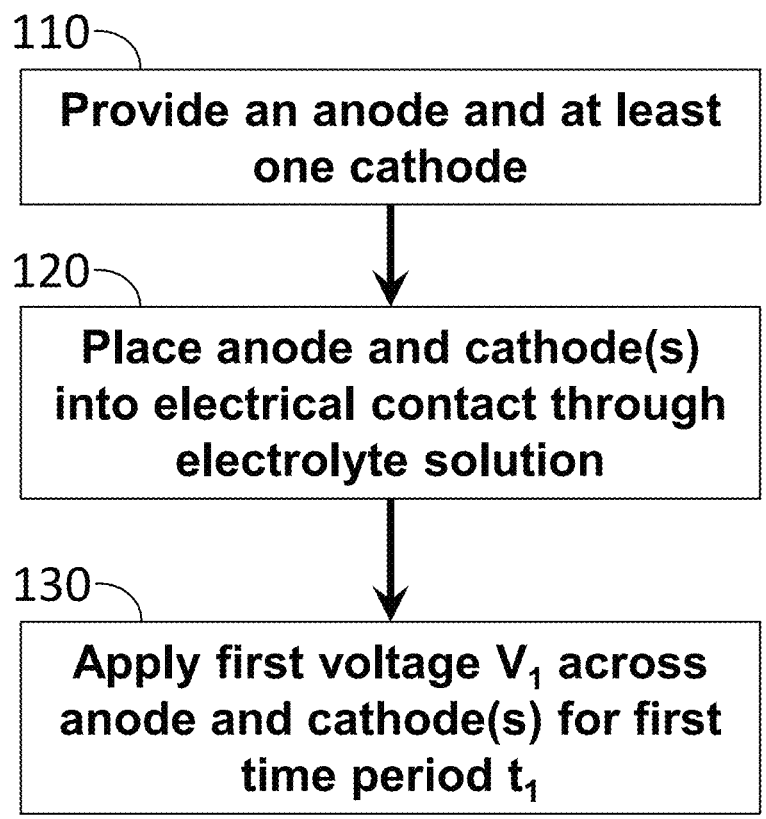
FIG. 1 shows a process flow diagram for one embodiment of a method of forming metal oxide nanostructures.

FIG. 1 shows a process flow diagram for one embodiment of a method of forming metal oxide nanostructures. At block 110, an anode and at least one cathode are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathode(s) can be made from any suitable material, including but not limited to platinum, iron, stainless steel, or graphite. In some embodiments, at least two cathodes are provided, and the at least two cathodes can be positioned such that each cathode is a similar distance from the anode, and preferably in a symmetrical fashion, and the setup can optionally include a reference electrode.

At block 120, the anode and cathode(s) are placed in electrical contact through an electrolyte solution. The electrolyte solution can include an organic solvent, a fluoride-bearing species, and an oxygen source. The oxygen source can be water, or it may be any other single oxygen donor compound, such as methanol. In some embodiments, the electrolyte solution may or may not also optionally contain other additives, such as buffers, surfactants, biocides, salts, and corrosion inhibitors. The electrolyte solution may or may not also optionally contain an acid. Where the electrolyte solution contains an acid, the acid is optionally weak enough or present at a low enough concentration such that it does not interfere with the formation of the nanostructure. In some embodiments, the electrolyte solution does not contain an acid.

The organic solvent can be ethylene glycol. Suitable solvents for use herein include organic solvents, but are not limited to, aliphatic alcohols, aromatic alcohols, diols, glycol ethers, poly(glycol)ethers, lactams, formamides, acetamides, long chain alcohols, ethylene glycol, propylene glycol, diethylene glycols, triethylene glycols, glycerol, dipropylene glycols, glycol butyl ethers, polyethylene glycols, polypropylene glycols, amides, ethers, carboxylic acids, esters, organosulfides, organosulfoxides, sulfones, alcohol derivatives, carbitol, butyl carbitol, cellosolve, ether derivatives, amino alcohols, and ketones. Specific examples of organic solvents include, but are not limited to, a polyhydric alcohol, such as ethylene glycol, diethylene glycol, triethylene glycol, tetraethylene glycol, and polyethylene glycols; a polyhydric alcohol ether, such as ethylene glycol monomethylether, ethylene glycol monoethylether, ethylene glycol monobutylether, diethylene glycol monoethylether, diethylene glycol monobutyl ether, and ethylene glycol monophenyl ether; a nitrogen-containing solvent, such as N-methyl-2-pyrrolidone, a substituted pyrrolidone, and mono-, di-, and tri-ethanolamine; or mixtures thereof. The electrolyte may or may not also include nitrogen-containing ketones, such as 2-pyrrolidone, hydroxyethyl-2-pyrrolidone, 1,3-dimethylimidazolid-2-one, and octyl-pyrrolidone; diols, such as ethanediols, propanediols including 1,2-propanediol, 1,3-propanediol, 2-ethyl-2-hydroxymethyl-1,3-propanediol, and ethylhydroxypropanediol, butanediols including 1,2-butanediol, 1,3-butanediol, and 1,4-butanediol, pentanediols including 1,2-pentanediol, and 1,5-pentanediol, hexanediols including 1,2-hexanediol, 1,6-hexanediol, and 2,5-hexanediol, heptanediols including 1,2-heptanediol, and 1,7-heptanediol, octanediols including 1,2-octanediol and 1,8-octanediol; alcohols, such as C1-C6 alcohols including methanol, ethanol, propanol, butanol, pentanol, and hexanol, including isomers thereof such as 1-propanol and 2-propanol; glycol ethers and thioglycol ethers such as polyalkylene glycols including, but not limited to, propylene glycols such as dipropylene glycol, tripropylene glycol, and tetrapropylene glycol; polymeric glycols such as PEG 200, PEG 300, and PEG 400; thiodiglycol; and mixtures thereof. Additional solvents that can be used include hydantoins and derivatives thereof, dimethyl sulfoxide, methylsulfonylmethane, tetramethylene sulfone, butanetriols such as 1,2,4-butanetriol, acetic acid, and polyalkoxylated triols.

Suitable fluoride-bearing species include ammonium fluoride, ammonium bifluoride, potassium fluoride, sodium fluoride, calcium fluoride, magnesium fluoride, and alkylated ammonium fluorides such as tetrabutylammonium fluoride, among others.

The electrolyte solution can be maintained at a relatively constant temperature. The temperature of the electrolyte solution can be between about 0° and 50° Celsius. In some embodiments, the temperature of the electrolyte solution can be between about 10° and 50° Celsius. In some embodiments, the temperature can be between about 5° and 35° Celsius.

In some embodiments, the electrolyte solution includes about 99.2 vol % organic solvent and about 0.8 vol % water, about 0.20 wt % fluoride-bearing species, and is maintained at about 30° C.

At block 130, a voltage $V_1$ is applied across the anode and cathode(s) through the electrolyte solution for a time period $t_1$. The voltage $V_1$ can be between about 10V and about 60V. In some embodiments, the first voltage $V_1$ is between about 15V and about 30V. In some embodiments, the voltage applied across the anode and cathode is constant for the first time period $t_1$. In other embodiments, the voltage applied across the anode and cathode varies over time throughout the time period $t_1$, as for example when the anodization is run in a galvanostatic mode. The voltage may or may not also include a more complex function, such as a ramp, a step function, or a waveform. In some embodiments, the time period $t_1$ can be between about 1 minute and about 30 minutes. In some embodiments, the time period $t_1$ can be less than about 1 minute. In some embodiments, the time period $t_1$ can be between about 2 minutes and about 25 minutes. In some embodiments, the time period $t_1$ can be between about 3 minutes and about 20 minutes. In some embodiments, the time period $t_1$ can be between about 5 and 15 minutes. In the event that the waveform includes periods of 0 voltage, the time period $t_1$ can be considerably longer. For example, in some embodiments, the time period $t_1$ can be between about 30 minutes and about 60 minutes. In some embodiments, the time period $t_1$ can be more than 60 minutes.

Under suboptimal conditions (e.g., suboptimal voltage $V_1$, suboptimal temperature, suboptimal time period $t_1$, suboptimal electrolyte conditions, or suboptimal positioning of guard electrode(s)), pitting corrosion and/or cracks and/or amorphous material, particulate, or other irregular surface features may or may not be observed. In some embodiments, pitting corrosion and/or cracks and/or amorphous material, particulate, or other irregular surface features are substantially absent.

Figure 2:
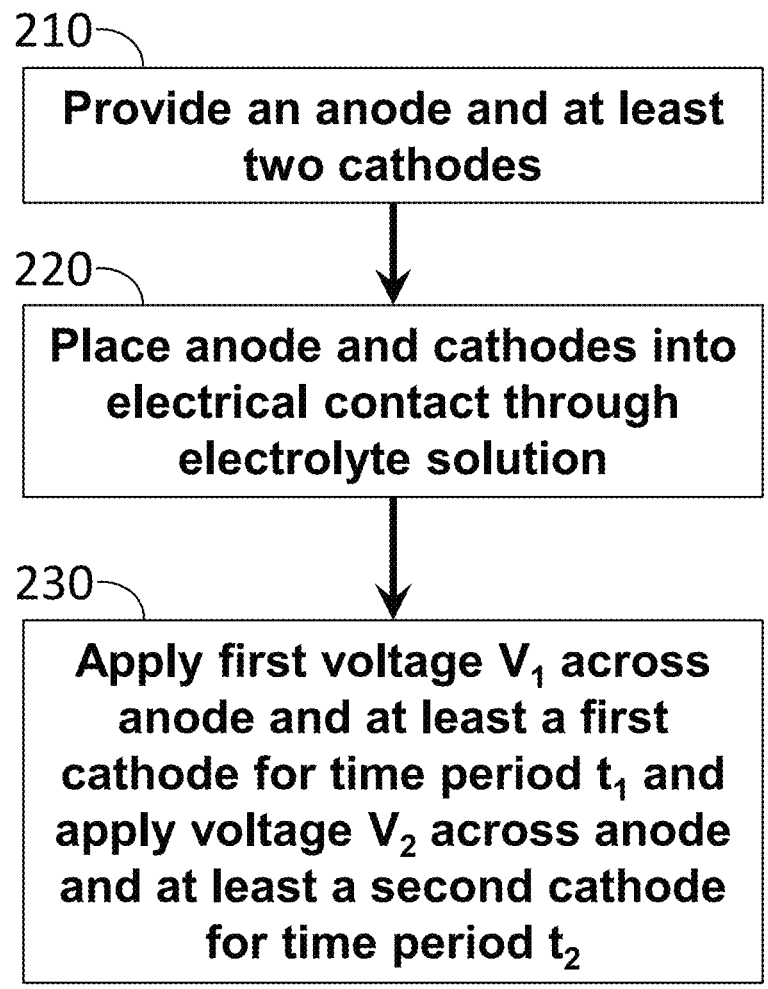
FIG. 2 shows a process flow diagram for another embodiment of a method of forming metal oxide nanostructures.

FIG. 2 shows a process flow diagram for another embodiment of a method of forming metal oxide nanostructures. At block 210, an anode and at least two cathodes are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathodes can be made from any suitable material, including but not limited to platinum, iron, stainless steel, or graphite. In some embodiments in which the anode is generally cylindrical (e.g., a stent), one cathode can be positioned inside the anode (e.g., coaxially), and at least one cathode can be positioned outside the anode. In some embodiments, the cathodes positioned outside the anode can be positioned such that each cathode is a similar distance from the anode, and preferably in a symmetrical fashion.

At block 220, the anode and cathodes are placed in electrical contact through an electrolyte solution. The electrolyte solution can include an organic solvent, a fluoride-bearing species, and an oxygen source. In some embodiments, the organic solvent can be ethylene glycol. In some embodiments, the fluoride-bearing species can be ammonium fluoride. The oxygen source can be water, or it may be any other single oxygen donor compound, such as methanol. In some embodiments, the electrolyte solution does not include an acid. In some embodiments, the electrolyte solution includes about 99.2 vol % organic solvent and 0.8 vol % water, and about 0.20 wt % fluoride-bearing species. The electrolyte solution can be maintained at a relatively constant temperature. The temperature of the electrolyte solution can be between about 0° and 50° Celsius. The temperature of the electrolyte solution can be between about 10° and 50° Celsius. In some embodiments, the temperature of the electrolyte solution is about 30° C.

At block 230, a first voltage $V_1$ is applied across the anode and at least a first cathode through the electrolyte solution for a first time period $t_1$, and a second voltage $V_2$ is applied across the anode and at least a second cathode through the electrolyte solution for a second time period $t_2$. The voltages $V_1$ and $V_2$ may or may not be controlled independently of one another. The voltages $V_1$ and $V_2$ can be the same or different. The voltages $V_1$ and $V_2$ can be between about 10V and about 60V. In some embodiments, the voltages $V_1$ and $V_2$ are about 25V. In some embodiments, the voltages $V_1$ and $V_2$ are constant for the time periods $t_1$ and $t_2$. In other embodiments, the voltages $V_1$ and $V_2$ can vary over time throughout the time periods $t_1$ and $t_2$, as for example when the anodization is run in a galvanostatic mode. The voltages may or may not also include more complex functions, such as ramps, step functions, or waveforms.

The time periods $t_1$ and $t_2$ can be the same or different from one another. The time periods $t_1$ and $t_2$ can occur simultaneously, or at different times. In some embodiments, the time periods $t_1$ and $t_2$ can be between about 1 minute and about 30 minutes. In some embodiments, the time periods $t_1$ through $t_2$ can be less than about 1 minute. In some embodiments, the time periods $t_1$ and $t_2$ can be between about 2 minutes and about 25 minutes. In some embodiments, the time periods $t_1$ and $t_2$ can be between about 3 minutes and about 20 minutes. In some embodiments, the time periods $t_1$ and $t_2$ can be between about 5 and about 15 minutes. In the event that the waveform(s) includes periods of 0 voltage, the time periods $t_1$ and $t_2$ can be considerably longer. For example, in some embodiments, the time periods $t_1$ and $t_2$ can be between about 30 minutes and about 60 minutes. In some embodiments, the time periods $t_1$ and $t_2$ can be more than 60 minutes.

Under suboptimal conditions (e.g., suboptimal voltage $V_1$ or $V_2$, suboptimal temperature, suboptimal electrolyte conditions, or suboptimal first or second time period $t_1$ or $t_2$), pitting corrosion and/or cracks and/or amorphous material, particulate, or other irregular surface features may or may not be observed. In some embodiments, pitting corrosion and/or cracks and/or amorphous material, particulate, or other irregular surface features are substantially absent.

Figure 3:
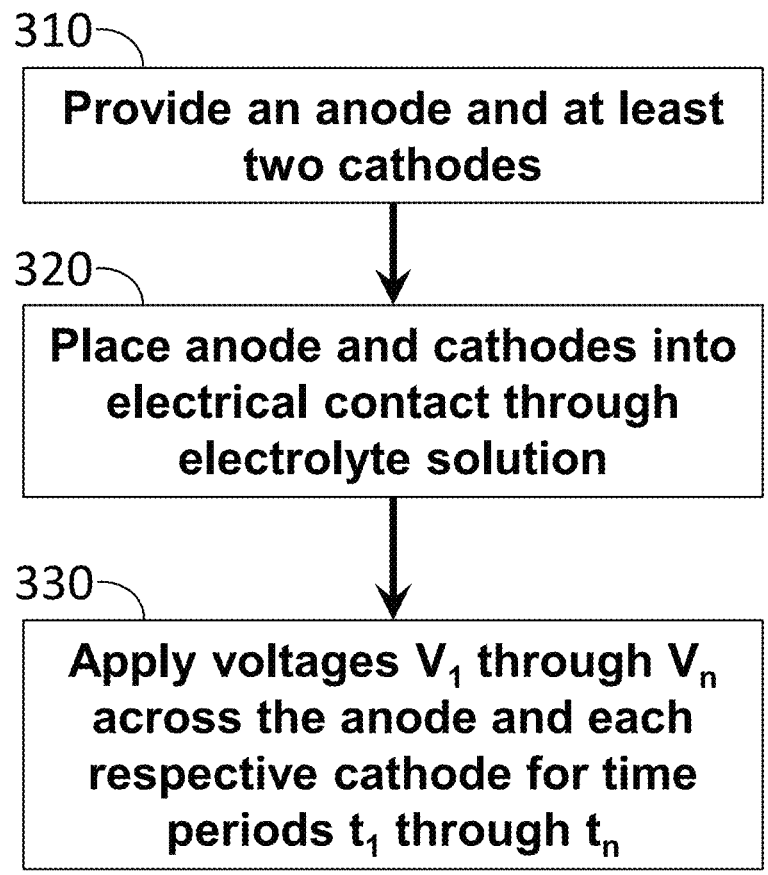
FIG. 3 shows a process flow diagram for another embodiment of a method of forming metal oxide nanostructures.
Figure 15:
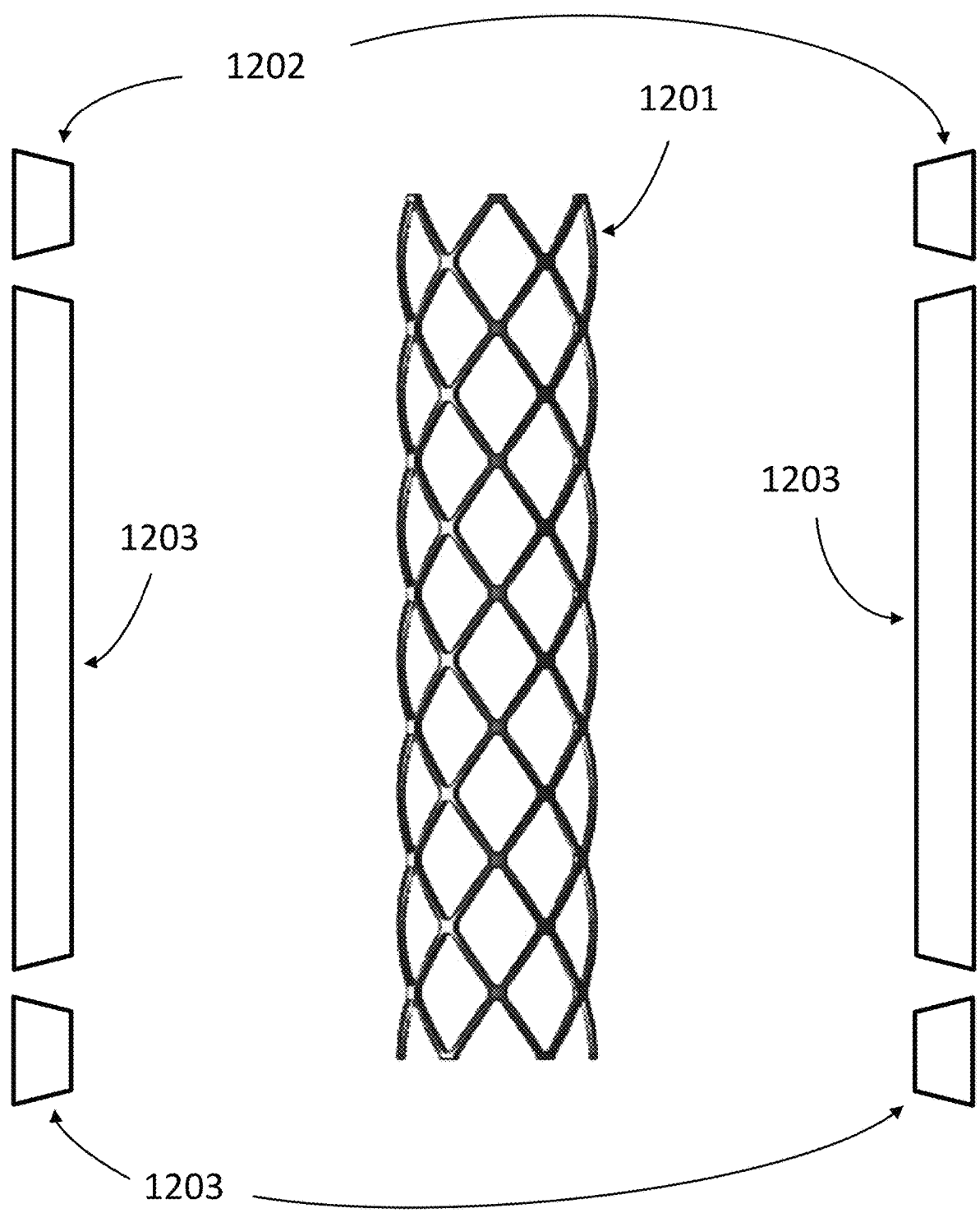
FIG. 15 shows a schematic representation of one embodiment of an arrangement of cathodes and an anode.
Figure 16:
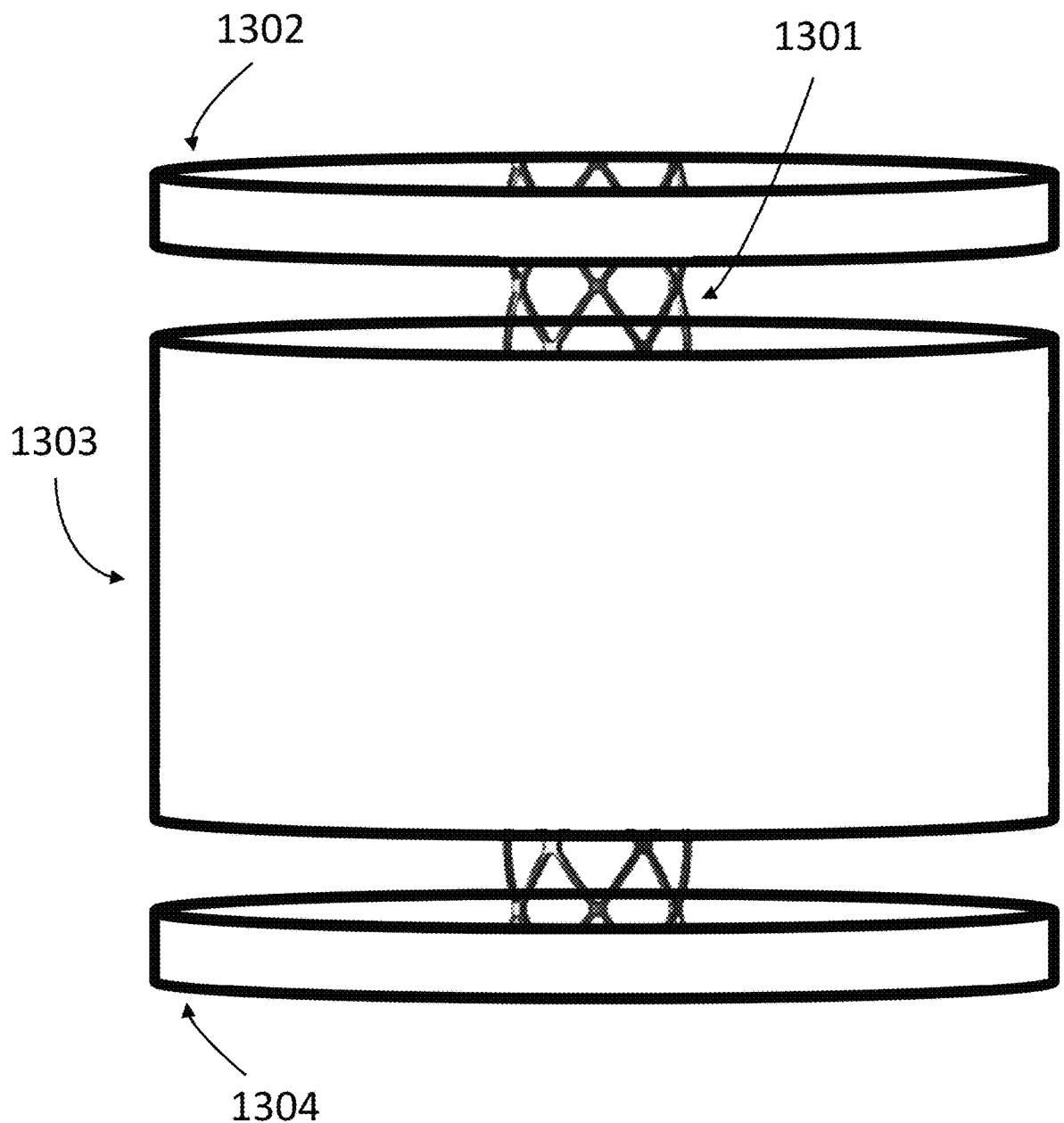
FIG. 16 shows a schematic representation of one embodiment of an arrangement of cathodes and an anode.

FIG. 3 shows a process flow diagram for another embodiment of a method of forming metal oxide nanostructures. At block 310, an anode and at least two cathodes are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathodes can be made from any suitable material, including but not limited to platinum, iron, stainless steel, or graphite. In some embodiments in which the anode is generally cylindrical (e.g., a stent), one cathode can be positioned inside the anode (e.g., coaxially), and at least one cathode can be positioned outside the anode. In some embodiments, cathodes positioned outside the anode can be positioned such that each cathode is a similar distance from the anode, and preferably in a symmetrical fashion. In some embodiments, cathodes can be segmented along the long axis of the anode as shown in FIGS. 15-16.

In some embodiments with a cathode positioned inside the anode, an insulating mesh tubing can be used to prevent inadvertent short-circuiting between the electrodes. For example, nylon mesh tubing of 4-9 mm diameter (BeadFX, Toronto, ON, Canada) can be placed generally coaxially between the cylindrical anode and the inner cathode. If the diameter of the anode is smaller than 4 mm, the mesh tubing can be stretched so that its diameter is significantly reduced (e.g., the 4 mm mesh can be stretched so that its diameter is reduced to about 1 mm).

In embodiments where the anode is a stent or other complex shape, it may be difficult to keep the rate of the anodization the same at different locations. This can be due to inhomogeneities in the electric field, as well as chemical inhomogeneities in the electrolyte. In embodiments where the anode is generally cylindrical (e.g., a stent), different reaction rates can be seen between the inside surface (e.g., luminal) and outside surfaces (e.g., abluminal) of the cylindrical anode. Placing a cathode inside the cylindrical anode may or may not reduce the difference in reaction rates between the inside and outside surfaces of the cylindrical anode. Different reaction rates can also be seen between the ends (e.g., top and bottom) of the stent and the middle of the stent. For example, the thickness of the resulting metal oxide nanostructures can vary by a factor of two or more between the ends and the middle (e.g., 1000 nm versus 500 nm). Placing a segmented cathode(s) along the long axis of the anode may or may not reduce the difference in reaction rates between the ends of the stent and the middle of the stent. In some embodiments, cathodes can be segmented along the long axis of the anode as shown in FIGS. 15-16.

At block 320, the anode and cathodes are placed in electrical contact through an electrolyte solution. The electrolyte solution can include an organic solvent, a fluoride-bearing species, and an oxygen source. In some embodiments, the organic solvent can be ethylene glycol. In some embodiments, the fluoride-bearing species can be ammonium fluoride. The oxygen source can be water, or it may be any other single oxygen donor compound, such as methanol. In some embodiments, the electrolyte solution does not include an acid. In some embodiments, the electrolyte solution includes about 99.2 vol % organic solvent and 0.8 vol % water, and about 0.20 wt % fluoride-bearing species. The electrolyte solution can be maintained at a relatively constant temperature. The temperature of the electrolyte solution can be between about 10° and 50° Celsius. In some embodiments, the temperature of the electrolyte solution is about 30° C.

At block 330, voltages $V_1$ through $V_n$ (where n equals the number of cathodes) are applied across the anode and each cathode through the electrolyte solution for time periods $t_1$ through $t_n$. The voltages $V_1$ through $V_n$ for each cathode may or may not be controlled independently of the voltages for the other cathodes. The voltages $V_1$ through $V_n$ can be between about 10V and about 60V. In some embodiments, the voltages $V_1$ through $V_n$ are about 25V. In some embodiments, the voltages $V_1$ through $V_1$ through $V_n$ are constant for the times period $t_1$ through $t_n$. In other embodiments, the voltages $V_1$ through $V_n$ can vary over time throughout the time period $t_n$, as for example when the anodization is run in a galvanostatic mode. The voltages may or may not also include more complex functions, such as ramps, step functions, or waveforms.

The time periods $t_1$ through $t_n$ can be the same or different from one another. The time periods $t_1$ through $t_n$ can occur simultaneously or at different times. In some embodiments, the time periods $t_1$ through $t_n$ can be between about 1 minute and about 30 minutes. In some embodiments, the time periods $t_1$ through $t_n$ can be less than about 1 minute. In some embodiments, the time periods $t_1$ through $t_n$ can be between about 2 minutes and about 25 minutes. In some embodiments, the time periods $t_1$ through $t_n$ can be between about 3 minutes and about 20 minutes. In some embodiments, the time periods $t_1$ through $t_n$ can be between about 5 and about 15 minutes. Where the waveform(s) includes periods of 0 voltage, the time periods $t_1$ through $t_n$ can be considerably longer. For example, in some embodiments, the time periods $t_1$ through $t_n$ can be between about 30 minutes and about 60 minutes. In some embodiments, the time periods $t_1$ through $t_n$ can be more than 60 minutes.

For embodiments with a cathode positioned inside a generally cylindrical anode, the rate of the anodization depends on many factors, including the diameter of the cylindrical anode, the diameter of the cathode(s), the electrolyte composition, the degree to which the electrolyte is circulated, the openness (e.g., porosity) of the anode, the geometry of the outer cathode(s), and others.

For example, if the cylindrical anode (e.g., a stent) has a large diameter and a relatively high degree of openness, the electric field can penetrate inside the anode to a significant degree and the rate of reaction on the inside is similar to that on the outside. In such cases, the effect of a cathode positioned inside the anode on the rate of anodization on the inside surface (e.g., luminal) relative to the outside surface (e.g., abluminal) of the anode may be minimal. On the other hand, for example, if the generally cylindrical anode (e.g., a stent) has a small diameter and a relatively low degree of openness, the electric field created during the anodization can be significantly diminished inside the cylindrical anode compared to outside the cylindrical anode, and thus the rate of reaction on the inside surface (e.g., luminal) of the cylindrical anode will be reduced relative to the rate of anodization on the outside surface (e.g., abluminal) of the cylindrical anode. In such cases, the presence of an additional cathode positioned inside the anode can reduce the difference in anodization rates between the inside and outside surfaces of the anode, resulting in a more homogenous metal oxide nanostructure on the inside and outside surfaces of the anode.

In some embodiments, applying a different voltage to the inner cathode and outer cathode(s) may reduce the difference in the anodization rates between the inside (e.g., luminal) and outside (e.g., abluminal) surfaces of the anode. The rate of anodization on each surface (e.g., luminal, abluminal, radial) of a fenestrated cylindrical anode (e.g., a stent) is a function of the effective voltage at each such surface. The effective voltage at each surface is a function of the exposed surface area of the cathodes and anode, the distance between and geometry of the surfaces of the cathode(s) and anode, the ability of the electrolyte to exchange efficiently with the bulk, and other factors, all of which can result in a voltage drop between the cathode(s) and the anode. The voltage drop between cathodes positioned outside a cylindrical anode and the outer surface (e.g., abluminal) of the cylindrical anode may or may not be different than the voltage drop between the cathode positioned inside the cylindrical anode and the inside surface (e.g., luminal) of the anode, resulting in different anodization rates at the inside and outside surfaces of the anode.

For example, if the outer cathode(s) is 25 mm away from a 2 mm diameter cylindrical anode (e.g., 2 mm diameter stent), the voltage at the outer cathode can be set to 25V, with an approximately 2V voltage drop between the outer cathode(s) and the outer surface (e.g., abluminal) of the anode, resulting in an effective voltage at the anode being approximately 23V. A cathode positioned inside the 2 mm cylindrical anode, for example a 0.25 mm diameter platinum wire, will have a distance between the surface of the inside cathode to the inner surface (e.g., luminal) of the cylindrical anode of only approximately 0.875 mm, which will result in only a negligible voltage drop between the surface of inside cathode and inside surface of the cylindrical anode, so the voltage at the inside cathode can be set to 23V while still maintaining an effective voltage at the inside surface (e.g., luminal) of the cylindrical anode at 23V. Similar results (e.g., similar anodization rates at the inside and outside surfaces of a cylindrical anode) may or may not be achieved by independently controlling the time periods of the different cathodes. For example, if the reaction rate on the outside of the stent is greater than that on the inside, the time of the applied voltage to the outside cathode(s) can be less than the time of the applied voltage to the inner cathode.

The diameter of an inner cathode must be less than the diameter of its corresponding cylindrical anode (e.g., stent). The diameters of stents can be as small as about 2-3 mm or less. To allow for sufficient electrolyte diffusion and exchange, and potential short circuiting, the diameter of the inner cathode can be less than 2-3 mm, for example about 1 mm or less. Depending on the diameter of the inner cathode and the porosity of the cylindrical anode, the surface area of the inner cathode relative to the surface area of the inside surface (e.g., luminal) of the stent can vary greatly. Thus the choice of the diameter of the inner cathode should be chosen with care, balancing the ability to circulate the electrolyte with the bulk. In extreme cases, the presence of an inner cathode may not be able to rectify the different reaction rates between the inside and outside of the stent.

Figure 18:
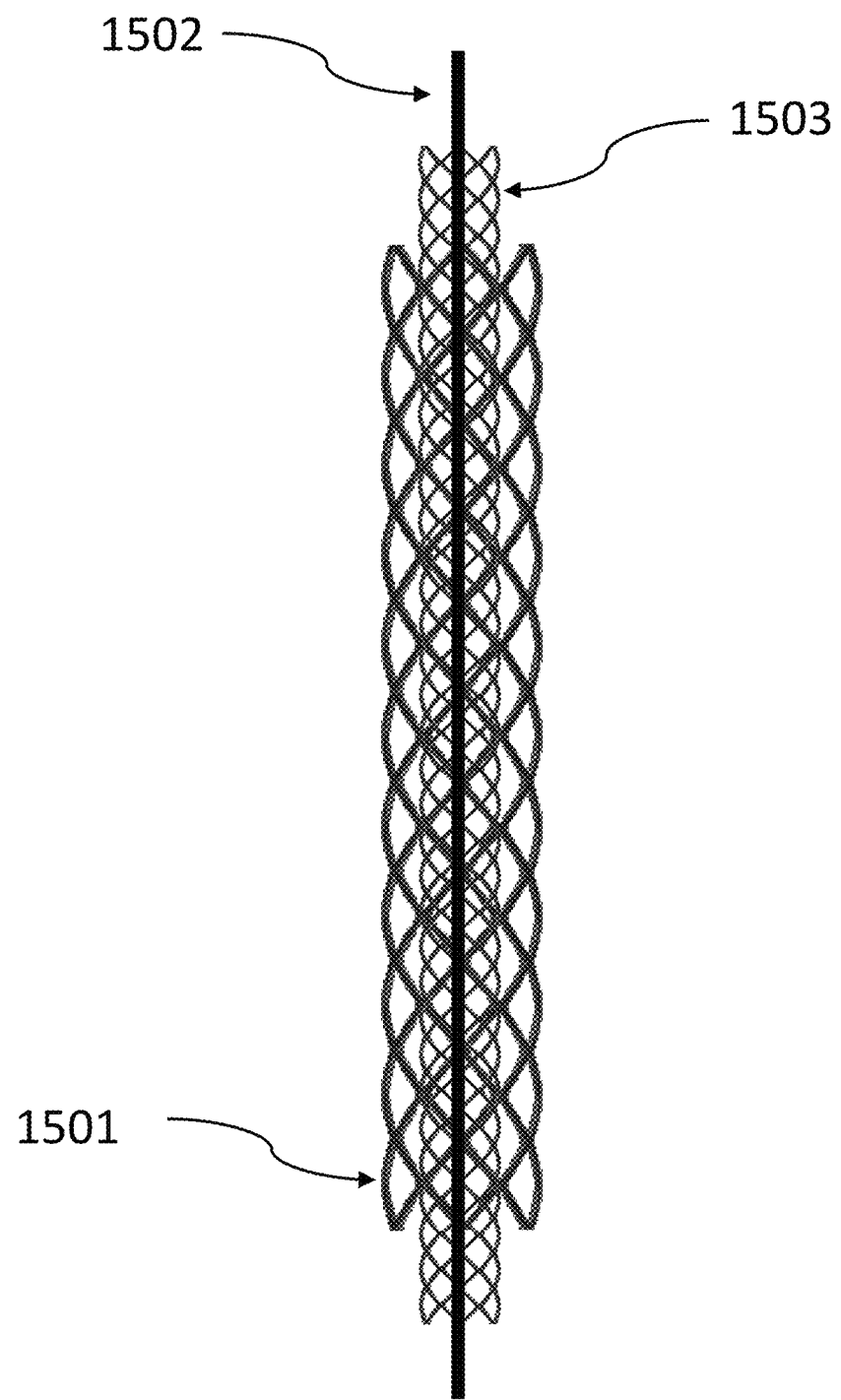
FIG. 18 shows a schematic representation of one embodiment of an arrangement of an anode, an insulating layer, and a cathode positioned inside the anode.

These methods may also be used in converse, that is, to deliberately create different structures (e.g., different thickness of the resulting metal nanostructures) on the inside versus outside surfaces of the anode. The inner cathode may or may not also be partially insulated, in order to mitigate the field pinning inherent at the ends of the stent. An embodiment of a partially insulated inner cathode is shown in FIG. 18.

Under suboptimal conditions (e.g., suboptimal voltage $V_1$ through $V_n$, suboptimal temperature, suboptimal electrolyte conditions, or suboptimal first or second time period $t_1$ through $t_n$), pitting corrosion and/or cracks and/or amorphous material, particulate, or other irregular surface features may or may not be observed. In some embodiments, pitting corrosion and/or cracks and/or amorphous material, particulate, or other irregular surface features are substantially absent.

Figure 4:
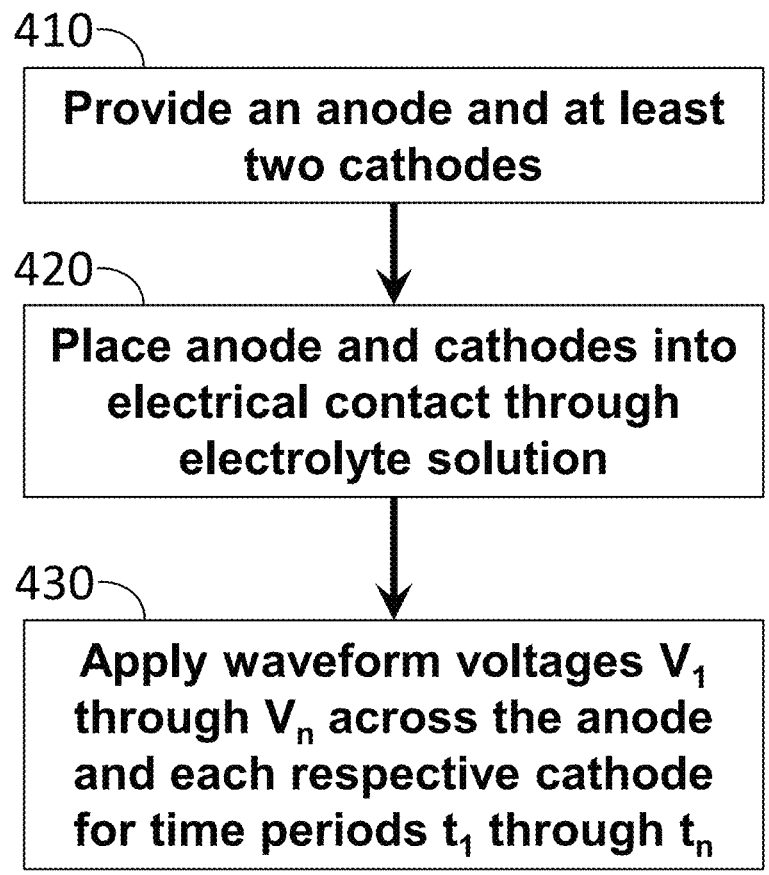
FIG. 4 shows a process flow diagram for another embodiment of a method of forming metal oxide nanostructures.

FIG. 4 shows a process flow diagram for another embodiment of a method of forming metal oxide nanostructures. At block 410, an anode and at least two cathodes are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathodes can be made from any suitable material, including but not limited to platinum, iron, stainless steel, or graphite. In some embodiments in which the anode is generally cylindrical (e.g., a stent), one cathode can be positioned inside the anode (e.g., coaxially), and at least one cathode can be positioned outside the anode. In some embodiments, the cathodes can be positioned such that each cathode is a similar distance from the anode, and preferably in a symmetrical fashion.

At block 420, the anode and cathodes are placed in electrical contact through an electrolyte solution. The electrolyte solution can include an organic solvent, a fluoride-bearing species, and an oxygen source. In some embodiments, the organic solvent can be ethylene glycol. In some embodiments, the fluoride-bearing species can be ammonium fluoride. The oxygen source can be water, or it may be any other single oxygen donor compound, such as methanol. In some embodiments, the electrolyte solution does not include an acid. In some embodiments, the electrolyte solution includes about 99.2 vol % organic solvent and 0.8 vol % water, and about 0.20 wt % fluoride-bearing species. The electrolyte solution can be maintained at a relatively constant temperature. The temperature of the electrolyte solution can be between about 10° and 50° Celsius. In some embodiments, the temperature of the electrolyte solution is about 30° C.

At block 430, waveform voltages $V_1$ through $V_n$ (where n equals the number of cathodes) are applied across the anode and each cathode through the electrolyte solution for time periods $t_1$ through $t_n$. The waveform voltages $V_1$ through $V_n$ for each cathode may or may not be controlled independently of the waveform voltages for the other cathodes. The waveform voltages $V_1$ through $V_n$ can be applied across each of the cathodes simultaneously, at overlapping times, or at discrete times throughout time periods $t_1$ through $t_n$.

In some embodiments, each of the voltages $V_1$ through $V_n$ can be modulated with time between a period of positive voltage and a period of zero voltage. In some embodiments, the voltage can be between about 10V and about 100V. In some embodiments, the voltage can be between about 15V and about 35V, or about 25V.

In some embodiments the voltages $V_1$ through V, can be applied across each of the respective cathodes to the anode for time periods $t_1$ through $t_n$. In some embodiments, the time periods $t_1$ through $t_n$ can be between about 2 minutes and about 60 minutes. In some embodiments, the time periods $t_1$ through $t_n$ can be less than about 2 minutes. In some embodiments, the time periods $t_1$ through $t_n$ can be between about 5 minutes and 30 minutes. In some embodiments, the time periods $t_1$ through $t_n$ can be between about 10 minutes and 20 minutes. In other embodiments, the time periods $t_1$ through $t_n$ can be considerably longer. For example, in some embodiments, the time periods $t_1$ through $t_n$ can be between about 60 minutes and about 120 minutes. In some embodiments, the time periods $t_1$ through $t_n$ can be more than 120 minutes.

In some embodiments the positive voltage can be applied for a time period of between about 100 ms and about 900 seconds. In some embodiments the positive voltage can be applied for a time period of between about 500 ms and about 300 seconds. In some embodiments, the positive voltage can be applied for a time period of between about 1 second and about 120 seconds. The voltages $V_1$ through $V_n$ can be returned to zero volts after the voltages are applied. In some embodiments, the voltages $V_1$ through $V_n$ can be returned to zero volts for a time period of between about 100 ms and about 900 seconds. In some embodiments the voltages $V_1$ through $V_n$ can be returned to zero volts for a time period of between about 500 ms and about 500 seconds. In some embodiments the voltages $V_1$ through $V_n$ can be returned to zero volts for a time period of between about 1 second and about 300 seconds. This cycling of voltages $V_1$ through $V_n$ between non-zero voltage and zero voltage can be repeated for each respective cathode throughout time periods $t_1$ through $t_n$. The voltages $V_1$ through $V_n$ can vary with each cycle, or can remain constant with each cycle. The amount of time each of the voltages $V_1$ through $V_n$ are applied across the anode and cathodes can be constant, or can vary with each cycle. The amount of time each of the voltages $V_1$ through $V_n$ are returned to zero volts for can be constant, or can vary with each cycle.

In some embodiments, each of the voltages $V_1$ through $V_n$ applied across the anode and cathodes can be modulated with time between a period of positive voltage, followed by a period of zero voltage, followed by a period of negative voltage. In some embodiments the positive voltage can be between about 10 and about 100 volts. In some embodiments the positive voltage can be between about 15 and about 35 volts. In some embodiments the positive voltage can be about 25 volts. In some embodiments the positive voltage can be applied for a time period of between about 100 ms and about 900 seconds. In some embodiments the positive voltage can be applied for a time period of between about 500 ms and about 300 seconds. In some embodiments, the positive voltage can be applied for a time period of between about 1 second and about 120 seconds. In some embodiments the negative voltage can be between about −0.1 and about −25 volts. In some embodiments the negative voltage can be between about −1 and about −10 volts. In some embodiments the negative voltage can be between about −2 and about −4 volts. In some embodiments the negative voltage can be applied for a time period of between about 1 μs and about 100 ms. In some embodiments the negative voltage can be applied for a time period of between about 10 μs and about 10 ms. In some embodiments the voltage can be set to zero following the positive voltage time period for a time period of between about 100 ms and about 900 seconds. In some embodiments the voltage can be set to zero for a time period of between about 500 ms and about 500 seconds. In some embodiments, the voltage can be set to zero for a time period of between about 1 second and about 300 seconds. In some embodiments, following the period of negative voltage, the voltages $V_1$ through $V_n$ can repeat the cycle of a period of positive voltage, followed by a period of zero voltage, followed by a period of negative voltage.

In some embodiments, each of the voltages $V_1$ through $V_n$ applied across the anode and cathodes can be modulated with time between a period of positive voltage, followed by a period of negative voltage, followed by a period of zero voltage. In some embodiments the positive voltage can be between about 10 and about 100 volts. In some embodiments the positive voltage can be between about 15 and about 35 volts, and in some embodiments the positive voltage can be about 25 volts. In some embodiments the positive voltage can be applied for a time period of between about 100 ms and about 900 seconds. In some embodiments the positive voltage can be applied for a time period of between about 500 ms and about 300 seconds. In some embodiments, the positive voltage can be applied for a time period of between about 1 second and about 120 seconds. In some embodiments the negative voltage can be between about −0.1 and about −25 volts. In some embodiments the negative voltage can be between about −1 and about −10 volts. In some embodiments the negative voltage can be between about −2 and about −4 volts. In some embodiments the negative voltage can be applied for a time period of between 1 μs and 100 ms. In some embodiments the negative voltage can be applied for a time period of between 10 μs and 10 ms. In some embodiments the voltage can be set to zero following the negative voltage time period for a time period of between about 100 ms and about 900 seconds. In some embodiments the voltage can be set to zero for a time period of between about 500 ms and about 500 seconds. In some embodiments, the voltage can be set to zero for a time period of between about 1 second and about 300 seconds. In some embodiments, following this period of zero voltage, the voltages $V_1$ through $V_n$ can repeat the cycle of a period of positive voltage, followed by a period of negative voltage, followed by a period of zero voltage.

In some embodiments, each of the voltages $V_1$ through $V_n$ applied across the anode and cathodes can be modulated with time between a period of positive voltage, followed by a period of zero voltage, followed by a period of negative voltage, followed by a period of zero voltage. In some embodiments the positive voltage can be between about 10 and about 100 volts. In some embodiments the positive voltage can be between about 15 and about 35 volts, and in some embodiments the positive voltage can be about 25 volts. In some embodiments the positive voltage can be applied for a time period of between about 100 ms and about 900 seconds. In some embodiments the positive voltage can be applied for a time period of between 500 ms and 300 seconds. In some embodiments, the positive voltage can be applied for a time period of between about 1 second and about 120 seconds. In some embodiments the voltage can be set to zero following the negative voltage time period for a time period of between about 100 ms and about 900 seconds. In some embodiments the voltage can be set to zero for a time period of between about 500 ms and about 500 seconds. In some embodiments, the voltage can be set to zero for a time period of between about 1 second and 300 seconds. In some embodiments the negative voltage following the period of zero voltage can be between about −0.1 and about −25 volts. In some embodiments the negative voltage can be between about −1 and about −10 volts. In some embodiments the negative voltage can be between about −2 and about −4 volts. In some embodiments the negative voltage can be applied for a time period of between about 1 µs and about 100 ms. In some embodiments the negative voltage can be applied for a time period of between about 10 µs and about 10 ms. In some embodiments the voltage can be set to zero following the negative voltage time period for a time period of between about 100 ms and about 900 seconds. In some embodiments the voltage can be set to zero for a time period of between about 500 ms and about 500 seconds. In some embodiments, the voltage can be set to zero for a time period of between about 1 second and about 300 seconds. In some embodiments, following this second period of zero voltage, the voltages $V_1$ through $V_n$ can repeat the cycle of a period of positive voltage, followed by a period of zero voltage, followed by a period of negative voltage, followed by a period of zero voltage.

The time periods $t_1$ through $t_n$ can be the same or different from one another. The time periods $t_1$ through $t_n$ can occur simultaneously or at different times. In some embodiments, the time periods $t_1$ through $t_n$ can be between about 2 minutes and about 60 minutes. In some embodiments, the time periods $t_1$ through $t_n$ can be less than about 2 minutes. In some embodiments, the time periods $t_1$ through $t_n$ can be between about 5 minutes and 30 minutes. In some embodiments, the time periods $t_1$ through $t_n$ can be between about 10 minutes and 20 minutes. In other embodiments, the time periods $t_1$ through to can be considerably longer. For example, in some embodiments, particularly if the respective voltage $V_1$ through $V_n$ applied across the anode and cathodes for a given time period is variable (e.g., a waveform), the time periods $t_1$ through $t_n$ can be between about 60 minutes and about 120 minutes. In some embodiments, the time periods $t_1$ through $t_n$ can be more than 120 minutes.

In embodiments where the anode is a cylinder with no openings (e.g., solid tube), there is minimal crosstalk between the electrode voltage on the outside of the cylinder and the electric field on the inside of the cylinder. Contrary to solid tubes, stents may have a high degree of openness (e.g. 70-80%, or more), and the electric field on the outside of the stent may penetrate significantly to the inside of the stent, giving rise to some crosstalk. Controlling or configuring for such crosstalk may be significant in the presence of multiple complex waveforms.

Under suboptimal conditions (e.g., suboptimal voltage $V_1$ through $V_n$, suboptimal temperature, suboptimal electrolyte conditions, or suboptimal first or second time period $t_1$ through $t_n$), pitting corrosion and/or cracks and/or amorphous material, particulate, or other irregular surface features may or may not be observed. In some embodiments, pitting corrosion and/or cracks and/or amorphous material, particulate, or other irregular surface features are substantially absent.

Figure 5:
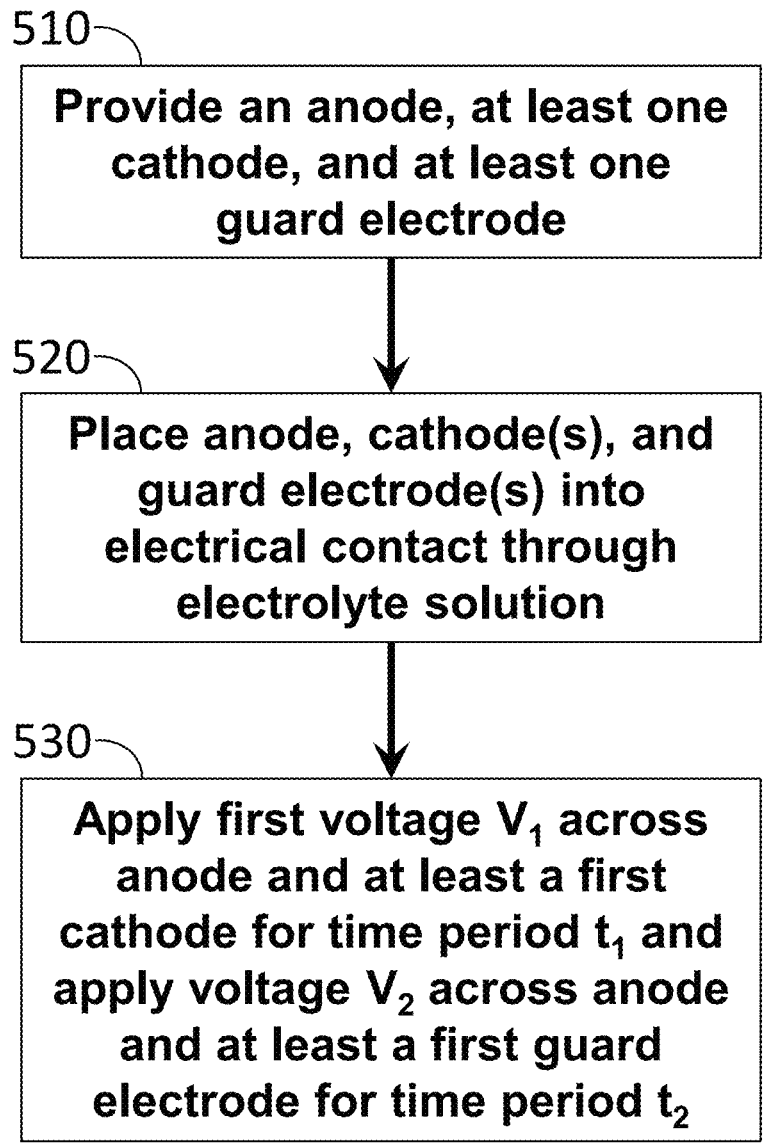
FIG. 5 shows a process flow diagram for another embodiment of a method of forming metal oxide nanostructures.

FIG. 5 shows a process flow diagram for another embodiment of a method of forming metal oxide nanostructures. At block 510, an anode, at least one cathode, and at least one guard electrode are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathode(s) can be made from any suitable material, including but not limited to platinum, iron, stainless steel, or graphite. If more than one cathode is used, the cathodes can be positioned such that each cathode is a similar distance from the anode, and preferably in a symmetrical fashion, and the setup can optionally include a reference electrode.

In some embodiments, the guard electrode(s) can be made of noble metals, such as platinum or iridium, or reactive metals, such as iron, or metal alloys, such as nitinol or stainless steel. In some embodiments, the guard electrodes can be simple wires, rings, meshes, coils, tubes, or stent-like. In some embodiments, the guard electrode(s) are not in direct physical contact with the anode, and are positioned such that they reduce non-uniformity in the electric field around the anode during anodization. In some embodiments, the guard electrode(s) are positioned less than 2 mm from the anode. In some embodiments, the guard electrode(s) are positioned less than about 1 mm or less than about 0.5 mm from the anode.

In some embodiments, the guard electrode(s) are in direct physical contact with the anode. In embodiments where the guard electrode(s) are in direct physical contact with the anode and the anode is symmetrical (e.g., a stent), the guard electrodes should be positioned so as to exhibit the same symmetry as the anode. For example, if there is a guard electrode contacting the proximal end of a symmetrical anode, a guard electrode should also be present at the distal end of the symmetrical anode. In some embodiments where the anode is a bifurcated stent (e.g., a Y-shaped stent), a guard electrode can be placed near or in contact with each of the three ends of the bifurcated stent.

In some embodiments, the guard electrodes can be simple wires, rings, meshes, coils, tubes, or stent-like. In some embodiments, the guard electrode(s) can be electronically controlled in a dependent way, such that they experience the same voltage relative to the cathode as the anode. In other embodiments, the guard electrode(s) may or may not be controlled independently, such that they experience a different voltage relative to the voltage across the cathode and the anode. In some embodiments, the guard electrode(s) may or may not also experience a voltage across the cathode that varies with time.

At block 520, the anode, cathode(s), and guard electrode(s) are placed in electrical contact through an electrolyte solution. The electrolyte solution can include an organic solvent, a fluoride-bearing species, and an oxygen source. In some embodiments, the organic solvent can be ethylene glycol. In some embodiments, the fluoride-bearing species can be ammonium fluoride. The oxygen source can be water, or it may be any other single oxygen donor compound, such as methanol. In some embodiments, the electrolyte does not include an acid. In some embodiments, the electrolyte solution includes about 99.2 vol % organic solvent and about 0.8 vol % water, and about 0.20 wt % fluoride-bearing species. The electrolyte solution can be maintained at a relatively constant temperature. The temperature of the electrolyte solution can be between about 10° and 50° Celsius. In some embodiments, the temperature of the first electrolyte solution is about 30° C.

At block 530, a voltage $V_1$ is applied across the anode and cathode(s) through the electrolyte solution for a time period $t_1$, and a voltage $V_2$ is applied across the guard electrode(s) and cathode(s). The voltages $V_1$ and $V_2$ can be between about 10V and about 60V. In some embodiments, the voltages $V_1$ and $V_2$ are the same. In other embodiments, the voltages $V_1$ and $V_2$ are different. In some embodiments, the voltages $V_1$ and $V_2$ are about 25V. In some embodiments, the voltages $V_1$ and $V_2$ are constant for the time period $t_1$. In some embodiments, the voltages $V_1$ and $V_2$ vary over time throughout the time period $t_1$, as for example when the anodization is run in a galvanostatic mode. The voltages may or may not also include more complex functions, such as ramps, step functions, or waveforms.

The time period $t_1$ can be between about 1 minute and about 30 minutes. In some embodiments, the time period $t_1$ is less than about 2 minutes. In some embodiments, the time period $t_1$ is between about 2 minutes and about 25 minutes. In some embodiments, the time period $t_1$ is between about 3 minutes and about 20 minutes. In some embodiments, the time period $t_1$ is between about 5 and 15 minutes. Where the waveform includes periods of 0 voltage, the time period $t_1$ can be considerably longer. For example, in some embodiments, the time period $t_1$ can be between about 30 minutes and about 60 minutes. In some embodiments, the time period $t_1$ can be more than 60 minutes. The time period applied for which the voltage $V_2$ is applied across the guard electrode(s) and cathode(s) may or may not be different than $t_1$.

Under suboptimal conditions (e.g., suboptimal voltages $V_1$ or $V_2$, suboptimal temperature, suboptimal electrolyte conditions, or suboptimal time period $t_1$), pitting corrosion and/or cracks and/or amorphous material, particulate, or other irregular surface features may or may not be observed. In some embodiments, pitting corrosion and/or cracks and/or amorphous material, particulate, or other irregular surface features are substantially absent.

Figure 6:
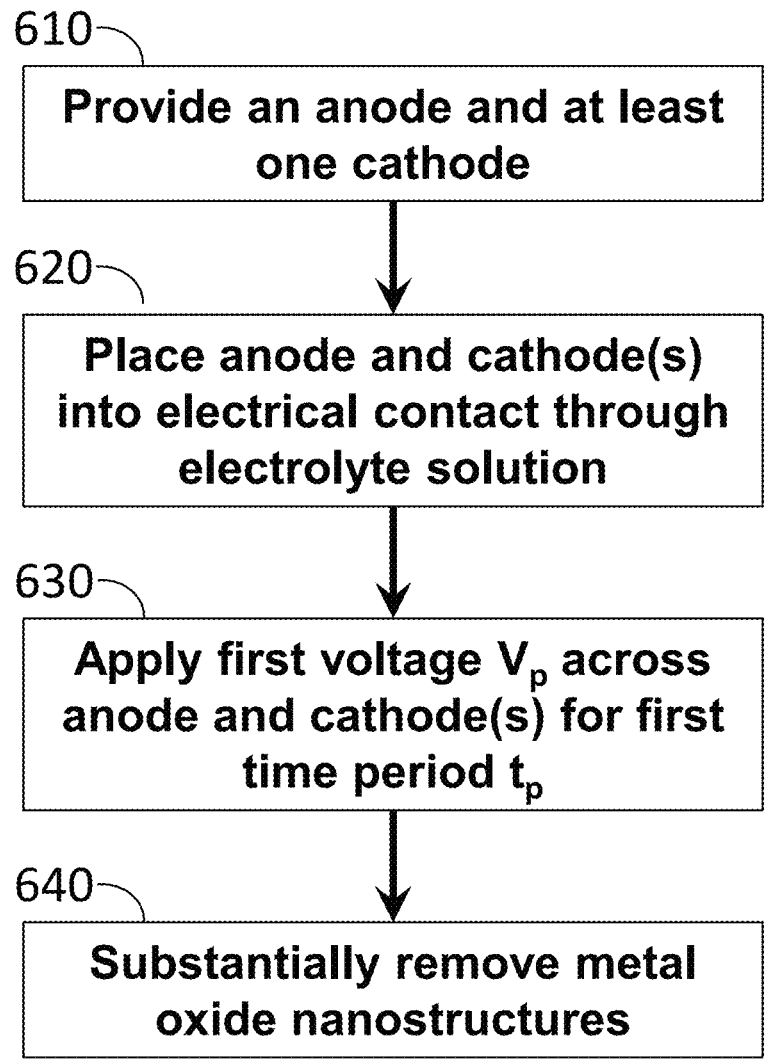
FIG. 6 shows a process flow diagram for another embodiment of a method of forming metal oxide nanostructures.
Figure 7:
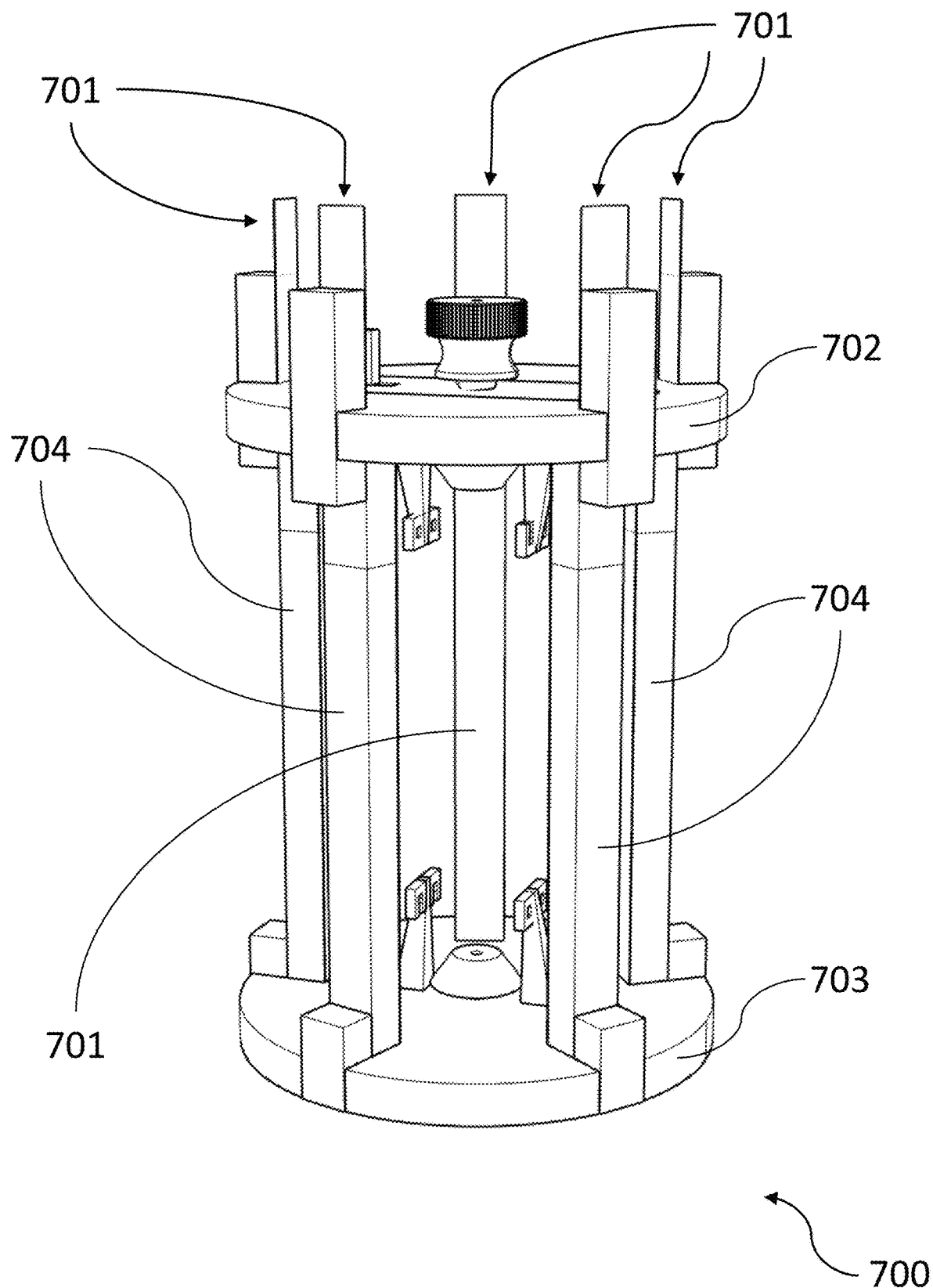
FIG. 7 shows a schematic representation of a partial side and top profile view of one embodiment of an apparatus for forming metal oxide nanostructures.
Figure 8:
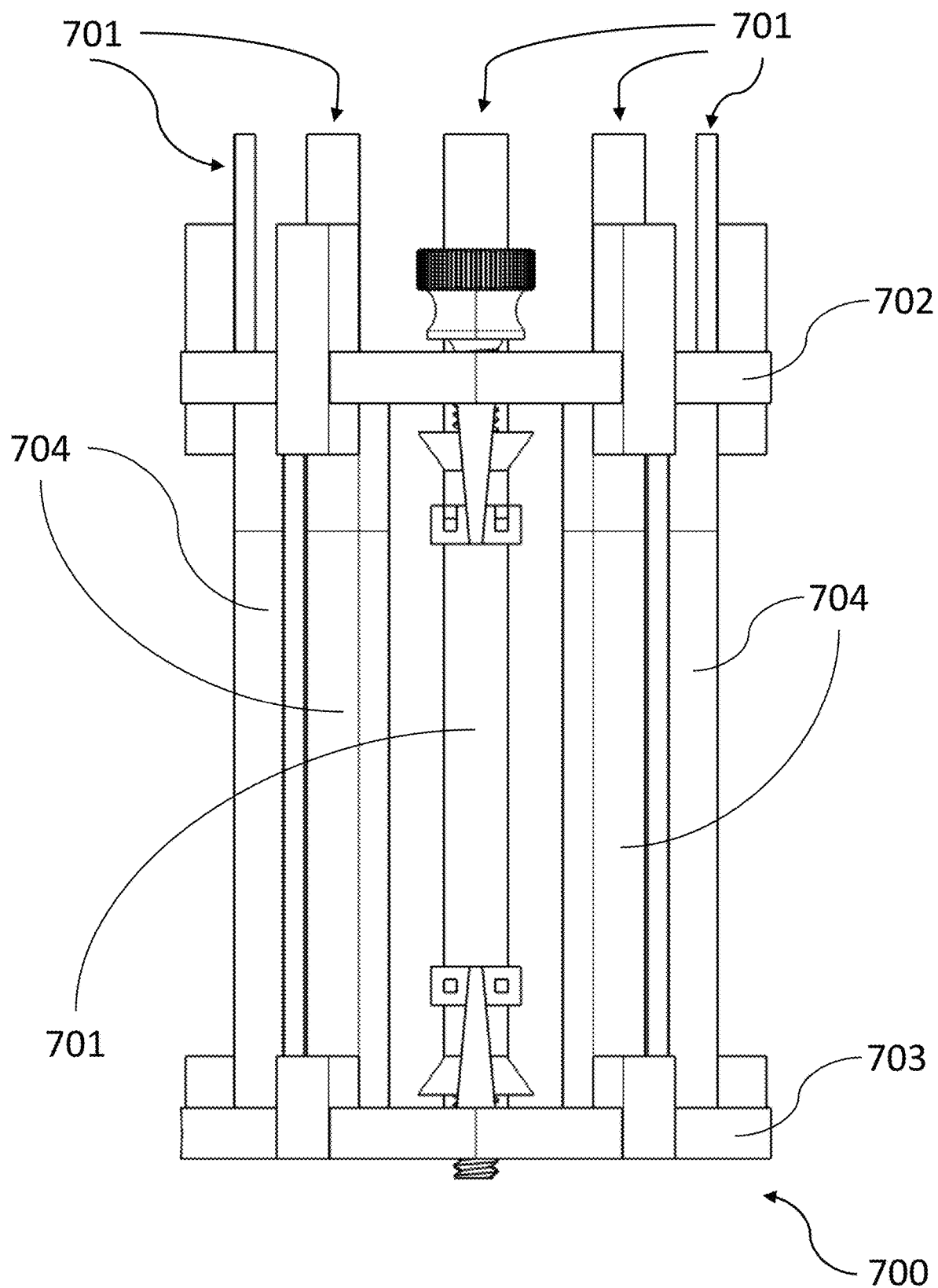
FIG. 8 shows a schematic representation of a side view of the embodiment of the apparatus of FIG. 7.
Figure 9:
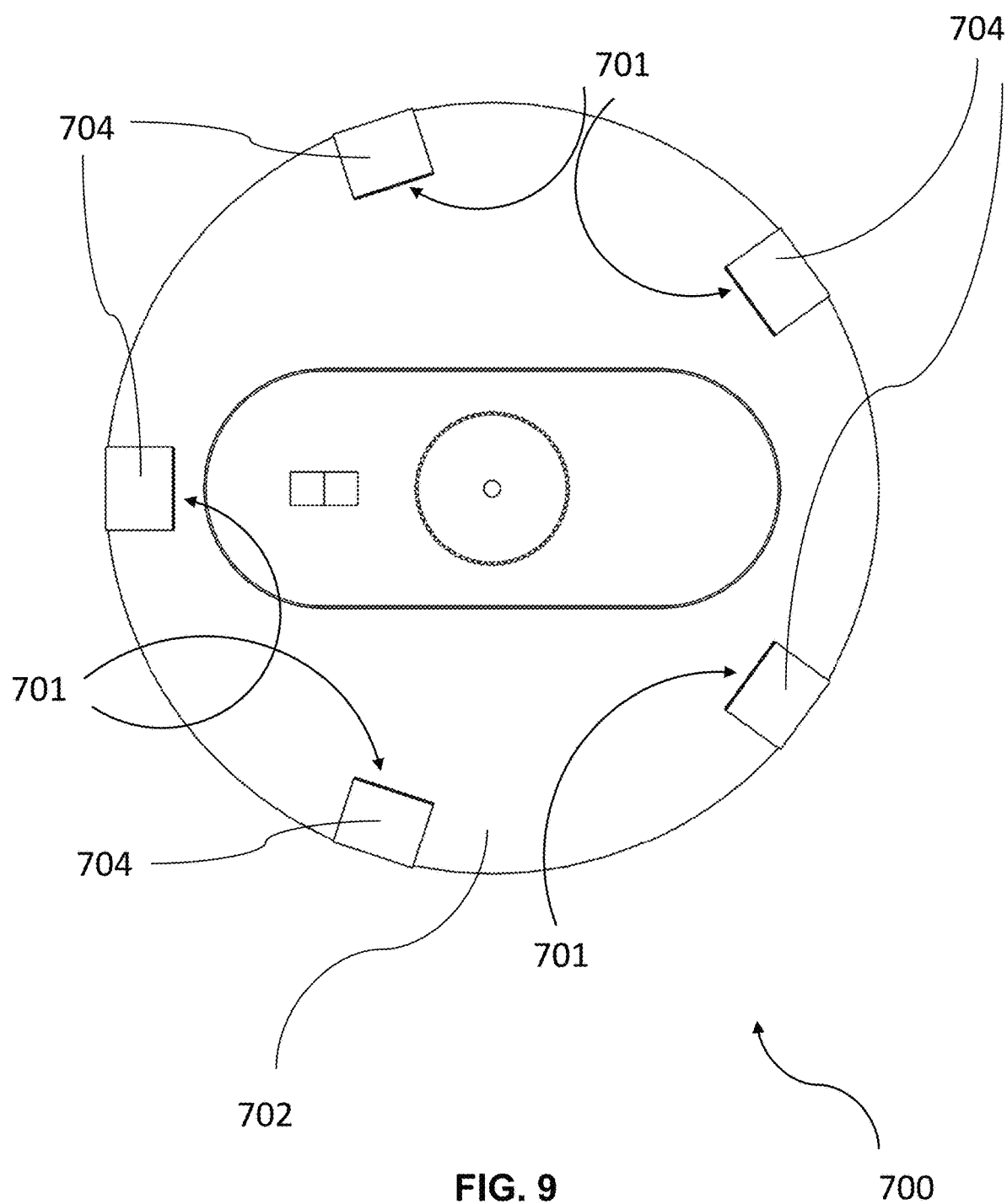
FIG. 9 shows a schematic representation of a top view of the embodiment of the apparatus of FIG. 7.

In some embodiments of the methods shown in FIGS. 1-5 and described herein, the methods may or may not further include pretreating the anode to create a nanotextured surface prior to the anode and cathode being placed in electrical contact. FIG. 6 shows a process flow diagram for pretreating the anode.

At block 610, an anode and at least one cathode are optionally provided. In some embodiments, the anode can be an alloy of nickel and titanium. In certain embodiments, the anode can be an alloy of nickel and titanium, with a ratio of nickel to titanium of approximately 1:1. In some embodiments, the anode can be an implantable medical device, including but not limited to a stent. The cathode(s) can be made from any suitable material, including but not limited to platinum, iron, stainless steel, or graphite. In some embodiments, at least two cathodes are used, and the at least two cathodes can be positioned such that each cathode is a similar distance from the anode, and preferably in a symmetrical fashion, and the setup can optionally include a reference electrode.

At block 620, the anode and cathode(s) are placed in electrical contact through an electrolyte solution. The electrolyte solution can include an organic solvent, a fluoride-bearing species, and an oxygen source. The oxygen source can be water, or it may be any other single oxygen donor compound, such as methanol. In some embodiments, the electrolyte solution may or may not also optionally contain other additives, such as buffers, surfactants, biocides, salts, and corrosion inhibitors. The electrolyte solution may or may not also optionally contain an acid, so long as the acid is weak enough or present at a low enough concentration such that it does not interfere with the formation of the nanostructure. In some embodiments, the electrolyte solution does not contain an acid.

The organic solvent can be ethylene glycol. Suitable solvents for use herein include organic solvents, but are not limited to, aliphatic alcohols, aromatic alcohols, diols, glycol ethers, poly(glycol)ethers, lactams, formamides, acetamides, long chain alcohols, ethylene glycol, propylene glycol, diethylene glycols, triethylene glycols, glycerol, dipropylene glycols, glycol butyl ethers, polyethylene glycols, polypropylene glycols, amides, ethers, carboxylic acids, esters, organosulfides, organosulfoxides, sulfones, alcohol derivatives, carbitol, butyl carbitol, cellosolve, ether derivatives, amino alcohols, and ketones. Specific examples of organic solvents include, but are not limited to, a polyhydric alcohol, such as ethylene glycol, diethylene glycol, triethylene glycol, tetraethylene glycol, and polyethylene glycols; a polyhydric alcohol ether, such as ethylene glycol monomethylether, ethylene glycol monoethylether, ethylene glycol monobutylether, diethylene glycol monoethylether, diethylene glycol monobutyl ether, and ethylene glycol monophenyl ether; a nitrogen-containing solvent, such as N-methyl-2-pyrrolidone, a substituted pyrrolidone, and mono-, di-, and tri-ethanolamine; or mixtures thereof. The electrolyte may or may not also include nitrogen-containing ketones, such as 2-pyrrolidone, hydroxyethyl-2-pyrrolidone, 1,3-dimethylimidazolid-2-one, and octyl-pyrrolidone; diols, such as ethanediols, propanediols including 1,2-propanediol, 1,3-propanediol, 2-ethyl-2-hydroxymethyl-1,3-propanediol, and ethylhydroxypropanediol, butanediols including 1,2-butanediol, 1,3-butanediol, and 1,4-butanediol, pentanediols including 1,2-pentanediol, and 1,5-pentanediol, hexanediols including 1,2-hexanediol, 1,6-hexanediol, and 2,5-hexanediol, heptanediols including 1,2-heptanediol, and 1,7-heptanediol, octanediols including 1,2-octanediol and 1,8-octanediol; alcohols, such as C1-C6 alcohols including methanol, ethanol, propanol, butanol, pentanol, and hexanol, including isomers thereof such as 1-propanol and 2-propanol; glycol ethers and thioglycol ethers such as polyalkylene glycols including, but not limited to, propylene glycols such as dipropylene glycol, tripropylene glycol, and tetrapropylene glycol; polymeric glycols such as PEG 200, PEG 300, and PEG 400; thiodiglycol; and mixtures thereof. Additional solvents that can be used include hydantoins and derivatives thereof, dimethyl sulfoxide, methylsulfonylmethane, tetramethylene sulfone, butanetriols such as 1,2,4-butanetriol, acetic acid, and polyalkoxylated triols.

Suitable fluoride-bearing species include ammonium fluoride, ammonium bifluoride, potassium fluoride, sodium fluoride, calcium fluoride, magnesium fluoride, and alkylated ammonium fluorides such as tetrabutylammonium fluoride, among others.

The electrolyte solution can be maintained at a relatively constant temperature. The temperature of the electrolyte solution can be between about 10° and 50° Celsius. In some embodiments, the temperature of the electrolyte solution can be between about 0° and 100° Celsius. In some embodiments, the temperature can be between about 5° and 35° Celsius.

In some embodiments, the electrolyte solution includes about 99.2 vol % organic solvent and about 0.8 vol % water, about 0.20 wt % fluoride-bearing species, and is maintained at about 30° C.

At block 630, a voltage $V_p$ is applied across the anode and cathode(s) through the electrolyte solution for a time period $t_1$ resulting in the formation of metal oxide nanostructures on the surface of the anode. The voltage $V_p$ can be between about 10V and about 60V. In some embodiments, the first voltage $V_p$ is between about 15V and about 30V. In some embodiments, the voltage applied across the anode and cathode is constant for the first time period $t_p$. In other embodiments, the voltage applied across the anode and cathode varies over time throughout the time period $t_p$, as for example when the anodization is run in a galvanostatic mode. The voltage applied across the anode and cathodes may or may not also include a more complex function, such as a ramp, a step function, or a waveform. The time period $t_p$ can be between about 1 minute and about 30 minutes. In some embodiments, the time period $t_p$ is less than about 1 minute. In some embodiments, the time period $t_p$ is between about 2 minutes and about 25 minutes. In some embodiments, the time period $t_p$ is between about 3 minutes and about 20 minutes. In some embodiments, the time period $t_p$ is between about 5 and about 15 minutes. Where the waveform includes periods of 0 voltage, the time period $t_p$ can be considerably longer. For example, in some embodiments, the time period $t_p$ can be between about 30 minutes and about 60 minutes. In some embodiments, the time period $t_p$ can be more than 60 minutes.

At block 640, the metal oxide nanostructures formed during the anodization of block 630 are substantially removed, resulting in a pretreated anode. This removal can be accomplished by exposing the anode with to ultrasound, mechanical cleaning, chemical etchants, or other methods. Chemical etchants can include acids, Basic Oxide Etch, ferric chloride, MicroClean MV (A+B) (available from RBP Chemical Technology), and others. Sufficient removal of the oxide layer can result in a nanotextured surface on the anode. Such nanotextured surface can include pits (e.g., nanopits). In some embodiments, the depth of each pit can be approximately one half the diameter of the pit. The diameters of the pits can be between about 5 and about 100 nanometers. In some embodiments, the diameters of the pits can be between about 20 and about 60 nanometers. In some embodiments, the pits can cover the majority (greater than or equal to about 50% of the surface) of the surface of the anode about removal of the metal oxide nanostructures. In some embodiments, the pits can cover less than 50% of the surface of the anode. In some embodiments, the pits can cover more than 75% of the surface of the anode. In some embodiments, the pits can cover more than 90% of the surface of the anode. In some embodiments, the pits can cover more than 95% of the surface of the anode.

In some embodiments of the methods shown in FIG. 6, the pretreated anode can be soaked in a solvent after removal of the metal oxide nanostructures. In some embodiments, the solvent can be an organic solvent, and free of any acid or hydrogen source. In some embodiments, the solvent can be of low polarity, and include such solvents as methylene chloride, chloroform, benzene, toluene, xylene, hexanes, petroleum ether, and others. In some embodiments, the solvent is hexanes. In some embodiments, the pretreated anode is soaked in the solvent for between about 1 second and about 24 hours. In some embodiments, the pretreated anode is soaked in the solvent for between about 10 seconds and about 2 hours. In some embodiments, the pretreated anode is soaked in the solvent for between about 1 minute and about 1 hour.

In some embodiments of the methods shown in FIGS. 1-6 and described herein, each of the voltages $V_1$ through $V_n$ (depending on the embodiment) can be modulated using an initial ramp and/or a terminating ramp. In some embodiments, the initial and/or terminating ramps can include constant changes in voltage, while in other embodiments the initial and/or terminating ramps can include one or more step functions. The initial and terminating ramps can also be non-linear, for example they can increase or decrease exponentially. For example, in one embodiment, voltage $V_1$ can initially be about 25 volts for a period of time, and then ramped down to zero volts across the anode and a particular cathode by between about 0.04 volts/second to about 2.5 volts per second. In some embodiments, the terminating ramp can reduce the voltage across the anode and a particular cathode by between about 0.04 volts per second to about 0.08 volts per second. In some embodiments, an initial ramp can be used to increase the voltage across the anode and a particular cathode over time. In some embodiments, an initial ramp can be used to increase the voltage across the anode and a particular cathode over time, and then a terminating ramp can be used to decrease the voltage across the anode and that cathode over time.

In some embodiments, a terminating ramp can be used to reduce an initial first voltage across the anode and at least one cathode to a second voltage. In some embodiments, a terminating ramp can be used to decrease the first voltage across the anode and at least one cathode to a second voltage between about 2-50% of the first voltage. In some embodiments, a terminating ramp can be used to decrease the first voltage across the anode and at least one cathode to a second voltage between about 3-20% of the first voltage. In some embodiments, a terminating ramp can be used to decrease the first voltage across the anode and at least one cathode to a second voltage between about 5-15% of the first voltage. In some embodiments, the duration of the second, lower voltage can be between about 10-1000% of the duration of the initial first voltage. In some embodiments, the duration of the second, lower voltage can be between about 20-500% of the first voltage. In some embodiments, the duration of the second, lower voltage is a function of the value of the second, lower voltage: second voltages of between 1-5 volts may or may not require a long duration, between about 15 minutes and about 60 minutes, whereas second voltages greater than 5 volts may or may not have shorter durations between about 1 minute and about 15 minutes.

In some embodiments of the methods shown in FIGS. 1-6 and described herein, during a terminating ramp or a step function to a second, lower voltage, the electrolyte may or may not contain a source of fluoride. In some embodiments, the electrolyte does not contain a source of fluoride.

In some embodiments of the methods shown in FIGS. 1-6 and described herein, during the terminating ramp or the step function to a second, lower voltage, the solvent which composes the electrolyte solution may be modified resulting in a second electrolyte solution. In embodiments where the first electrolyte solution contained ethylene glycol, the ethylene glycol may or may not be exchanged for an aprotic solvent. Any aprotic solvent may be used, including but not limited to acetonitrile, tetrahydrofuran, formamide, dimethylformamide, acetamide, dimethylsulfoxide, methylsulfonylmethane, tetramethylene sulfone, pyrrolidone, N-methylpyrrolidone, ethylene carbonate, and propylene carbonate. In some embodiments, the aprotic solvent is propylene carbonate because it is a liquid at or near room temperature, has low vapor pressure, limited toxicity, and is able to dissolve sufficient amounts of salts. In some embodiments, the exchange of ethylene glycol for an aprotic solvent reduces surface cracking of the anode upon the termination of the anodization.

In some embodiments of the methods shown in FIGS. 1-6 and described herein, a source of oxygen other than water is used in the electrolyte solution(s). For convenience and cost, water can be used as an oxygen source in the electrolyte solutions for a first anodization period. In the cases of a terminating ramp or the step function to a second, lower voltage, water may or may not be replaced in the electrolyte solution in part or in its entirety by an aprotic oxygen source. In some embodiments, the aprotic oxygen source is a single atom oxygen source. In some embodiments, the single atom source of oxygen can be N-alkyl-N-oxides. In other embodiments, the single atom source of oxygen can be N-methyl-morpholine-N-oxide. To increase the rate of the reaction after addition of the aprotic oxygen source, the anode and/or electrolyte solution can be exposed to ultrasonic energy. In other embodiments, the single atom source of oxygen may be nitrous oxide. In embodiments where the single atom source of oxygen is nitrous oxide, the nitrous oxide can be bubbled through the electrolyte.

Some single atom sources of oxygen such as the halogen bleaches are not preferred because the presence of the halogen can lead to degradation of the anode. Aprotic oxygen sources that already contain an oxygen-oxygen bond such as hydrogen peroxide are also not preferred because they are more readily oxidized to molecular oxygen. A small amount of hydrogen peroxide (e.g. less than about 1 wt %) may or may not be present in the electrolyte solution as long as it does not lead to degradation of the anode.

In some embodiments of the methods shown in FIGS. 1-6 and described herein, a base is added to the electrolyte solution near the end of the anodization reaction. Suitable bases include triethanolamine, trialkylamines such as triethylamine, and the like. In some embodiments, a base is added within one minute of the end of the anodization reaction. In some embodiments, a base is added within 30 seconds of the end of the anodization reaction. The amount of base to be added depends upon the basicity of the base. In some embodiments, the amount of base added should exceed the molar amount of the fluoride salt present in the electrolyte solution.

In some embodiments of the methods shown in FIGS. 1-6 and described herein, molecular sieves may be added to the electrolyte solution near the end of the reaction, either as an alternative to or in addition to the addition of a base. In embodiments where the electrolyte solution contains ethylene glycol, 3-4 Å molecular sieves should be used. In some embodiments, the electrolyte solution is gently stirred or agitated after addition of the molecular sieve.

In some embodiments of the methods shown in FIGS. 1-6 and described herein, anode and cathode(s) are placed in electrical contact through an electrolyte solution further including a surface-active species. The surface-active species can include surfactants such as the Tergitol© series, triton X-100, DOWFAXES, pluronics, and others. Cationic and anionic surfactants are not preferred, as they will interfere significantly with the electrode surfaces. In some embodiments, the surface-active species can be present in the electrolyte solution at concentrations from about 0.05 to about 5%. In some embodiments, the surface-active species can be present in the electrolyte at concentrations from about 0.1 to about 3%. In some embodiments, the surface-active species can be present in the electrolyte solution at concentrations from about 0.2 to about 2%. In some embodiments the surface active species can be 1,2 pentanediol, 1,2 hexanediol, and 1,2 octanediol. In some embodiments, these diols can be present in the electrolyte solution at concentrations from about 0.1 to about 20%. In some embodiments, these diols can be present in the electrolyte solution at concentrations from about 1 to about 15%. In some embodiments, these diols can be present in the electrolyte solution at concentrations from about 3 to about 10%.

In some embodiments of the methods shown in FIGS. 1-6 and described herein, during at least part of the time period that a voltage is applied across the anode and cathode(s), the anode is moved (e.g., rotated or translated) relative to the cathode(s). In some embodiments, the anode is mechanically moved (e.g., rotated or translated). In some embodiments, the cathode(s) are mechanically moved relative to the anode. In some embodiments, both the anode and the cathode(s) are mechanically moved relative to one another.

For example, in embodiments where the anode is a stent, the complex geometry of the stent may make it difficult to achieve electric field homogeneity at the surface of the stent during anodization. Such inhomogeneities in the electric field at the surface of the stent may or may not lead to differences in the nanostructured surface that is created during the anodization. As a result of these electric field inhomogeneities, some regions of the stent can experience conditions too aggressive (e.g., too high of a voltage, too high of a temperature, too high concentrations of species in the electrolyte) while other regions of the stent can experience conditions too benign (e.g., too low of a voltage, too low of a temperature, too low concentrations of species in the electrolyte). Too aggressive of conditions can lead to delamination of the metal oxide nanostructure, or corrosion of the anode. Too benign of conditions can lead to incomplete or defective formation of the metal oxide nanostructure. Imparting motion to the anode during the anodization can also increase the homogeneity of the electrolyte, and is an improvement over that than can be typically achieved by the use of a stir bar. If the motion of the anode is also relative to the cathode, an improvement of the electric field uniformity may also be achieved.

In embodiments where the anode is generally cylindrical (e.g., where the anode is a stent), the movement of the cylindrical anode relative to the cathode(s) can be rotational. In some embodiments, the cylindrical anode can be rotated between about 1 and about 200 rpm relative to the cathode(s). In some embodiments, the cylindrical anode can be rotated between about 10 and about 100 rpm. The optimal rotational speed of a cylindrical anode will depend on the diameter of the cylindrical anode. For example, a cylindrical anode with a diameter of 7 mm rotating at 50 rpm has a linear speed at the surface of approximately 1100 mm/minute. In general, larger diameter cylindrical anodes will require lower rotational speeds, and smaller diameter cylindrical anodes will require higher rotational speeds.

In some embodiments, the cylindrically-symmetric cathode(s) can be rotated between about 1 and about 20 rpm relative to the anode. In some embodiments, the cylindrically-symmetric cathode(s) can be rotated between about 5 and about 10 rpm. The optimal rotational speed of a cylindrically-symmetric cathode will depend its diameter. For example, a cylindrically-symmetric cathode with a diameter of 40 mm rotating at 10 rpm has a linear speed at the surface of approximately 1200 mm/minute. In general, larger diameter cathodes will require lower rotational speeds, and smaller diameter cathodes will require higher rotational speeds. In the extreme case in which there is one cathode, and as such does not have cylindrical symmetry, the linear speed can be set by using the equation of the circumference of a circle (=2× π ×radius), and defining the radius as the interelectrode distance.

In some embodiments of the methods shown in FIGS. 1-6 and described herein, the electrolyte solution may or may not be exchanged with an aprotic electrolyte solution that can include propylene carbonate, ammonium sulfate, and N-methyl-morpholine-N-oxide. As the electrolyte solution is exchanged for the aprotic electrolyte solution, the voltage is ramped down or reduced in a step function to a lower voltage, and the anodization is continued at the lower voltage for a period of time. Some embodiments may or may not further include the exchange of the aprotic electrolyte solution with a solution including a salt-free, aprotic solvent. Suitable salt-free, aprotic solvents include acetonitrile, tetrahydrofuran, formamide, dimethylformamide, acetamide, dimethylsulfoxide, methylsulfonylmethane, tetramethylene sulfone, pyrrolidone, N-methylpyrrolidone, ethylene carbonate, and propylene carbonate. Simultaneously, or nearly so, the voltage is reduced to zero. An optional fourth step can include the exchange of the aprotic solvent in the third step with an aprotic solvent with a higher vapor pressure. These include, but are not limited to, ethyl acetate, ethers such as diethyl ether, tetrahydrofuran, acetonitrile, benzene, toluene, methylene chloride, hexanes, petroleum ether, and the like. In some embodiments, the salt-free, aprotic solvent is hexanes. The anode then soaks in the solvent for a period of time. The period of time can be between about 5 to about 60 minutes. In some embodiments, the anode is then removed from the solution and allowed to dry.

In some embodiments of the methods shown in FIGS. 1-6 and described herein, titanium oxide may be deposited on the anode after the anodization step(s). Methods such as physical vapor deposition methods and atomic layer deposition ("ALD") may be used to deposit titanium oxides onto the nanostructured surface after the anodization step(s) described herein. In these embodiments, the deposition temperature is sufficiently high such that the nitinol is present in the austenitic, or parent, phase. On the other hand, the deposition temperature must not be so high as to degrade the mechanical and/or shape memory properties of the nitinol. In particular, low temperature ALD processes are especially suited for this purpose. In some embodiments tetrakis(dimethylamido)titanium can be used as the reactive titanium precursor, and water can be used as the oxidant. Deposition temperatures lower than 100° C. may or may not be achieved. In some embodiments the number of deposition cycles is between about 10 and 100, and in some embodiments the number of deposition cycles is between about 40 and 60. Growth rates of approximately 1 Angstrom per cycle can be achieved under these conditions.

FIGS. 7-10 show an embodiment of an apparatus 700 for forming metal oxide nanostructures including at least one cathode 701. The cathode(s) 701 can be made from any suitable material, including but not limited to platinum, iron, stainless steel, or graphite. In some embodiments, the cathode(s) 701 can be platinum foil. The apparatus may or may not further include a top plate 702, a bottom plate 703, and cathode struts 704. The cathode struts 704 span between the top plate 702 and the bottom plate 703. In some embodiments, the cathode(s) 701 may be affixed to the cathode struts 704 such that at least one surface of the cathode(s) 701 is exposed to an interior area defined by the top plate 702, bottom plate 703, and cathode struts 704. The cathode(s) 701 may be affixed to the cathode struts 704 using any suitable method, including, for example, glue or epoxy.

Figure 10:
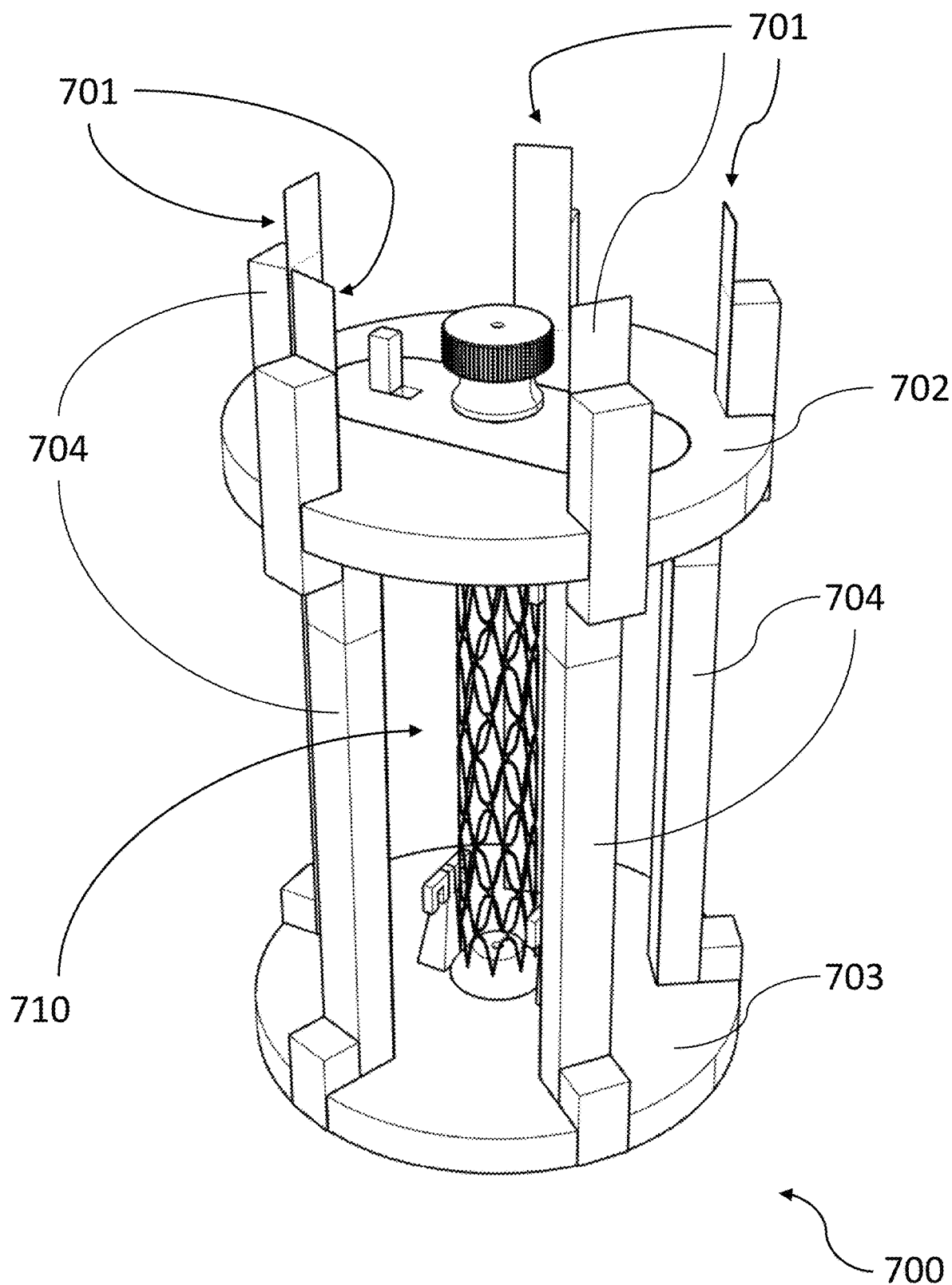
FIG. 10 shows a schematic representation of a partial side and top profile view of the embodiment of the apparatus of FIG. 7.

As shown in FIG. 10, the apparatus 700 can hold an anode in the interior space between the top plate 702 and bottom plate 703. In some embodiments, the anode can be an alloy of nickel and titanium. In some embodiments, the anode can be an alloy of nickel and titanium, with a ratio of nickel to titanium of approximately 1:1. In some embodiments, the anode can be an implantable medical device, including but not limited to a stent 710, as shown in FIG. 10.

The apparatus 700 is arranged such that the anode and cathode(s) 701 can be placed into electrical contact through an electrolyte solution. In some embodiments, the apparatus includes at least two cathodes 701, and the at least two cathodes 701 can be positioned such that each cathode is a similar distance from the anode, and preferably in a symmetrical fashion. In embodiments with at least two cathodes 701, the cathodes 701 can be independently controlled such that different voltages can be applied across each cathode 701 and the anode. In some embodiments, a waveform voltage can be applied each cathode 701 and the anode. In some embodiments, the anode can be moved (e.g., translated, rotated, etc.) relative to the cathode(s) 701. In some embodiments, the cathode(s) 701 can be moved (e.g., translated, rotated, etc.) relative to the anode. In some embodiments, both the anode and the cathode(s) 701 can be moved (e.g., translated, rotated, etc.) relative to one another.

Figure 11:
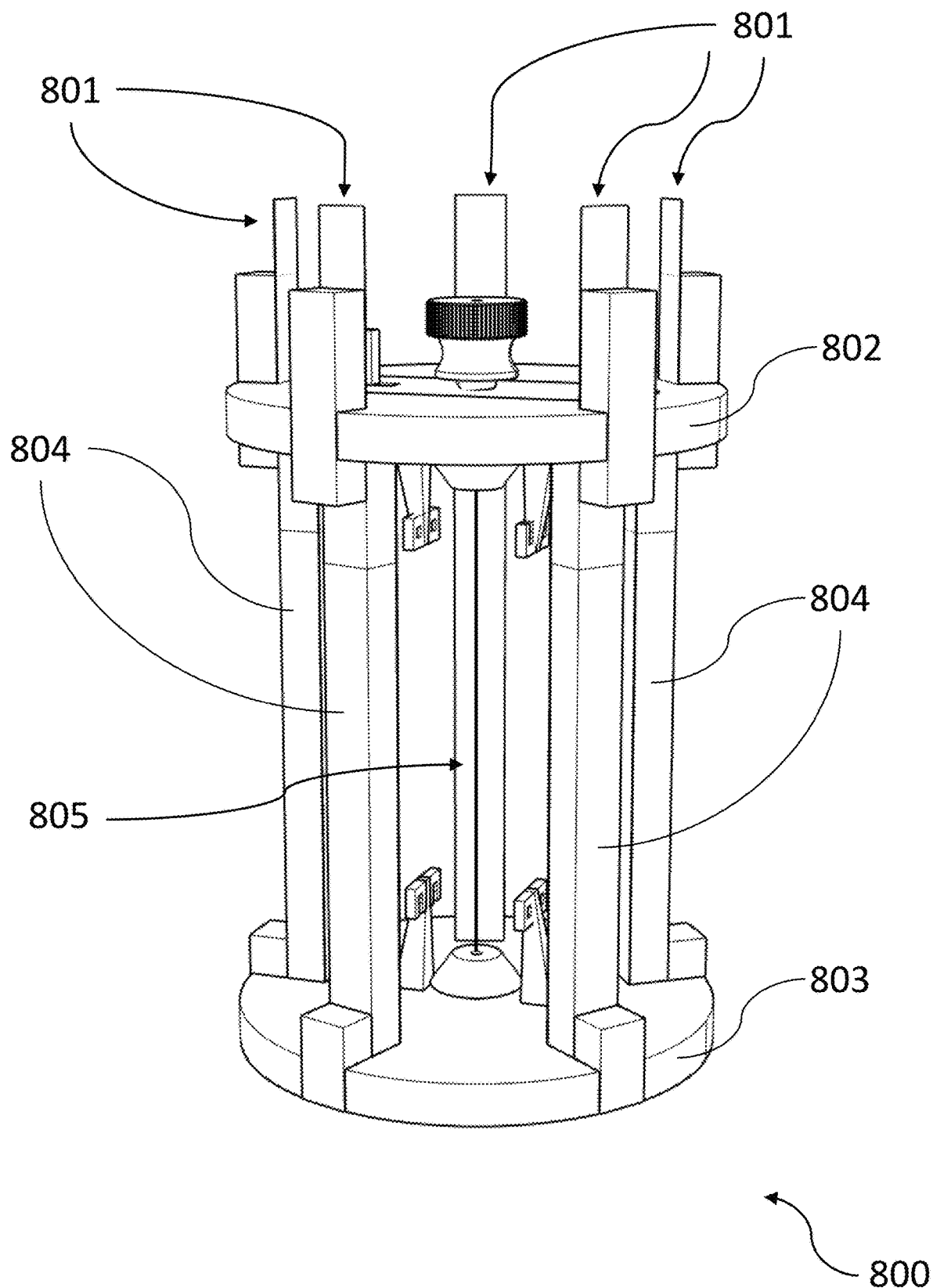
FIG. 11 shows a schematic representation of a partial side and top profile view of one embodiment of an apparatus for forming metal oxide nanostructures.

FIG. 11 shows an embodiment of apparatus 800 for forming metal oxide nanostructures including at least one outer cathode 801 and a central electrode 805. The outer cathode(s) 801 can be made from any suitable material, including but not limited to platinum, iron, stainless steel, or graphite. In some embodiments, the outer cathode(s) 801 can be platinum foil. The apparatus 800 may or may not further include a top plate 802, a bottom plate 803, and cathode struts 804. The cathode struts 804 span between the top plate 802 and the bottom plate 803. In some embodiments, the outer cathode(s) 801 may be affixed to the cathode struts 804 such that at least one surface of the outer cathode(s) 801 is exposed to an interior area defined by the top plate 802, bottom plate 803, and cathode struts 804. The outer cathode(s) 801 may be affixed to the cathode struts 804 using any suitable method, including, for example, glue or epoxy.

The central electrode 805 may be generally positioned such that it would be positioned inside generally coaxially with a cylindrical anode (e.g., a stent). The central electrode 805 can be made from any suitable material, including but not limited to platinum, iron, stainless steel, or graphite. The apparatus 800 is arranged such that an anode (not shown in FIG. 11), outer cathodes 801, and center electrode 805 can be placed into electrical contact through an electrolyte solution. Where a center electrode 805 is included, the cathode(s) 801 and anode can be independently controlled from the center electrode 805 such that different voltages can be applied across the cathode(s) 801, the anode, and the center electrode 805. Thus, in some embodiments, the center electrode 805 can act as a cathode relative to the anode, while in other embodiments the center electrode 805 can act as a guard electrode or an anode.

Figure 12:
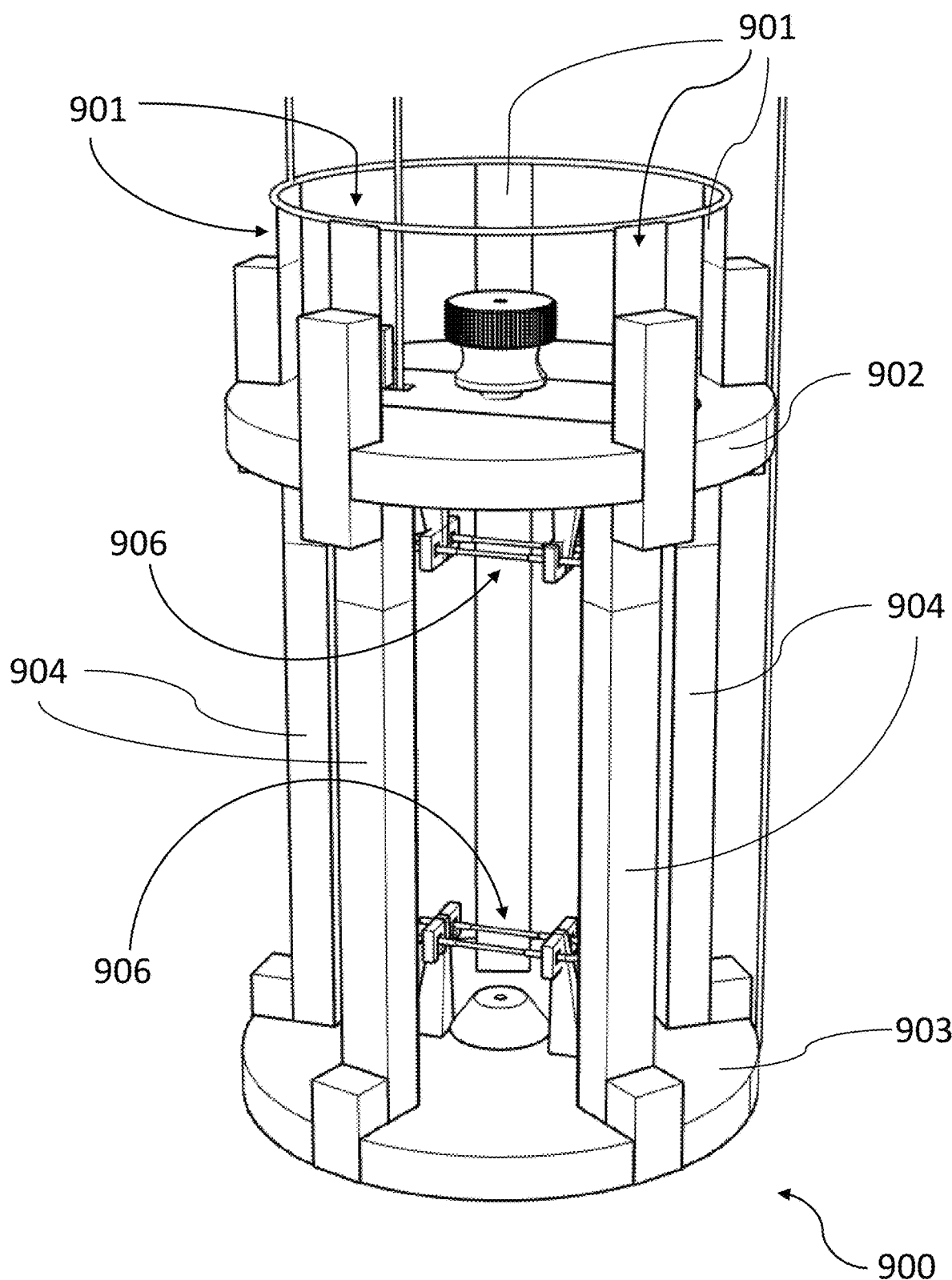
FIG. 12 shows a schematic representation of a partial side and top profile view of one embodiment of an apparatus for forming metal oxide nanostructures.

FIG. 12 shows an embodiment of an apparatus 900 for forming metal oxide nanostructures including at least one cathode 901 and at least one guard electrode 906. The apparatus 900 can be arranged such that an anode (not shown in FIG. 12), cathode(s) 901, and guard electrode(s) 906 can be placed into electrical contact through an electrolyte solution. The cathode(s) 901 can be made from any suitable material, including but not limited to platinum, iron, stainless steel, or graphite. In some embodiments, the cathode(s) 901 can be platinum foil. The apparatus may or may not further include a top plate 902, a bottom plate 903, and cathode struts 904. The cathode struts 904 span between the top plate 902 and the bottom plate 903. In some embodiments, the cathode(s) 901 may be affixed to the cathode struts 904 such that at least one surface of the cathode(s) 901 is exposed to an interior area defined by the top plate 902, bottom plate 903, and cathode struts 904. The cathode(s) 901 may be affixed to the cathode struts 904 using any suitable method, including, for example, glue or epoxy.

The guard electrode(s) 906 can be made of noble metals, such as platinum or iridium, or reactive metals, such as iron, or metal alloys, such as nitinol or stainless steel. In some embodiments, the guard electrodes 906 can be simple wires, as shown in FIG. 12, while in other embodiments the guard electrodes 906 can be rings, meshes, coils, tubes, or stent-like. In some embodiments, the guard electrode(s) 906 may be positioned such that they are not in direct physical contact with the anode, and are positioned such that they reduce non-uniformity in the electric field around the anode during anodization. In some embodiments, the guard electrode(s) 906 are positioned less than 2 mm from the anode. In some embodiments, the guard electrode(s) 906 are positioned less than about 1 mm or less than about 0.5 mm from the anode. In some embodiments, the guard electrode(s) 906 can be electronically controlled in a dependent way, such that they experience the same voltage relative to the cathode(s) 904 as the anode. In other embodiments, the guard electrode(s) 906 may or may not be controlled independently, such that they experience a different voltage relative to the cathode(s) 904 than the anode. In some embodiments, the guard electrode(s) 906 may or may not also experience a voltage relative to the cathode(s) 904 that varies with time.

In embodiments where the anode the anode is symmetrical (e.g., a stent), the guard electrode(s) 906 can be positioned so as to exhibit the same symmetry as the anode. For example, if there is a guard electrode 906 contacting the proximal end of the anode, a guard electrode 906 can be contacting the distal end of the anode. In embodiments where the anode is a bifurcated stent (e.g., a Y-shaped stent), a guard electrode can be placed near or in contact with each of the three ends of the bifurcated stent.

Figure 13:
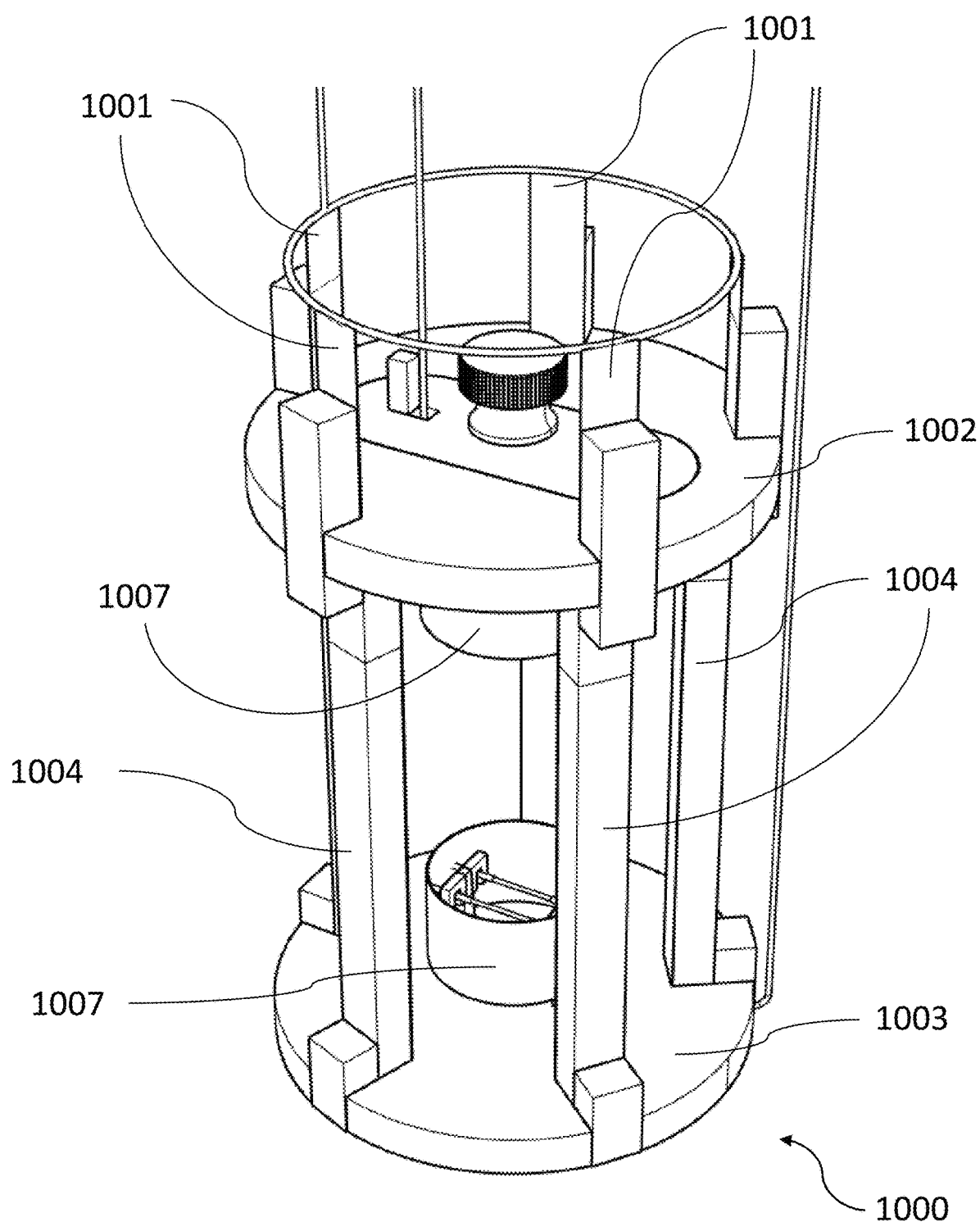
FIG. 13 shows a schematic representation of a partial side and top profile view of one embodiment of an apparatus for forming metal oxide nanostructures.

FIG. 13 shows an embodiment of an apparatus 1000 for forming metal oxide nanostructures including at least one cathode 1001 and at least one cylindrical guard electrode 1007. The apparatus 1000 can be arranged such that an anode (not shown in FIG. 13), the cathode(s) 1001, and the cylindrical guard electrode(s) 1007 can be placed into electrical contact through an electrolyte solution. The cathode(s) 1001 can be made from any suitable material, including but not limited to platinum, iron, stainless steel, or graphite. In some embodiments, the cathode(s) 1001 can be platinum foil. The apparatus may or may not further include a top plate 1002, a bottom plate 1003, and cathode struts 1004. The cathode struts 1004 span between the top plate 1002 and the bottom plate 1003. In some embodiments, the cathode(s) 1001 may be affixed to the cathode struts 1004 such that at least one surface of the cathode(s) 1001 is exposed to an interior area defined by the top plate 1002, bottom plate 1003, and cathode struts 1004. The cathode(s) 1001 may be affixed to the cathode struts 1004 using any suitable method, including, for example, glue or epoxy.

The cylindrical guard electrode(s) 1007 can be made of noble metals, such as platinum or iridium, or reactive metals, such as iron, or metal alloys, such as nitinol or stainless steel. In some embodiments, the cylindrical guard electrode(s) 1007 may be in direct physical contact with the anode. In embodiments where the cylindrical guard electrode(s) 1007 are in direct physical contact with the anode, the guard electrode(s) 1007 may or may not be used to connect the anode to a voltage source or power supply. In other embodiments, the cylindrical guard electrode(s) 1007 may be positioned such that they are not in direct physical contact with the anode, and are positioned such that they reduce non-uniformity in the electric field around the anode during anodization. In some embodiments, the cylindrical guard electrode(s) 1007 are positioned less than 2 mm from the anode. In some embodiments, the cylindrical guard electrode(s) 1007 are positioned less than about 1 mm or less than about 0.5 mm from the anode. In some embodiments, the cylindrical guard electrode(s) 1007 can be electronically controlled in a dependent way, such that they experience the same voltage relative to the cathode(s) 1004 as the anode. In other embodiments, the cylindrical guard electrode(s) 1007 may or may not be controlled independently, such that they experience a different voltage relative to the cathode(s) 1004 than the anode. In some embodiments, the cylindrical guard electrode(s) 1007 may or may not also experience a voltage relative to the cathode(s) 1004 that varies with time.

In embodiments where the anode the anode is symmetrical (e.g., a stent), the cylindrical guard electrode(s) 1007 can be positioned so as to exhibit the same symmetry as the anode. For example, if there is a cylindrical guard electrode 1007 contacting or near the proximal end of the anode, a cylindrical guard electrode 1007 can be contacting or near the distal end of the anode.

Figure 14:
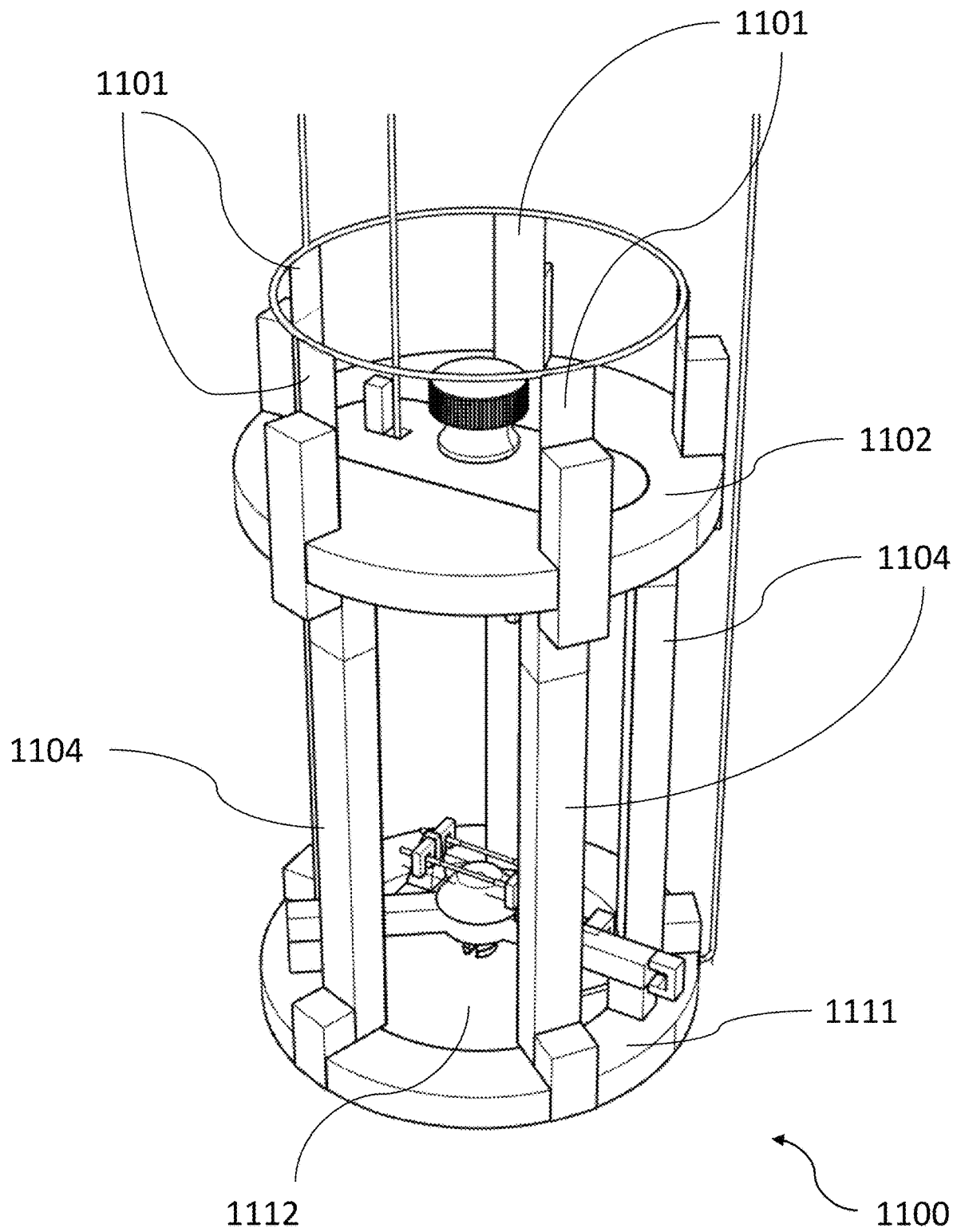
FIG. 14 shows a schematic representation of a partial side and top profile view of one embodiment of an apparatus for forming metal oxide nanostructures.

FIG. 14 shows an embodiment of an apparatus 1100 for forming metal oxide nanostructures including at least one cathode 1101. The cathode(s) 1101 can be made from any suitable material, including but not limited to platinum, iron, stainless steel, or graphite. In some embodiments, the cathode(s) 1101 can be platinum foil. The apparatus may or may not further include a top plate 1102, a bottom ring 1111, and cathode struts 1104. The cathode struts 1104 span between the top plate 1102 and the bottom plate 1111. In some embodiments, the cathode(s) 1101 may be affixed to the cathode struts 1104 such that at least one surface of the cathode(s) 1101 is exposed to an interior area defined by the top plate 1102, bottom plate 1103, and cathode struts 1104. The cathode(s) 1101 may be affixed to the cathode struts 1104 using any suitable method, including, for example, glue or epoxy.

The apparatus 1100 is arranged to hold an anode in the interior space between the top plate 1102 and bottom ring 1111. In some embodiments, the anode can be an alloy of nickel and titanium. In some embodiments, the anode can be an alloy of nickel and titanium, with a ratio of nickel to titanium of approximately 1:1. In some embodiments, the anode can be an implantable medical device, including but not limited to a stent.

The apparatus 1100 is arranged such that the anode and cathode(s) 1101 can be placed into electrical contact through an electrolyte solution. The bottom ring 1111 has an opening 1112 that allows for stirring or agitation of the electrolyte solution. In some embodiments, the apparatus 1100 includes at least two cathodes 1101, and the at least two cathodes 1101 can be positioned such that each cathode is a similar distance from the anode, and preferably in a symmetrical fashion. In embodiments with at least two cathodes 1101, the cathodes 1101 can be independently controlled such that different voltages can be applied across each cathode 1101 and the anode. In some embodiments, a waveform voltage can be applied across each cathode 1101 and the anode. In some embodiments, the anode can be moved (e.g., translated, rotated, etc.) relative to the cathode(s) 1101. In some embodiments, the cathode(s) 1101 can be moved (e.g., translated, rotated, etc.) relative to the anode. In some embodiments, both the anode and the cathode(s) 1101 can be moved (e.g., translated, rotated, etc.) relative to one another.

FIG. 15 shows a schematic representation of one embodiment of an arrangement of an anode 1201 and cathodes segmented along a long axis of the anode. The segmented cathodes can include at least three sets of cathodes: an upper set 1202, a middle set 1203, and a lower set 1204. The upper set of cathodes 1202 is generally aligned with a top end of the anode 1201. The middle set of cathodes 1203 is generally aligned with the middle of the anode 1201. The lower set of cathodes 1204 is generally aligned with a bottom end of the anode 1201.

In the embodiment shown in FIG. 15, the anode 1201 is depicted as a stent. In some embodiments, the anode 1201 can be an alloy of nickel and titanium. In certain embodiments, the anode 1201 can be an alloy of nickel and titanium, with a ratio of nickel to titanium of approximately 1:1. In some embodiments, the anode 1201 can be an implantable medical device, including but not limited to a stent. The cathodes 1202, 1203, and 1204 can be made from any suitable material, including but not limited to platinum, iron, stainless steel, or graphite.

In some embodiments, the at least three sets of cathodes are controlled independently of one another. In some embodiments, the upper set of cathodes 1202 and the lower set of cathodes 1204 are commonly controlled, and the middle set of cathodes 1203 is controlled independently from the commonly-controlled upper and lower sets of cathodes 1202 and 1204. In some embodiments, this arrangement of cathodes and an anode can be used to selectively control the electric field experienced by the anode 1201 at the top and bottom of the anode relative to the middle of the anode.

FIG. 16 shows a schematic representation of another embodiment of an arrangement of an anode 1301 and cylindrical cathodes segmented along a long axis of the anode. The segmented cathodes can include at least three cathodes: an upper cathode 1302, a middle cathode 1303, and a lower cathode 1304. The upper cathode 1302 is generally aligned with a top end of the anode 1301. The middle cathode 1303 is generally aligned with the middle of the anode 1301. The lower cathode 1304 is generally aligned with a bottom end of the anode 1301.

In the embodiment shown in FIG. 16, the anode 1301 is depicted as a stent. In some embodiments, the anode 1301 can be an alloy of nickel and titanium. In certain embodiments, the anode 1301 can be an alloy of nickel and titanium, with a ratio of nickel to titanium of approximately 1:1. In some embodiments, the anode 1301 can be an implantable medical device, including but not limited to a stent. The cathodes 1302, 1303, and 1304 can be made from any suitable material, including but not limited to platinum, iron, stainless steel, or graphite.

In some embodiments, the at least three cathodes are controlled independently of one another. In some embodiments, the upper cathode 1302 and the lower cathode 1304 are commonly controlled, and the middle cathode 1303 is controlled independently from the commonly-controlled upper and lower cathodes 1302 and 1304. In some embodiments, this arrangement of cathodes and an anode can be used to selectively control the electric field experienced by the anode 1301 at the top and bottom of the anode relative to the middle of the anode.

Figure 17:
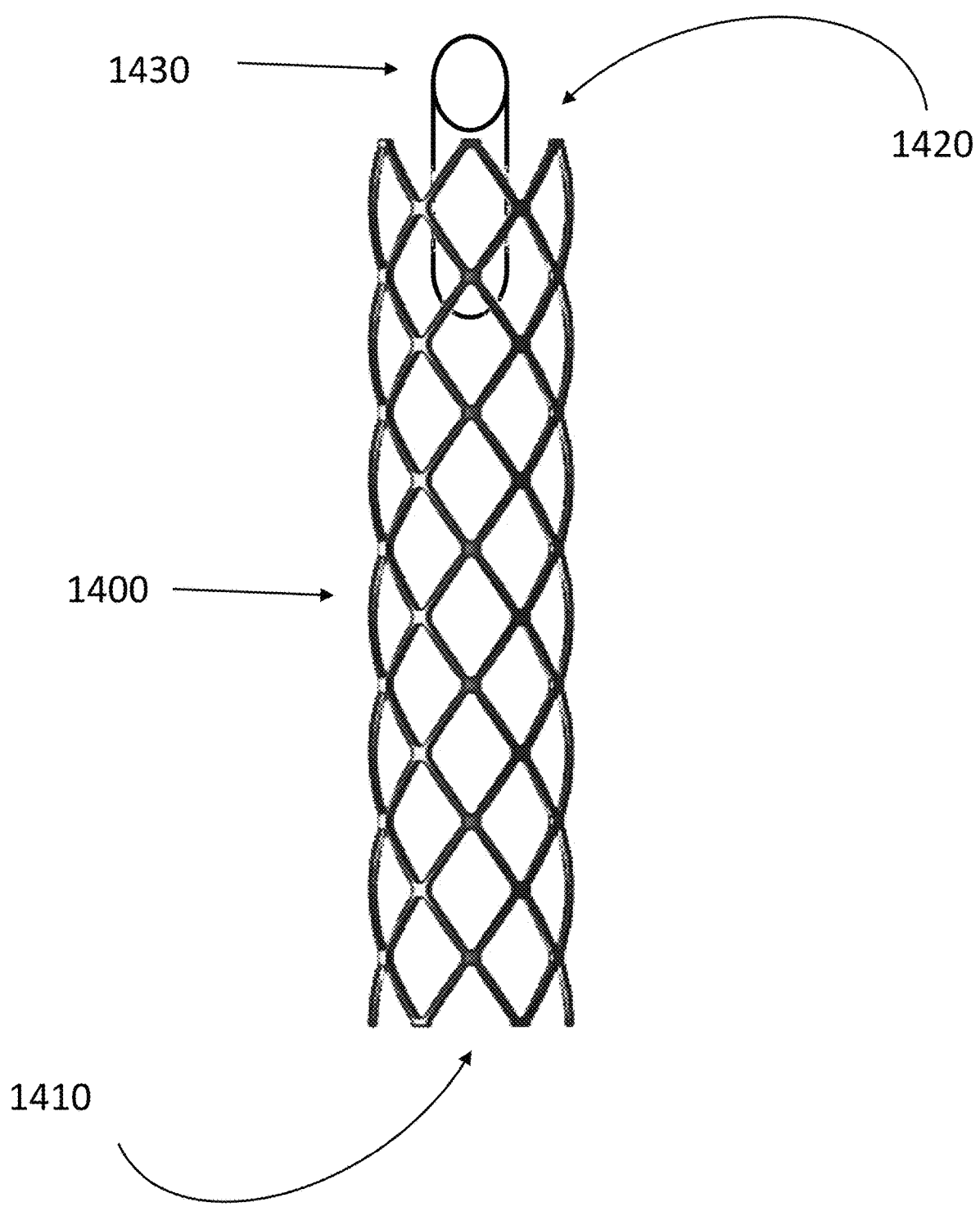
FIG. 17 shows a schematic representation of an arrangement of an anode and a non-contacting electrode.

FIG. 17 shows a schematic representation of an arrangement of an anode and a non-contacting electrode. A representative stent 1400 has an open end 1410 and an electrode end 1420. The electrode end 1420 is placed in proximity to, but not in contact with, a non-contacting guard electrode 1430 during anodization, with the non-contacting guard electrode 1430 generally positioned coaxially with the stent 1400.

FIG. 18 shows a schematic representation of one embodiment of an arrangement of an anode 1501, an insulating layer 1502, and a cathode 1503 positioned inside the anode. In the embodiment shown, the anode 1501, insulating layer 1502, and cathode 1503 are arranged generally coaxially, with the cathode 1503 positioned inside the insulating layer 1502, which is positioned inside the anode 1501.

In the embodiment shown in FIG. 18, the anode 1501 is depicted as a stent. In some embodiments, the anode 1501 can be an alloy of nickel and titanium. In certain embodiments, the anode 1501 can be an alloy of nickel and titanium, with a ratio of nickel to titanium of approximately 1:1. In some embodiments, the anode 1501 can be an implantable medical device, including but not limited to a stent. The insulating layer 1502 can be made from mesh tubing, for example, nylon mesh tubing, and can be positioned to prevent inadvertent short-circuiting between the anode 1501 and cathode 1503. The cathode 1503 can be made from any suitable material, including but not limited to platinum, iron, stainless steel, or graphite.

Example 1. Forming Metal Oxide Nanostructures on a Nickel Titanium Stent at Low Voltages and Short Times An electrolyte solution was prepared containing 0.8 vol % deionized water ($H_2O$) (e.g., 0.8 ml), 0.20 wt % ammonium fluoride ($NH_4F$) (e.g., 0.2 g) (Sigma Aldrich), and 99.2 vol % ethylene glycol (e.g., 99.2 ml) (Sigma Aldrich). The electrolyte solution was brought to and maintained at 22° C.

A 40 mm×7 mm (length×diameter) nitinol stent (Lumenous, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 $mm^2$.

Figure 33:
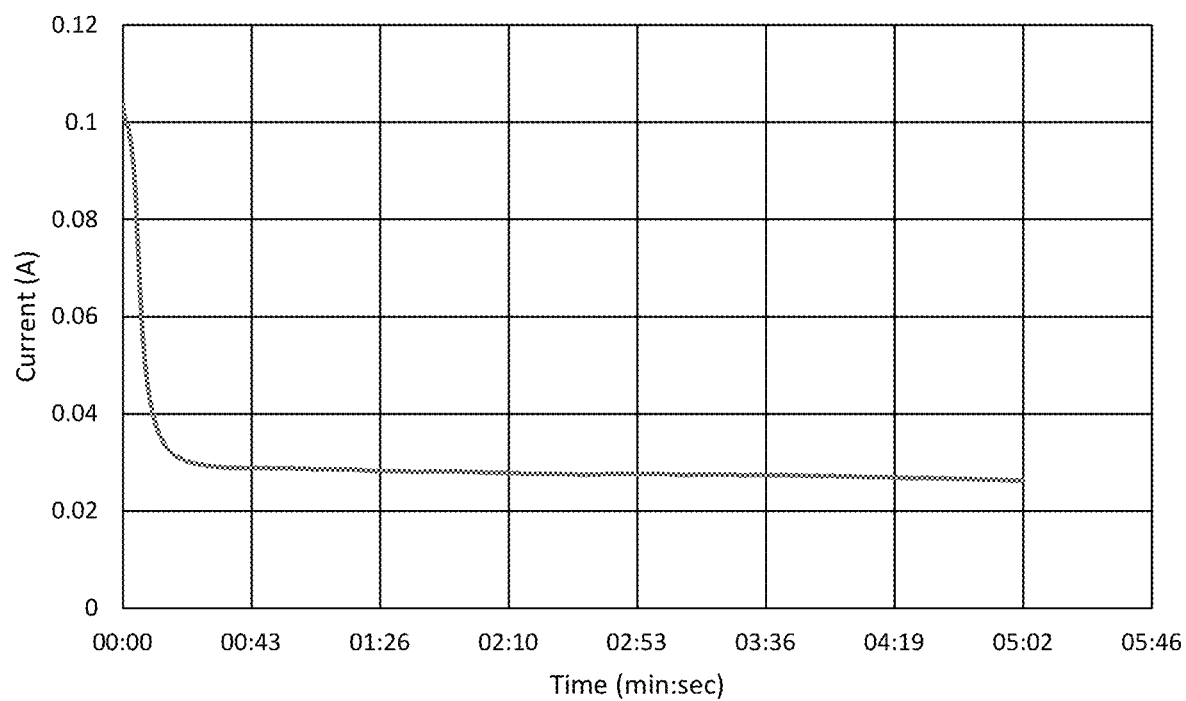
FIG. 33 shows a representative current profile resulting from performing the method described in Example 1.

A power supply (Agilent Technologies) provided a constant voltage of 25V between the anode (nitinol stent) and platinum cathodes for 5 minutes. During this time, the current was variable as monitored by a digital multimeter (Agilent Technologies) connected to a desktop computer running BenchVue 3.1 (Keysight Technologies). A representative current profile is shown in FIG. 33.

Figure 19A:
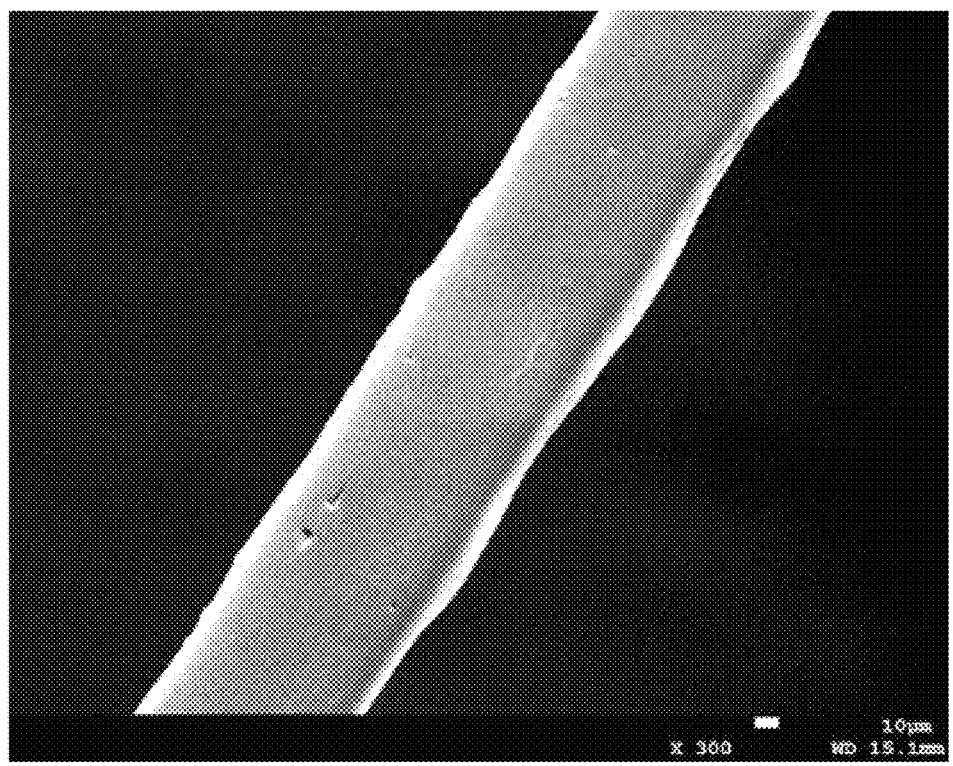
FIGS. 19A-B show representative scanning electron microscope (SEM) images of a metal oxide surface resulting from the method described in Example 1.
Figure 19B:
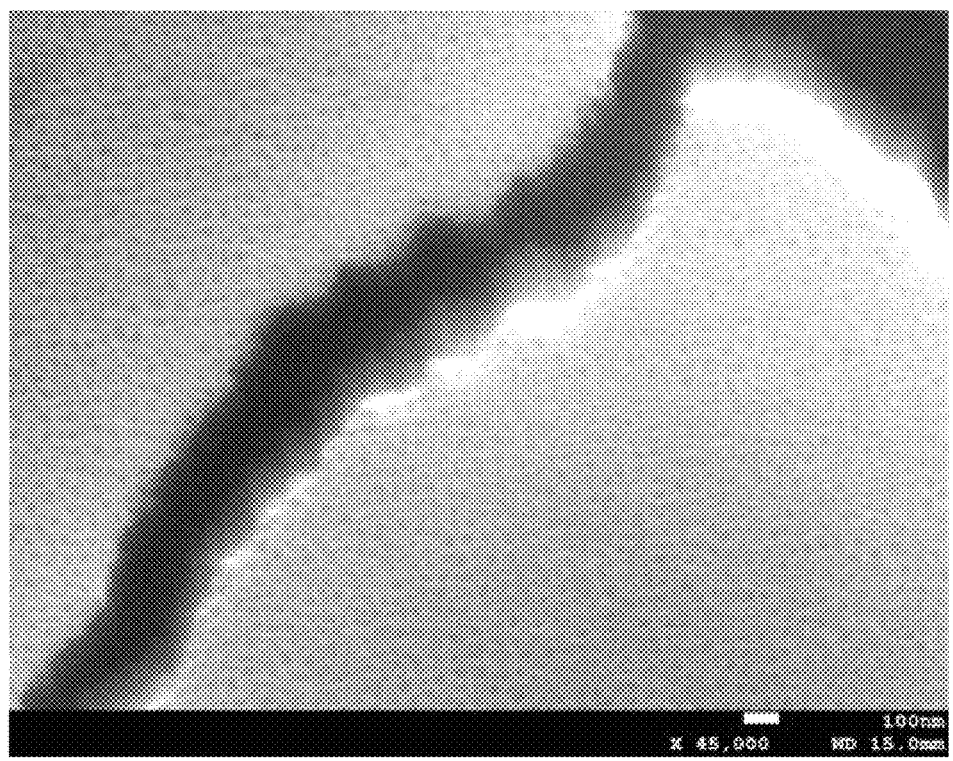

After the 5-minute run, the stent was rinsed in deionized water and kept in 70% ethanol until further use or evaluation. The stent was then imaged using scanning electron microscopy (SEM). Representative SEM images of the resulting metal oxide nanostructures are shown in FIGS. 19A-B.

Example 2. Forming Metal Oxide Nanostructures on Nickel Titanium Foil Wherein the Voltage Applied Across the Anode and the Cathode(s) is a Waveform An electrolyte solution was prepared containing 0.8 vol % deionized water ($H_2O$) (e.g., 0.8 ml), 0.20 wt % ammonium fluoride (NH$_4$F) (e.g., 0.2 g) (Sigma Aldrich), and 99.2 vol % ethylene glycol (e.g., 99.2 ml) (Sigma Aldrich). The electrolyte solution was brought to and maintained at 22° C.

50 mm×50 mm×0.127 mm (W×H×D) nitinol foil (Lumenous, Inc.) was cut into 6 mm×6 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g., 6 mm×6 mm).

Figure 34:
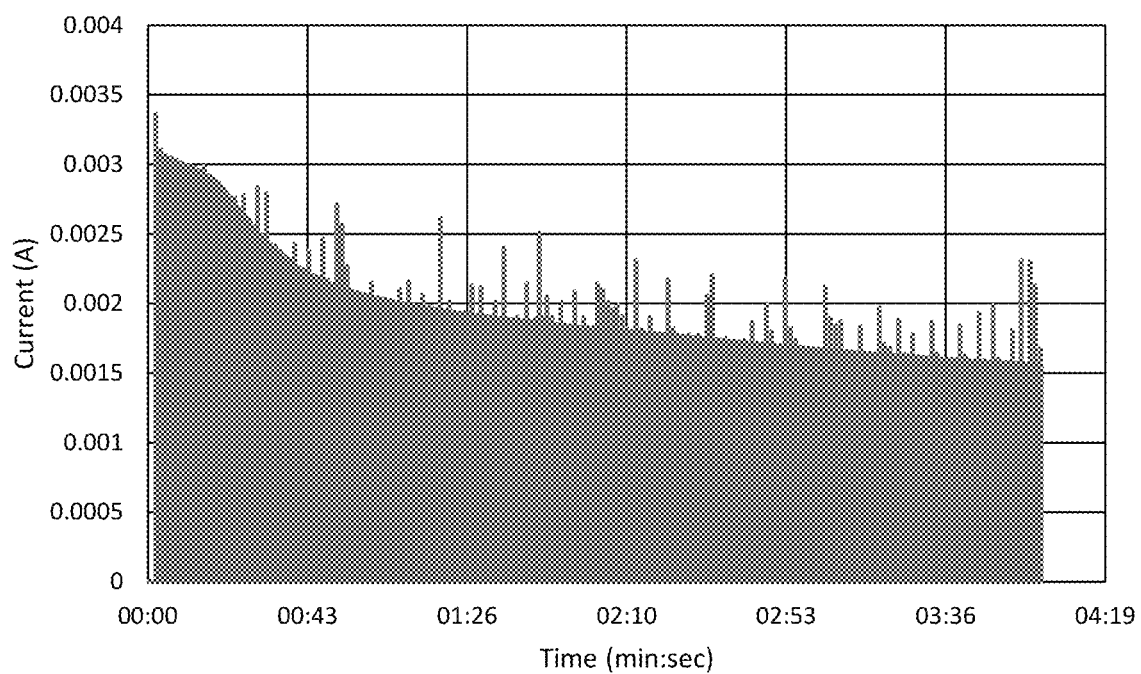
FIG. 34 shows a representative current profile resulting from performing the method described in Example 2.

A power supply (Agilent Technologies) provided a variable voltage of values 0V and 25V between the anode (nitinol coupon) and platinum cathode for 10 minutes, with repeating time periods of 100 ms at 25V followed by 100 ms at 0V. During this time, the current was variable as monitored by a digital multimeter (Agilent Technologies) connected to a desktop computer running BenchVue 3.1 (Keysight Technologies). A representative current profile is shown in FIG. 34.

Figure 20A:
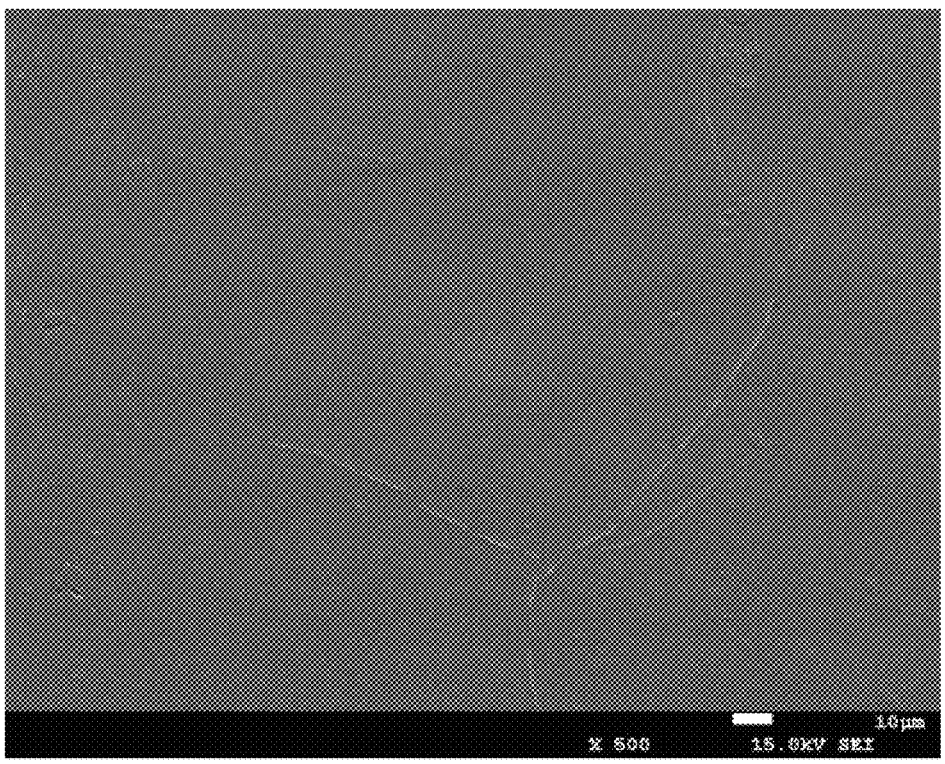
FIGS. 20A-B show representative SEM images of a metal oxide surface resulting from the method described in Example 2.
Figure 20B:
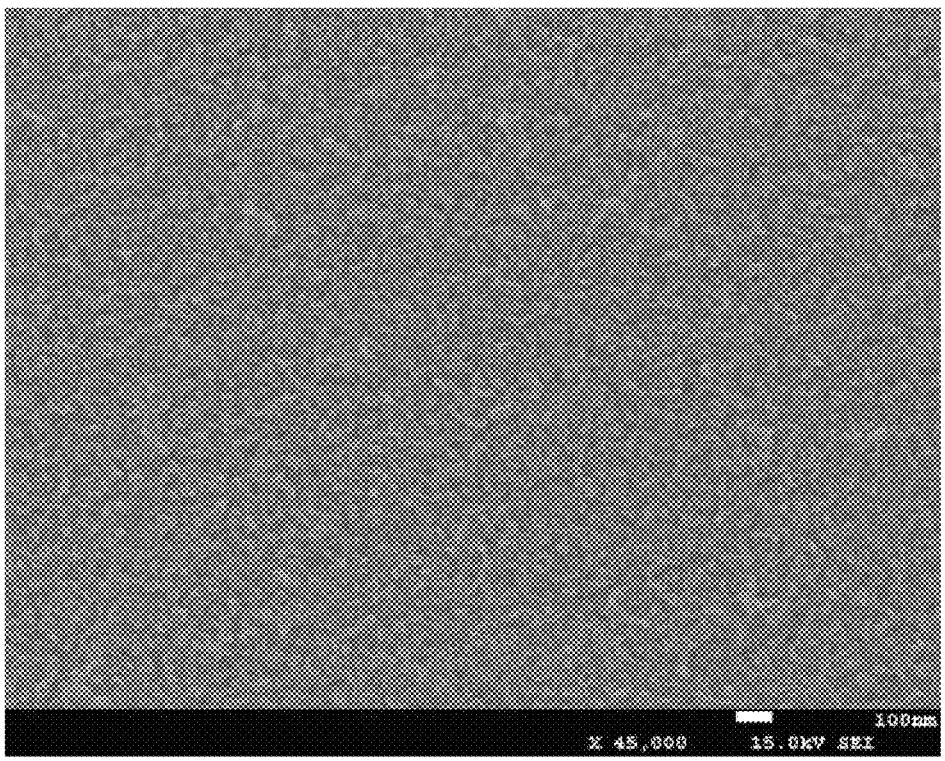

After the 10 minute run, the coupons were rinsed in deionized water and kept in 70% ethanol until further use or evaluation. Some of the coupons were then imaged using SEM. Representative SEM images are shown in FIGS. 20A-B.

Example 3. Forming Metal Oxide Nanostructures on a Nickel Titanium Stent Wherein the Anode Includes a Non-Contacting Guard Electrode An electrolyte solution was prepared containing 0.8 vol % deionized water (H$_2$O) (e.g., 0.8 ml), 0.20 wt % ammonium fluoride (NH$_4$F) (e.g., 0.2 g) (Sigma Aldrich), and 99.2 vol % ethylene glycol (e.g., 99.2 ml) (Sigma Aldrich). The electrolyte solution was brought to and maintained at 22° C.

A 15 mm×3 mm nitinol stent (Lumenous, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14, with electrical contact was made by attaching a platinum wire to the center part of the stent. Furthermore, a non-contacting guard electrode was positioned coaxially in one end of the stent. The guard electrode was inserted 0.5 mm inside the end of the stent. The other end of the stent was left open. The center of the secured nitinol stent was positioned approximately 2 cm from the platinum cathodes (Sigma Aldrich). The area of the 5 exposed platinum cathodes was 5×5 mm×40 mm=1000 mm$^2$.

Figure 35:
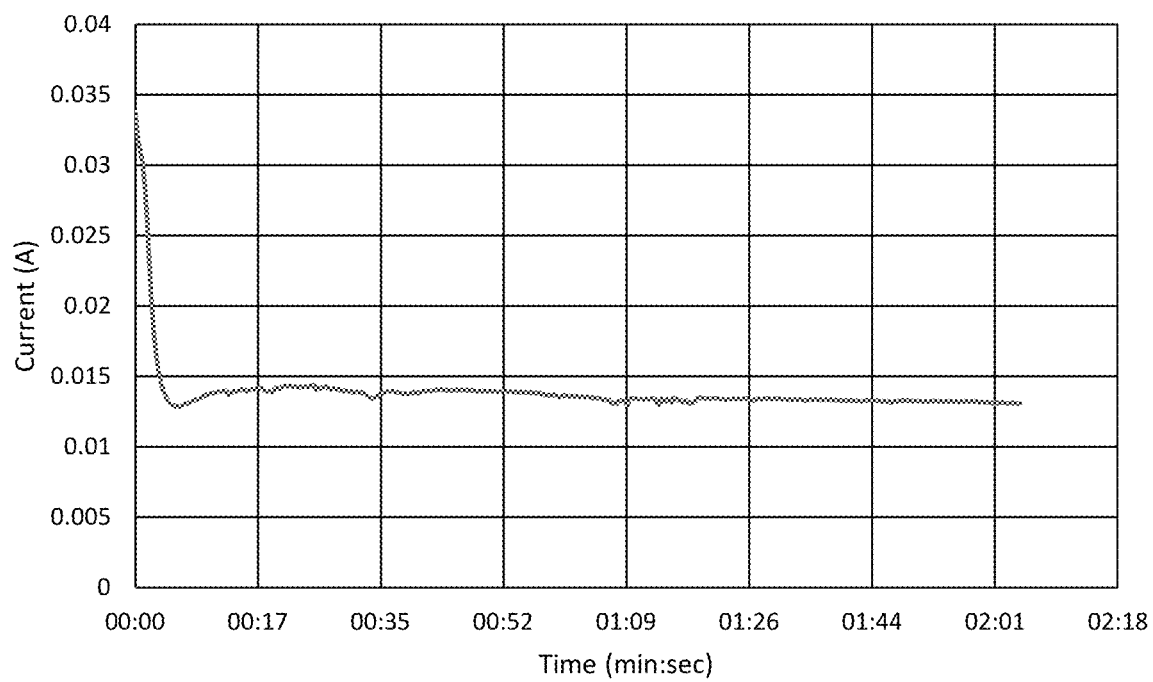
FIG. 35 shows a representative current profile resulting from performing the method described in Example 3.

A power supply (Agilent Technologies) provided a constant voltage of 25V between the anode (nitinol stent) and platinum cathodes for 2 minutes. During this time, the current was variable as monitored by a digital multimeter (Agilent Technologies) connected to a desktop computer running BenchVue 3.1 (Keysight Technologies). A representative current profile is shown in FIG. 35.

After the 2 minute run, the stent was rinsed in deionized water and kept in 70% ethanol until further use or evaluation. The stent was then imaged using SEM. A schematic representation of the setup is shown in FIG. 17. The representative stent 1400 has an open end 1410 and an electrode end 1420. The electrode end 1420 was placed in proximity to a non-contacting guard electrode 1430 during anodization, with the non-contacting guard electrode 1430 generally positioned coaxially with the stent 1400.

Figure 21A:
FIGS. 21A-B show representative SEM images of a metal oxide surface resulting from the method described in Example 3.
Figure 21B:
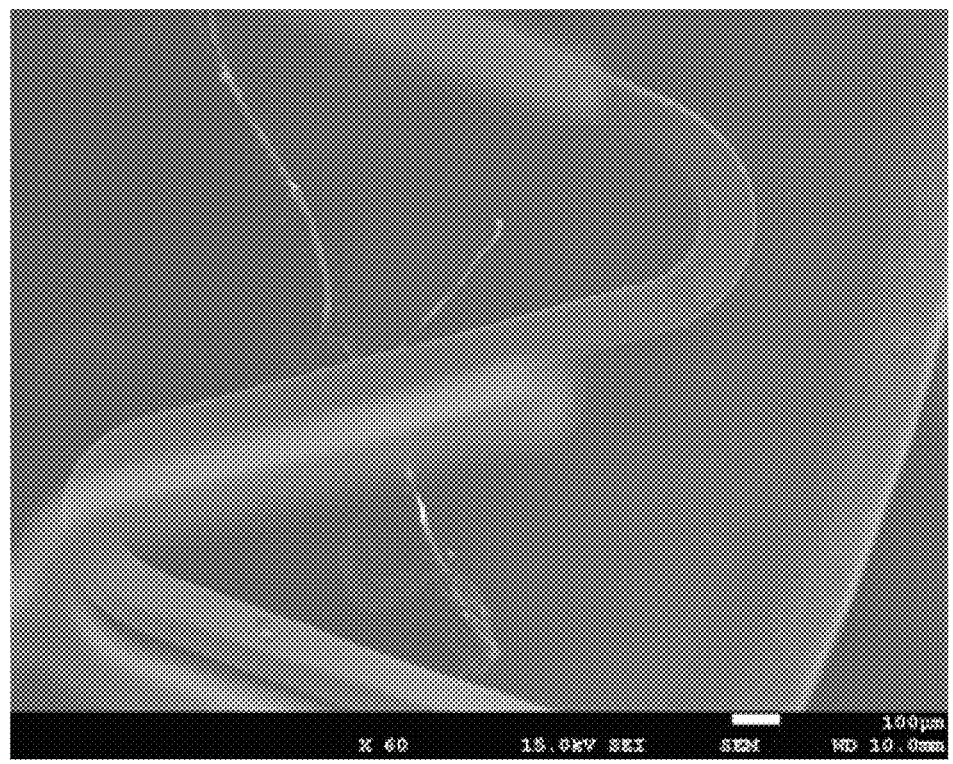

Representative SEM images of the open end of the stent and the end of the stent with the guard electrode are shown in FIGS. 21A-B. FIG. 21A shows a representative SEM image of the open end of the stent. FIG. 21B shows a representative SEM image of the end of the stent with the guard electrode. Corrosion and flaking can be seen on the open (unguarded) end.

Example 4. Forming Metal Oxide Nanostructures on a Nickel Titanium Stent Wherein the Anode Includes a Contacting Guard Electrode An electrolyte solution was prepared containing 0.8 vol % deionized water (H$_2$O) (e.g., 0.8 ml), 0.20 wt % ammonium fluoride (NH$_4$F) (e.g., 0.2 g) (Sigma Aldrich), and 99.2 vol % ethylene glycol (e.g., 99.2 ml) (Sigma Aldrich). The electrolyte solution was brought to and maintained at 22° C.

A 15 mm×3 mm nitinol stent (Lumenous, Inc.) was ultrasonically cleaned with acetone, ethanol, and deionized water for 5 minutes each. It was then kept in 70% ethanol until further use. Prior to anodization, the stent was rinsed in deionized water and air dried.

For anodization the stent was secured in an apparatus similar to the embodiment shown in FIG. 14, with electrical contact being made by attaching a platinum wire to each end of the stent. Thus, both ends of the stent were in electrical contact with the anodic platinum wire. The center of the secured nitinol stent was positioned approximately 2 cm from the platinum cathodes (Sigma Aldrich). The area of the 5 exposed platinum cathodes was 5×5 mm×40 mm=1000 mm$^2$.

Figure 36:
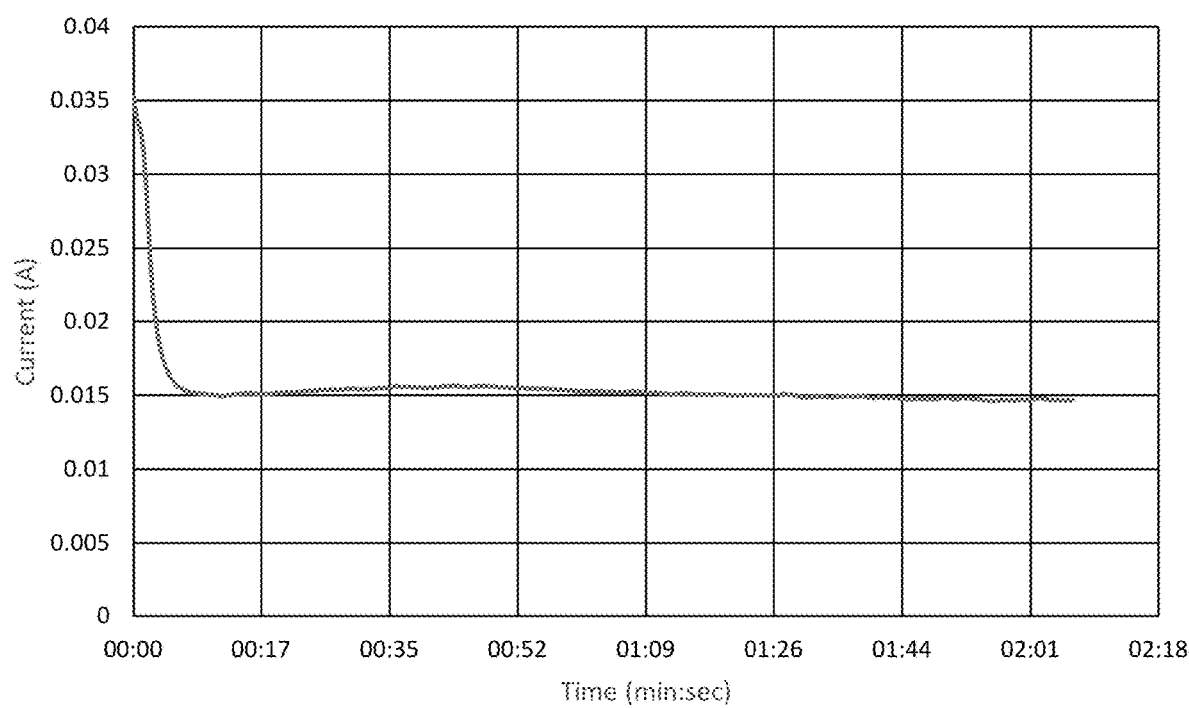
FIG. 36 shows a representative current profile resulting from performing the method described in Example 4.

A power supply (Agilent Technologies) provided a constant voltage of 25V between the anode (nitinol stent) and platinum cathodes for 2 minutes. During this time, the current was variable as monitored by a digital multimeter (Agilent Technologies) connected to a desktop computer running BenchVue 3.1 (Keysight Technologies). A representative current profile is shown in FIG. 36.

Figure 22A:
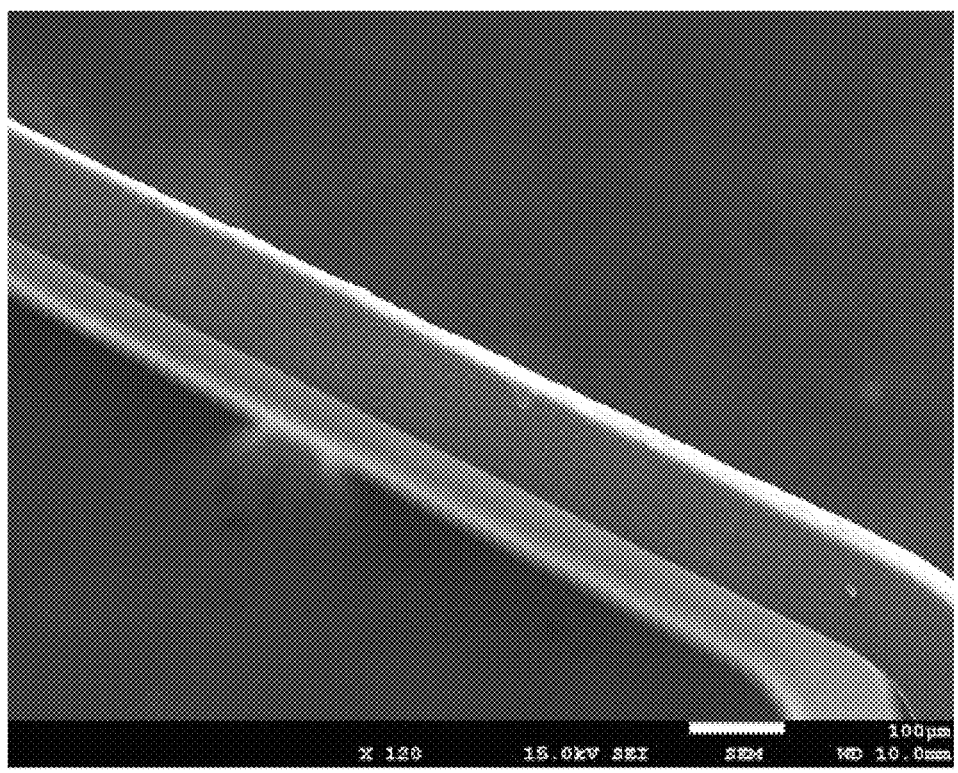
FIGS. 22A-B show representative SEM images of a metal oxide surface resulting from the method described in Example 4.
Figure 22B:
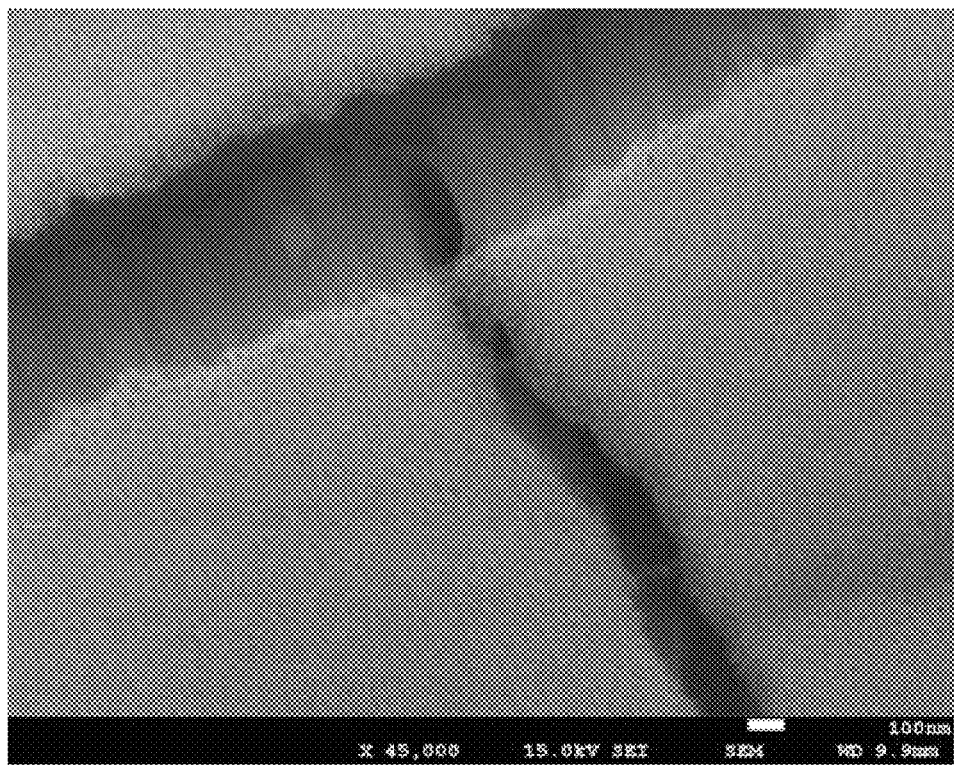

After the 2-minute run, the stent was rinsed in deionized water and kept in 70% ethanol until further use or evaluation. The stent was then imaged using SEM. Representative SEM images are shown in FIGS. 22A-B.

Example 5. Forming Metal Oxide Nanostructures on Nickel Titanium Foil Wherein the Voltage Applied Across the Anode and the Cathode(s) Isa Step Function An electrolyte solution was prepared containing 0.8 vol % deionized water (H$_2$O) (e.g., 0.8 ml), 0.20 wt % ammonium fluoride (NH$_4$F) (e.g., 0.2 g) (Sigma Aldrich), and 99.2 vol % ethylene glycol (e.g., 99.2 ml) (Sigma Aldrich). The electrolyte solution was brought to and maintained at 22° C.

50 mm×50 mm×0.127 mm (W×H×D) nitinol foil (Lumenous, Inc.) was cut into 6 mm×6 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g., 6 mm×6 mm).

Figure 37:
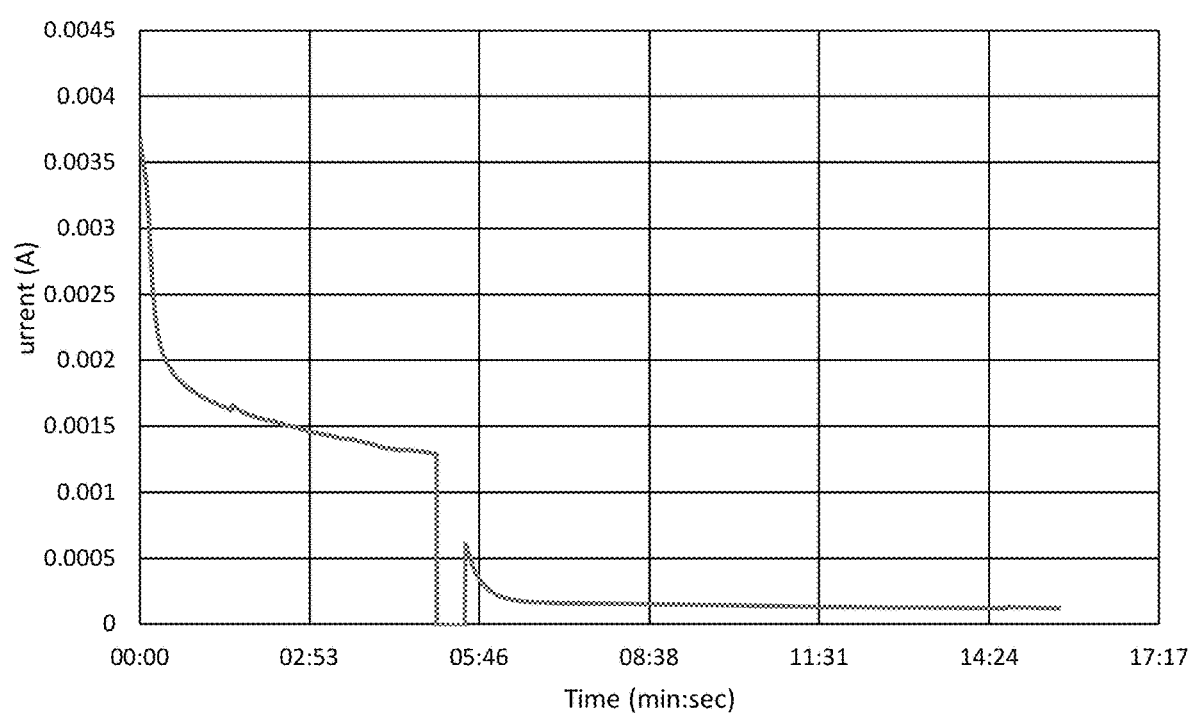
FIG. 37 shows a representative current profile resulting from performing the method described in Example 5.

A power supply (Agilent Technologies) provided a voltage of 25V between the anode (nitinol coupon) and platinum cathode for 5 minutes. The power supply was disconnected momentarily, and the voltage reset to 5V. The anodization was subsequently continued at this second, lower voltage for 10 minutes. During this time, the current was variable as monitored by a digital multimeter (Agilent Technologies) connected to a desktop computer running BenchVue 3.1 (Keysight Technologies). A representative current profile is shown in FIG. 37.

Figure 23A:
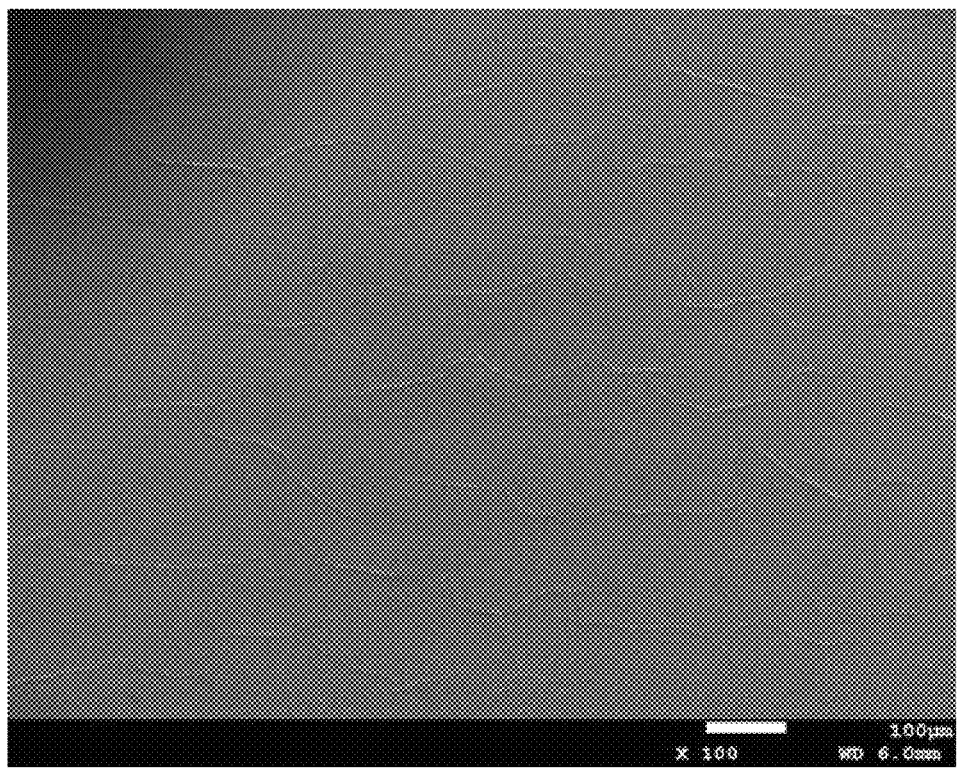
FIGS. 23A-B show representative SEM images of a metal oxide surface resulting from the method described in Example 5.
Figure 23B:
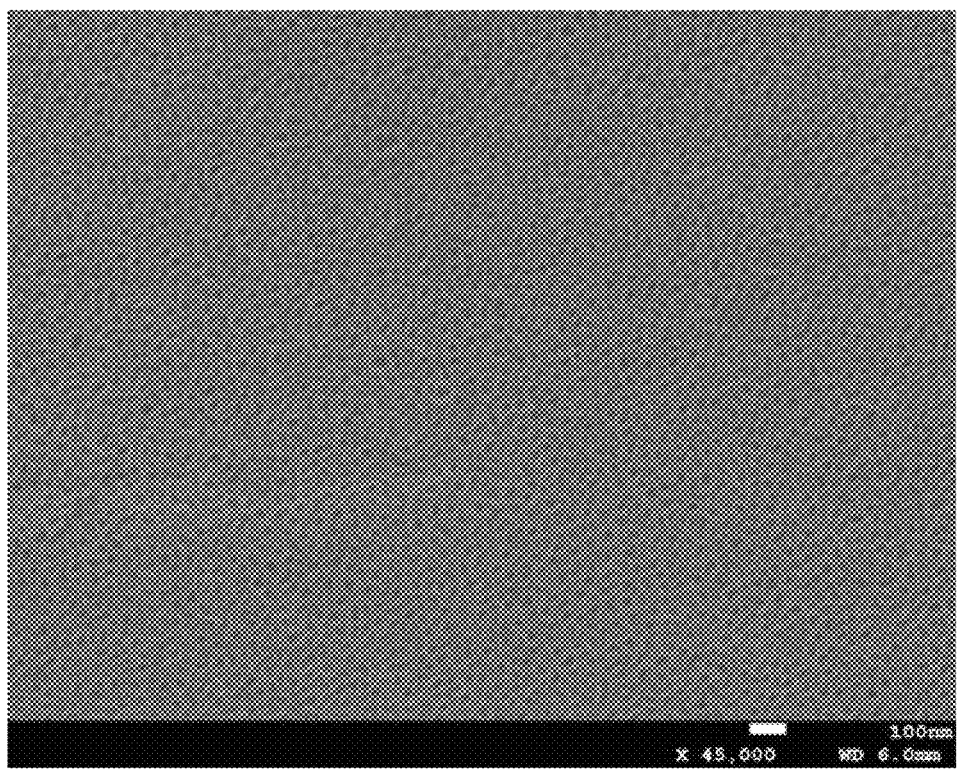

After the entire 15 minute run, the coupons were rinsed in deionized water and kept in 70% ethanol until further use or evaluation. Some of the coupons were then imaged using SEM. Representative SEM images are shown in FIGS. 23A-B.

Example 6. Forming Metal Oxide Nanostructures on Nickel Titanium Foil Wherein the Anode has been Pretreated An electrolyte solution was prepared containing 0.8 vol % deionized water ($H_2O$) (e.g., 0.8 ml), 0.20 wt % ammonium fluoride ($NH_4F$) (e.g., 0.2 g) (Sigma Aldrich), and 99.2 vol % ethylene glycol (e.g., 99.2 ml) (Sigma Aldrich). The electrolyte solution was brought to and maintained at 30° C.

50 mm×50 mm×0.127 mm (W×H×D) nitinol foil (Lumenous, Inc.) was cut into 6 mm×6 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g., 6 mm×6 mm).

Figure 38:
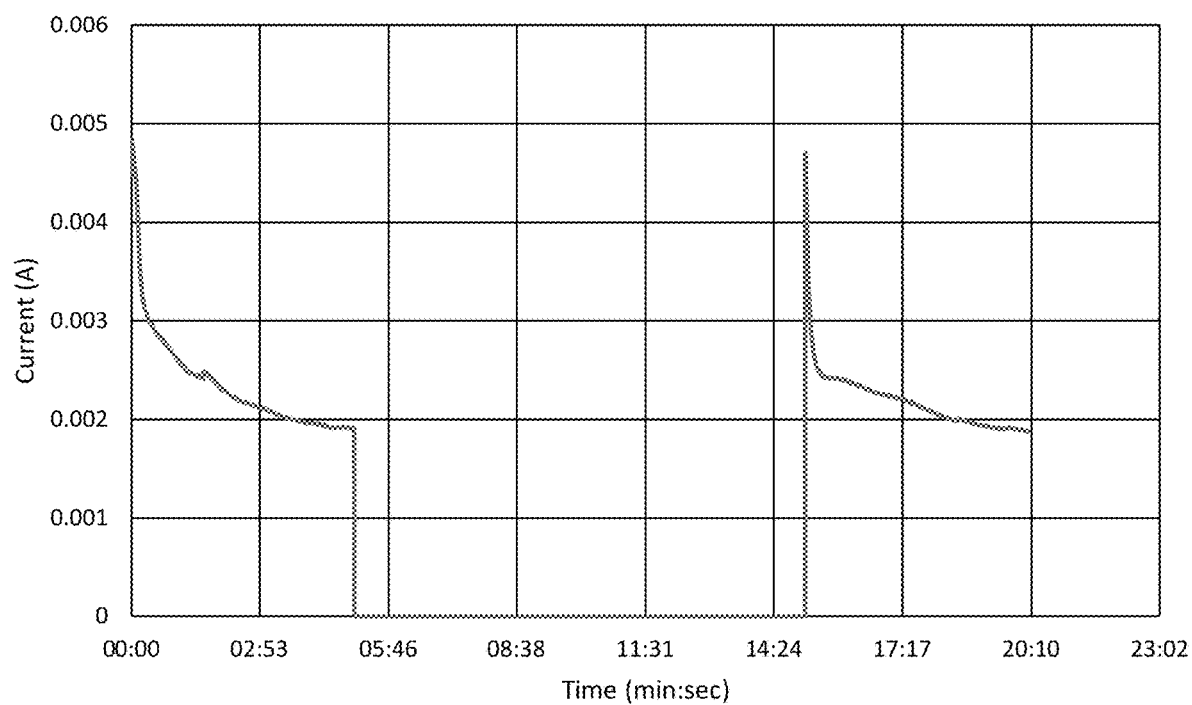
FIG. 38 shows a representative current profile resulting from performing the method described in Example 6.

A power supply (Agilent Technologies) provided a constant voltage of 25V between the anode (nitinol foil) and platinum cathode for 5 minutes. During this time, the current was variable as monitored by a digital multimeter (Agilent Technologies) connected to a desktop computer running BenchVue 3.1 (Keysight Technologies). A representative current profile is shown in FIG. 38.

Figure 24:
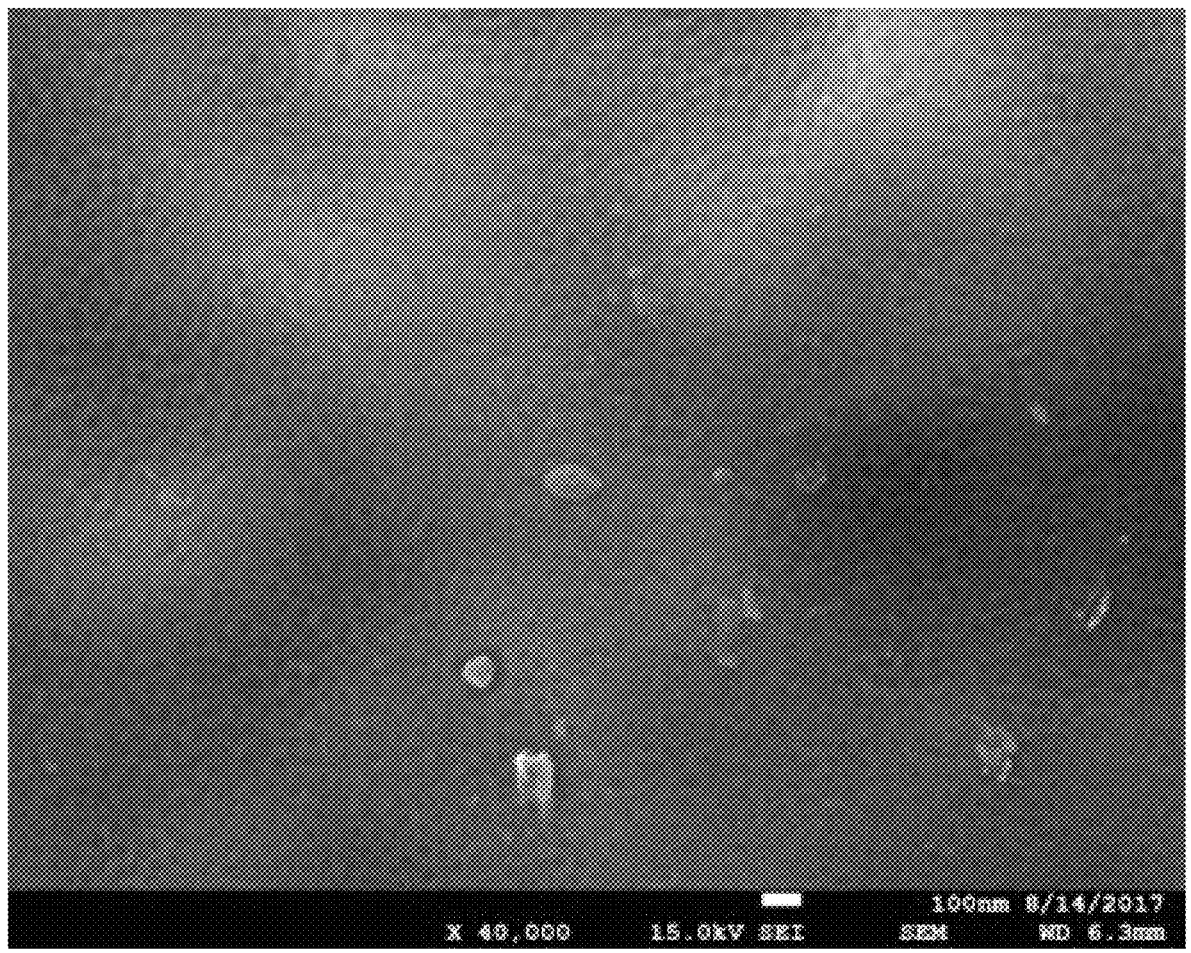
FIG. 24 shows a representative SEM image of a metal oxide surface resulting from the method described in Example 6 after soaking in buffered oxide etch (BOE) but prior to the final anodization period.

After the 5-minute run, the foil was rinsed in deionized water and air dried. Subsequently, the foil was soaked in Basic Oxide Etch (BOE) for 5 seconds. This etching resulted in removal of the nanostructured oxide surface. The foil was then imaged using SEM. A representative SEM image of the foil at this stage is shown is shown in FIG. 24.

Figure 25A:
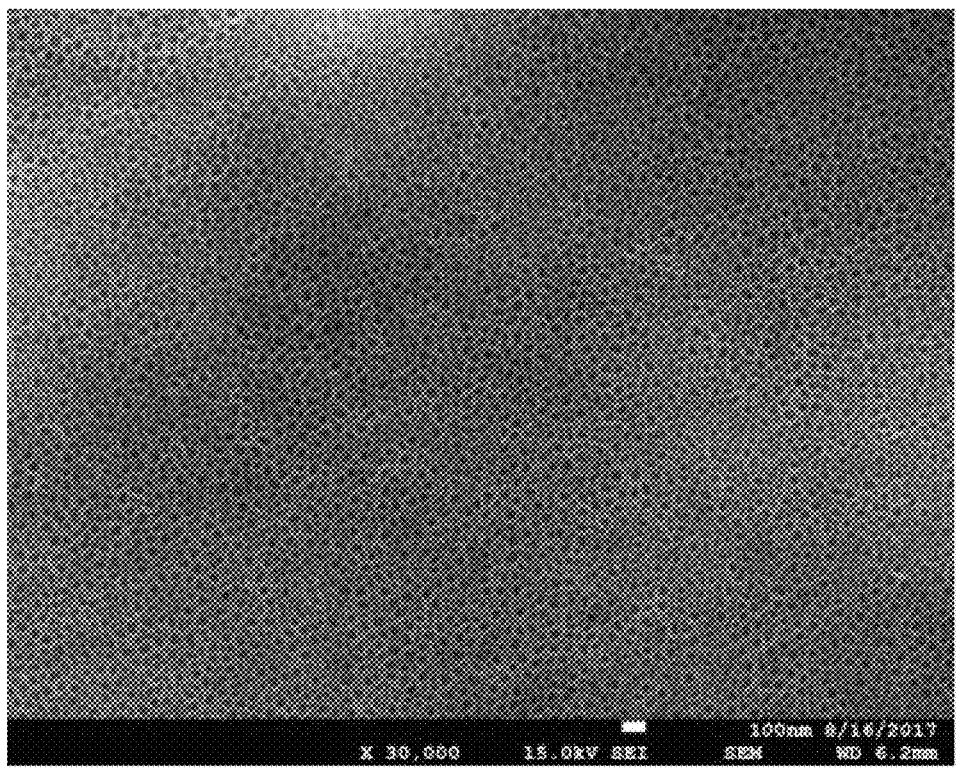
FIGS. 25A-B show representative SEM images of a metal oxide surface resulting from the method described in Example 6.
Figure 25B:
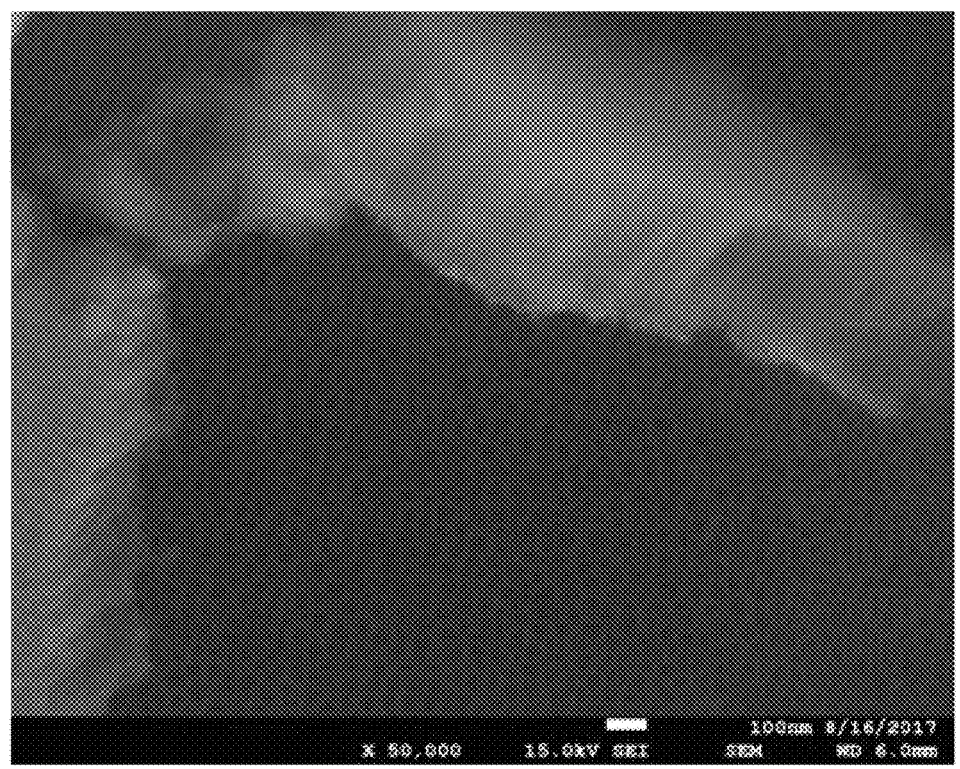

After the etching step, the foil was rinsed in deionized water and allowed to air dry. Then, using the same anodization conditions used in the first step, the foil was again anodized for 5 additional minutes at 25V. The foil was then imaged using SEM. Representative SEM images are shown in FIGS. 25A-B.

Example 7. Forming Metal Oxide Nanostructures on a Nickel Titanium Foil in the Presence of a Surface-Active Species An electrolyte solution was prepared containing 0.8 vol % deionized water ($H_2O$) (e.g., 0.8 ml), 0.20 wt % ammonium fluoride ($NH_4F$) (e.g., 0.2 g) (Sigma Aldrich), and 99.2 vol % ethylene glycol (e.g., 99.2 ml) (Sigma Aldrich). The electrolyte solution was brought to and maintained at 30° C.

50 mm×50 mm×0.127 mm (W×H×D) nitinol foil (Alfa Aesar, Inc.) was cut into 6 mm×6 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g., 6 mm×6 mm).

Figure 39:
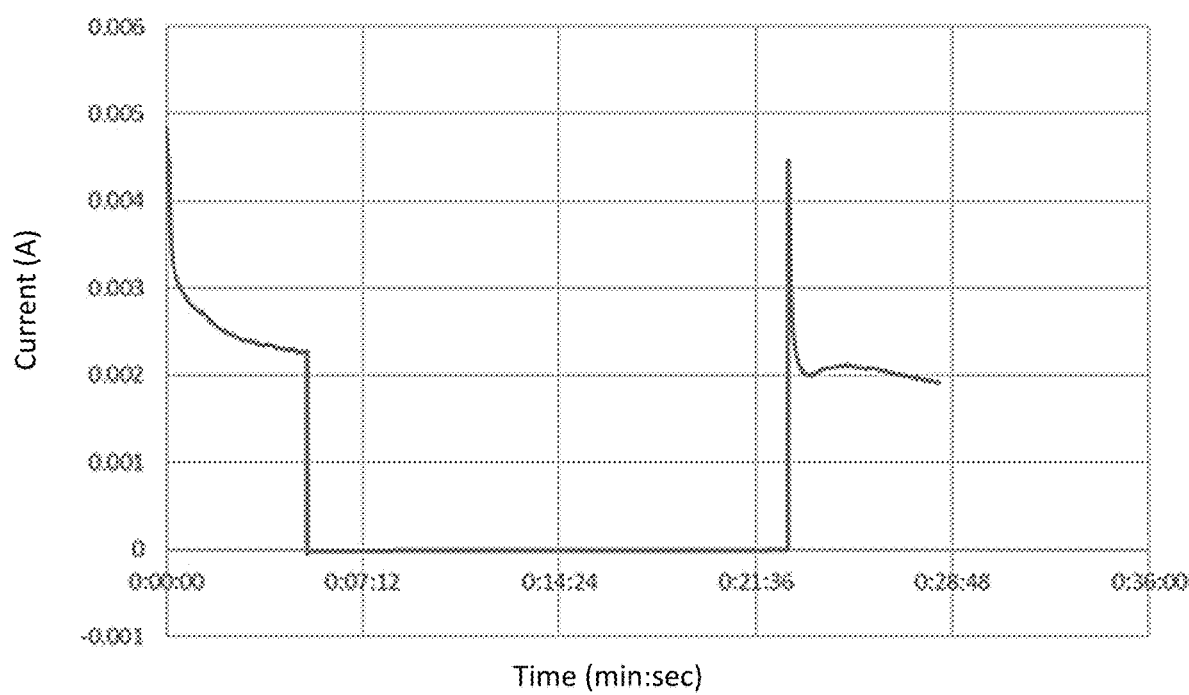
FIG. 39 shows a representative current profile resulting from performing the method described in Example 7.

A power supply (Agilent Technologies) provided a voltage of 25V between the anode (nitinol coupon) and platinum cathode for 5 minutes. The power supply was disconnected, and 1.4 mmol of 90% lactic acid (0.116 ml, Sigma-Aldrich) and 5.0 g of 1,2 octanediol (Sigma-Aldrich) were added. The electrolyte was stirred at 300 rpm with a magnetic stir bar. The anodization was subsequently continued for 5 minutes. During this time, the current was variable as monitored by a digital multimeter (Agilent Technologies) connected to a desktop computer running BenchVue 3.1 (Keysight Technologies). A representative current profile is shown in FIG. 39.

Figure 26A:
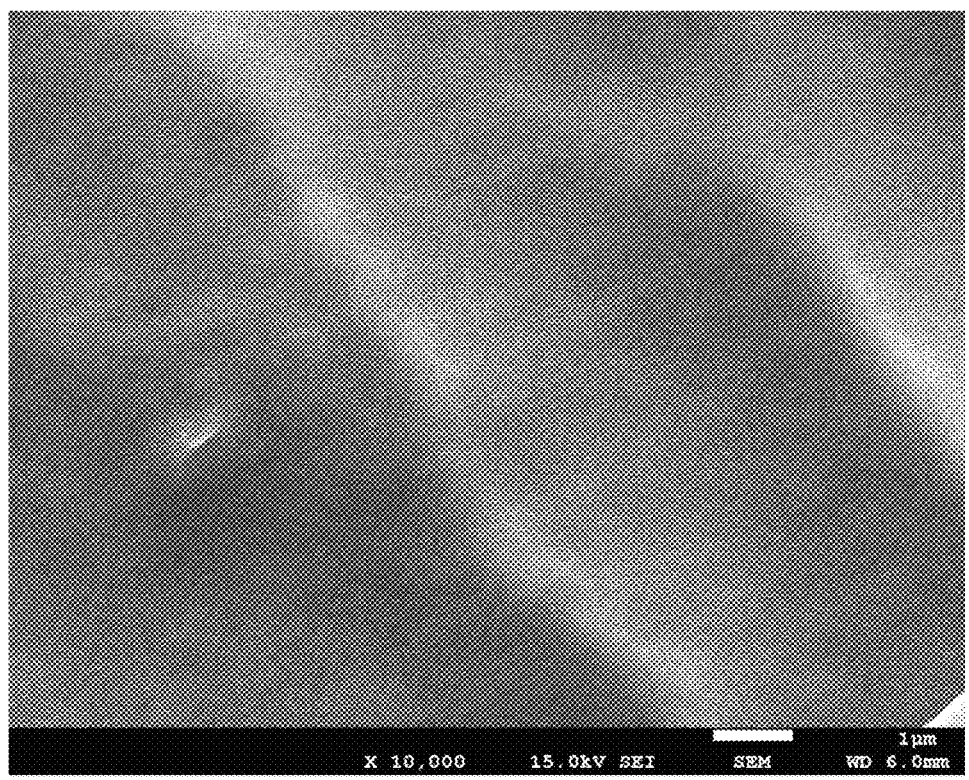
FIGS. 26A-C show representative SEM images of a metal oxide surface resulting from the method described in Example 7.
Figure 26B:
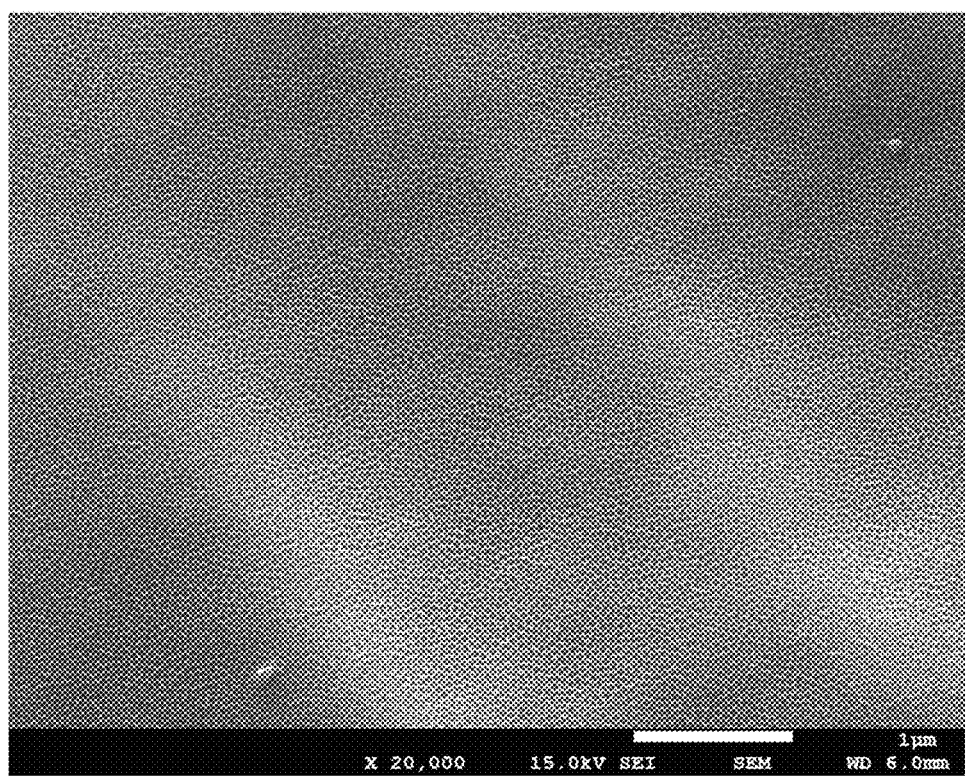
Figure 26C:
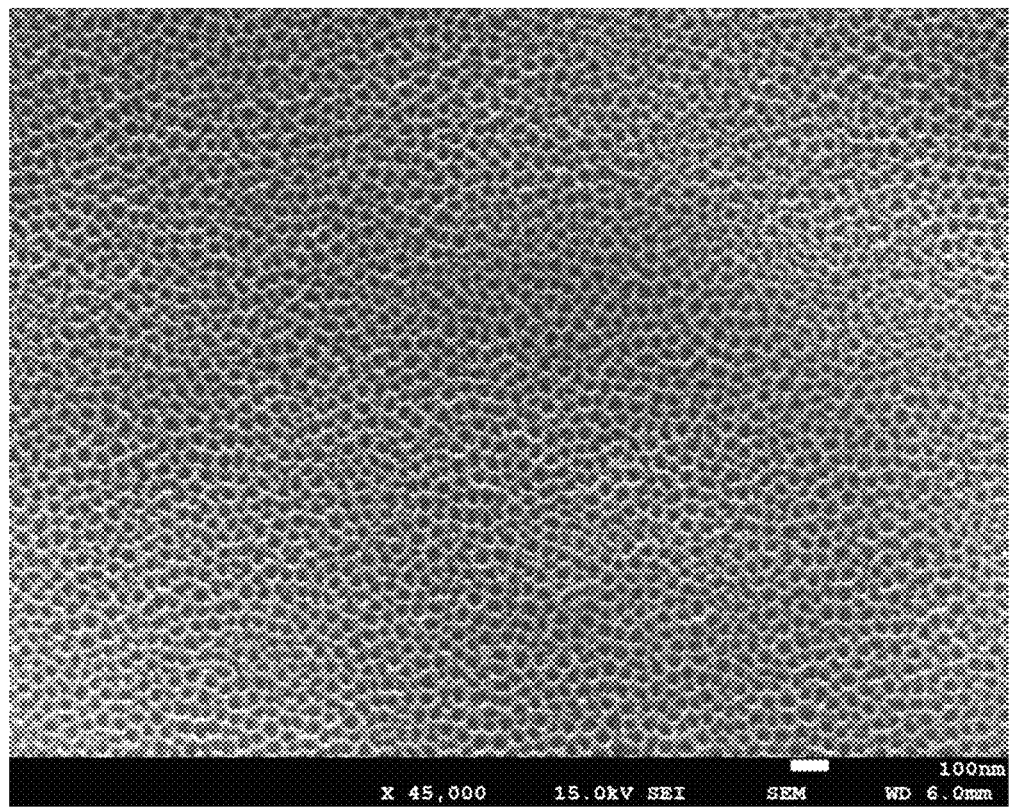

After the 5+5 minute run, the coupons were rinsed in deionized water and kept in 70% ethanol until further use or evaluation. Some of the coupons were then sonicated sequentially in acetone, ethanol, and water for 5 minutes each. Substantially no delamination or cracking (e.g., 5% or less) was observed on the coupons. Substantially clean and uniform surfaces were obtained. Some of the coupons were imaged using SEM. Representative SEM images are shown in FIGS. 26A-C.

Example 8. Forming Metal Oxide Nanostructures on a Nickel Titanium Stent at Low Voltages and Short Times An electrolyte solution was prepared containing 0.2 vol % deionized water ($H_2O$) (e.g., 0.2 ml), 0.05 wt % ammonium fluoride ($NH_4F$) (e.g., 0.05 g) (Sigma Aldrich), and 99.8 vol % ethylene glycol (e.g., 99.8 ml) (Sigma Aldrich). The electrolyte solution was brought to and maintained at 22° C.

A 40 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 $mm^2$.

Figure 40:
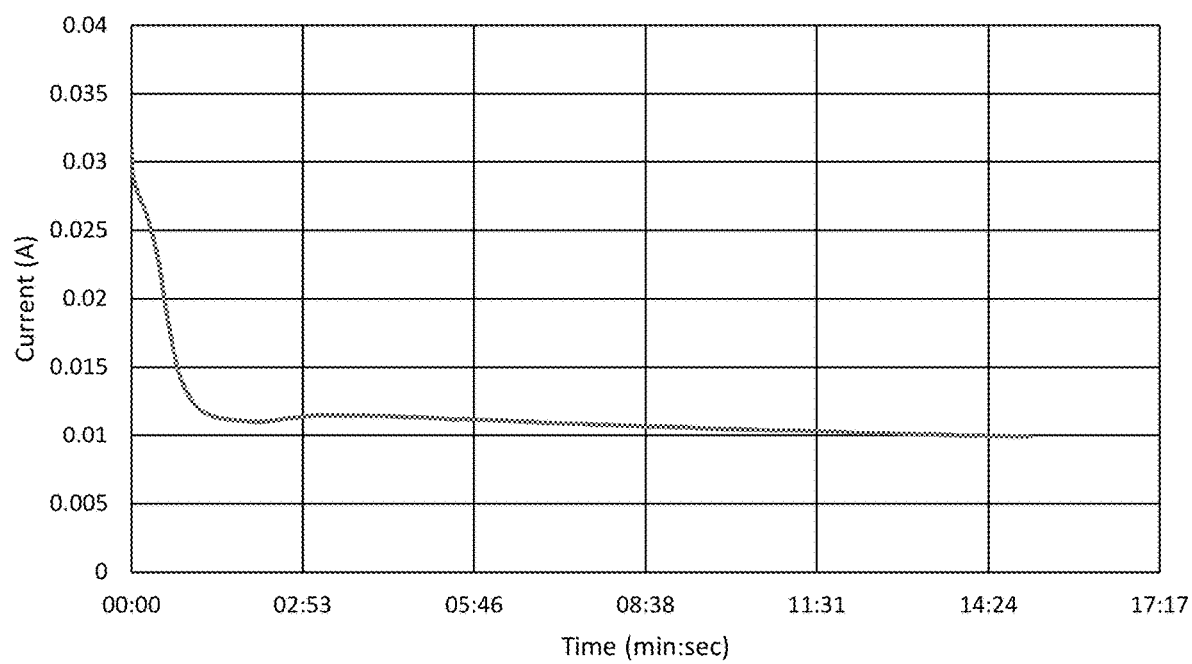
FIG. 40 shows a representative current profile resulting from performing the method described in Example 8.

A power supply (Agilent Technologies) provided a constant voltage of 25V between the anode (nitinol stent) and platinum cathodes for 15 minutes. During this time, the current was variable as monitored by a digital multimeter (Agilent Technologies) connected to a desktop computer running BenchVue 3.1 (Keysight Technologies). A representative current profile is shown in FIG. 40.

Figure 27A:
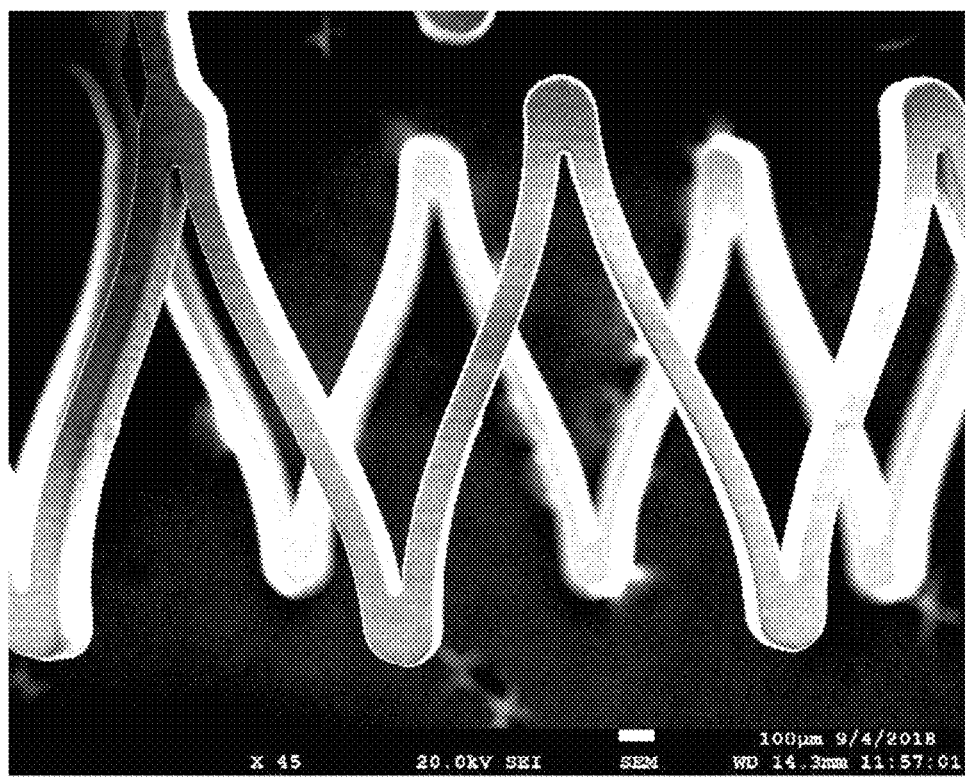
FIGS. 27A-B show representative SEM images of a metal oxide surface resulting from the method described in Example 8.
Figure 27B:
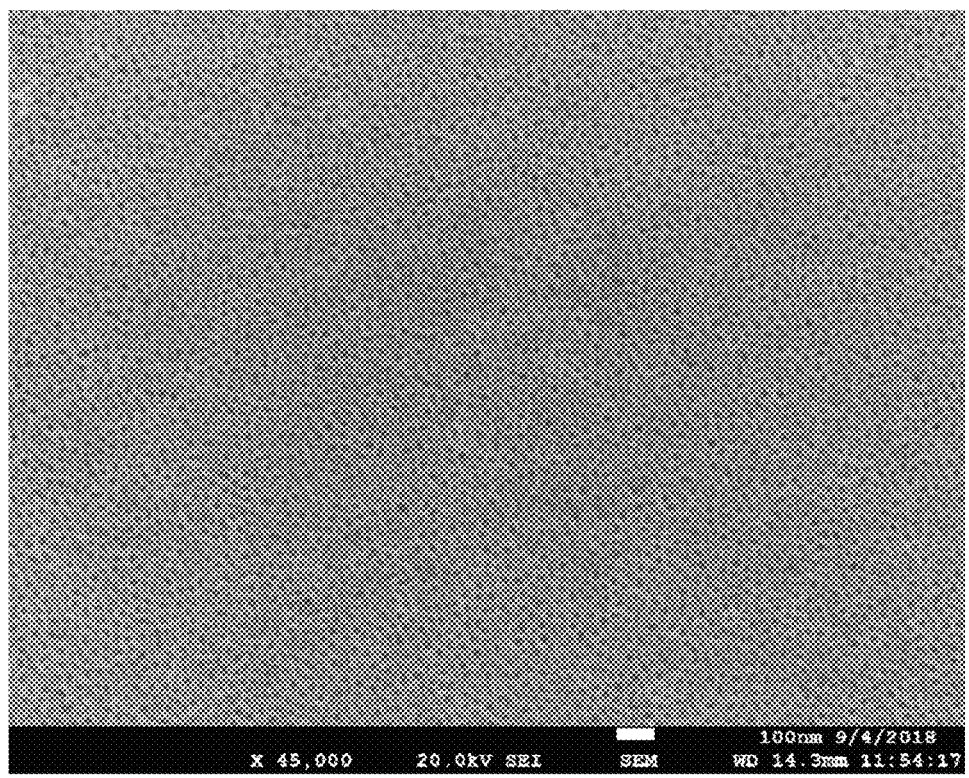

After the 15-minute run, the stent was rinsed in deionized water and kept in 70% ethanol until further use or evaluation. The stent was then imaged using SEM. Representative SEM images of the resulting metal oxide nanostructures are shown in FIGS. 27A-B.

Example 9. Forming Metal Oxide Nanostructures on a Nickel Titanium Stent at Low Voltages and Discrete Short Times An electrolyte solution was prepared containing 0.8 vol % deionized water ($H_2O$) (e.g., 0.8 ml), 0.20 wt % ammonium fluoride ($NH_4F$) (e.g., 0.20 g) (Sigma Aldrich), and 99.2 vol % ethylene glycol (e.g., 99.2 ml) (Sigma Aldrich). The electrolyte solution was brought to and maintained at 22° C.

A 40 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 $mm^2$.

Figure 41:
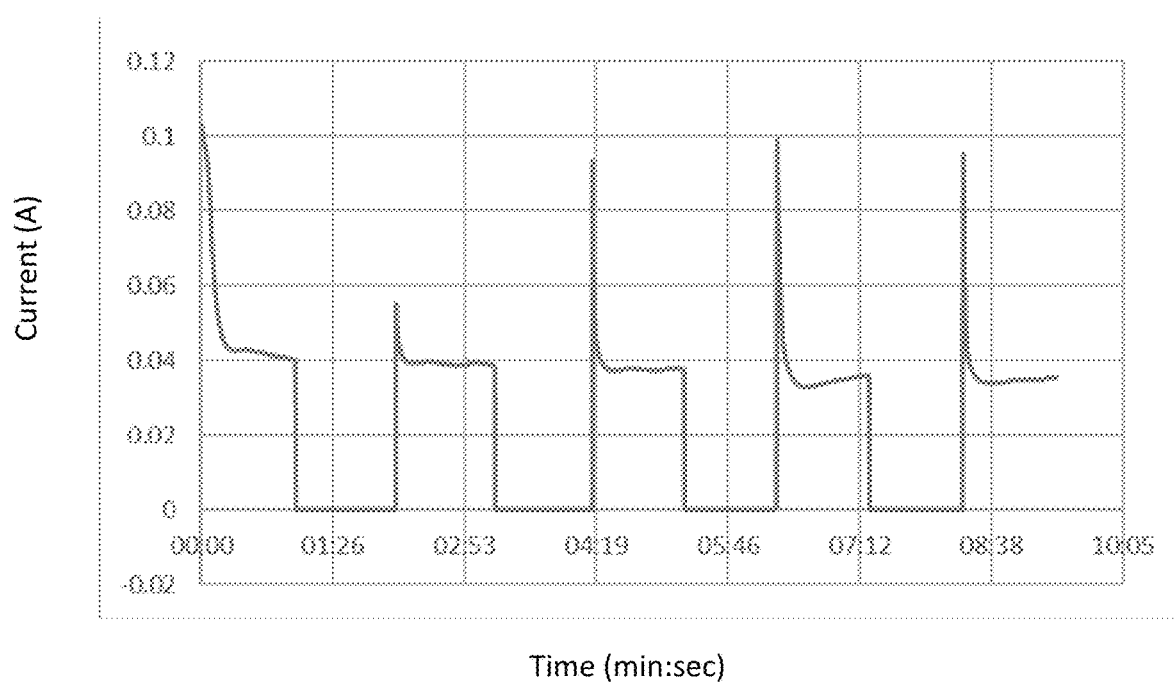
FIG. 41 shows a representative current profile resulting from performing the method described in Example 9.

A power supply (Agilent Technologies) provided a voltage of 25V between the anode (nitinol stent) and platinum cathodes for 5 discrete 1-minute time periods, with a 1-minute dwell time at 0V in between each 1-minute time period of 25V. During this time, the current was variable as monitored by a digital multimeter (Agilent Technologies) connected to a desktop computer running BenchVue 3.1 (Keysight Technologies). A representative current profile is shown in FIG. 41.

Figure 28A:
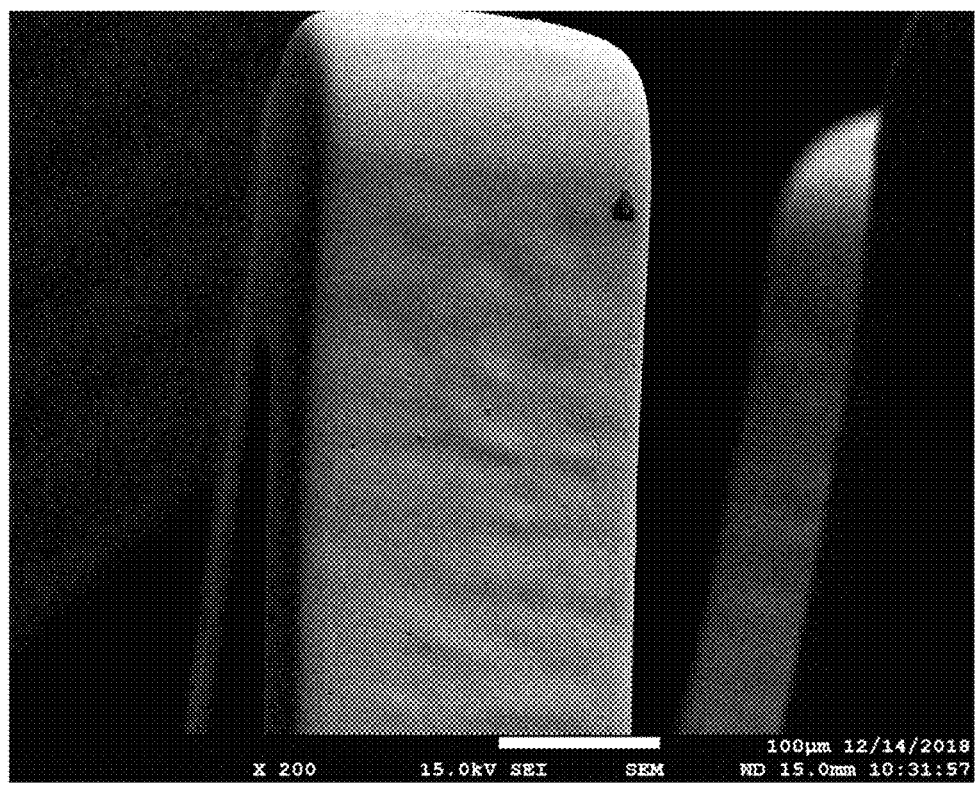
FIGS. 28A-B show representative SEM images of a metal oxide surface resulting from the method described in Example 9.
Figure 28B:
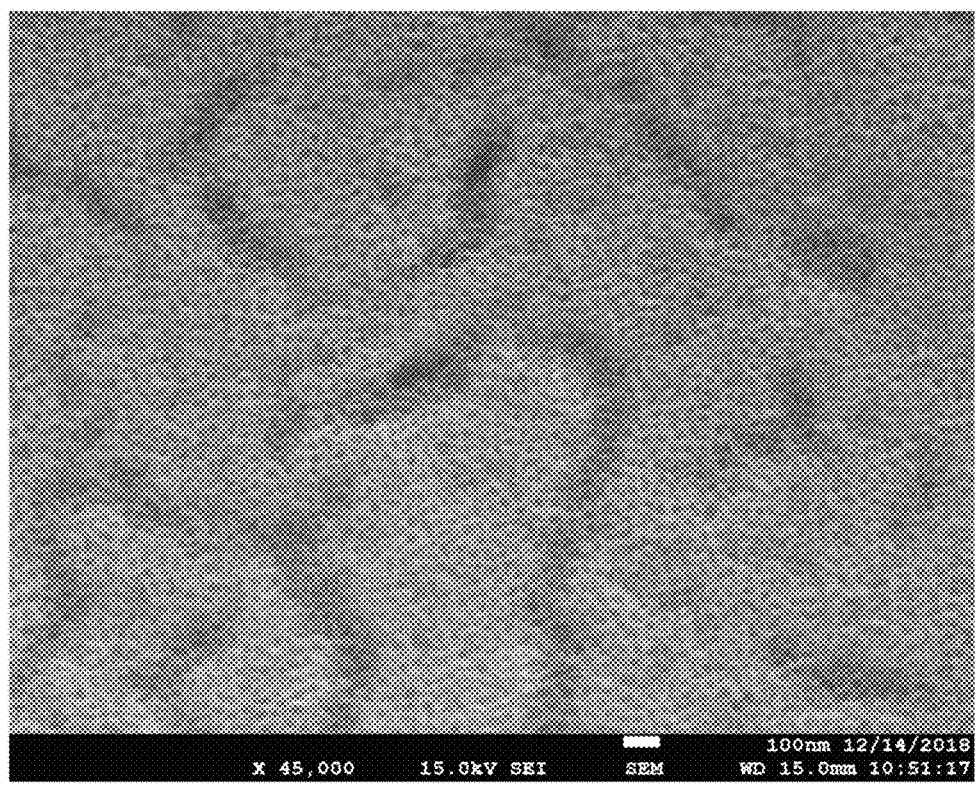

After the anodization, the stent was rinsed in deionized water and kept in 70% ethanol until further use or evaluation. The stent was then imaged using SEM. Representative SEM images of the resulting metal oxide nanostructures are shown in FIGS. 28A-B.

Example 10. Forming Metal Oxide Nanostructures on a Nickel Titanium Stent at Low Voltages and Discrete Short Times Followed by a Lower Voltage Step An electrolyte solution was prepared containing 0.8 vol % deionized water ($H_2O$) (e.g., 0.8 ml), 0.20 wt % ammonium fluoride ($NH_4F$) (e.g., 0.20 g) (Sigma Aldrich), and 99.2 vol % ethylene glycol (e.g., 99.2 ml) (Sigma Aldrich). The electrolyte solution was brought to and maintained at 22° C.

A 60 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 $mm^2$.

Figure 42:
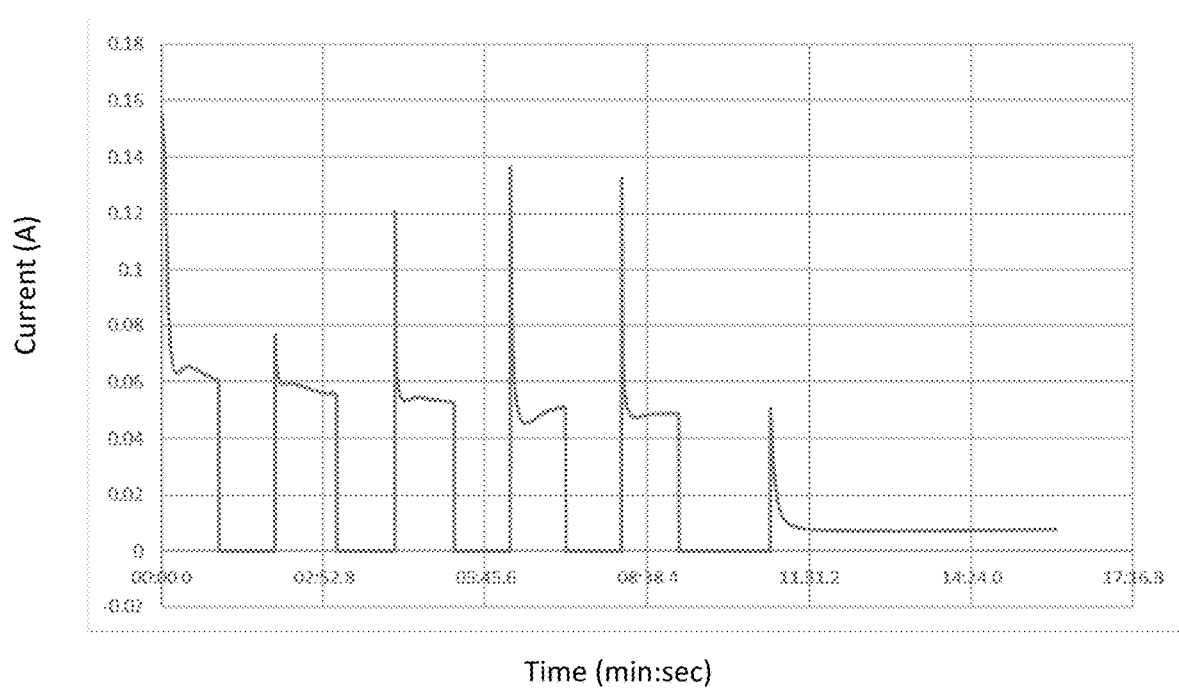
FIG. 42 shows a representative current profile resulting from performing the method described in Example 10.

A power supply (Agilent Technologies) provided a voltage of 25V between the anode (nitinol stent) and platinum for 5 discrete 1-minute time periods, with a 1-minute dwell time at 0V after each 1-minute time period of 25V. This was followed by a 5 minute anodization at 10V. During this time, the current was variable as monitored by a digital multimeter (Agilent Technologies) connected to a desktop computer running BenchVue 3.1 (Keysight Technologies). A representative current profile is shown in FIG. 42.

Figure 29A:
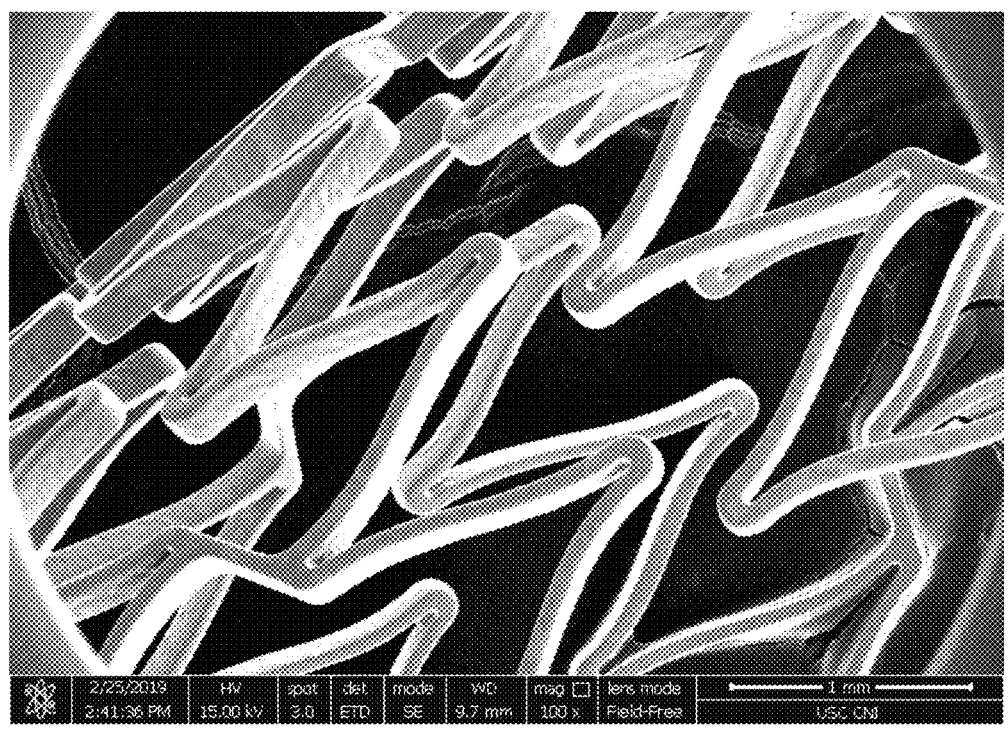
FIGS. 29A-B show representative SEM images of a metal oxide surface resulting from the method described in Example 10.
Figure 29B:
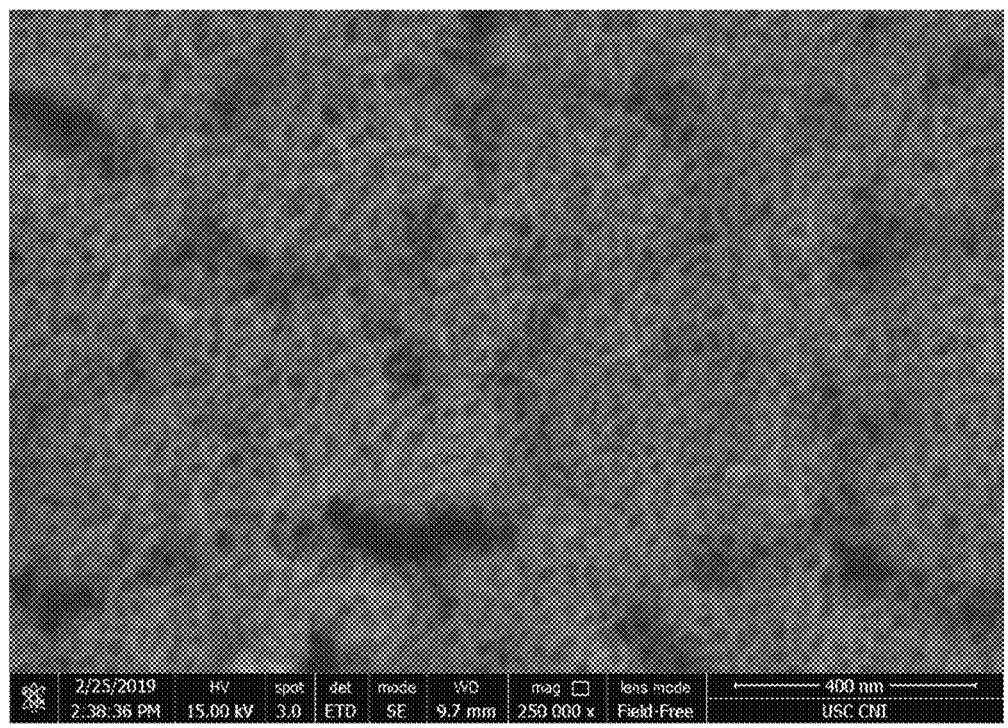

After the anodization, the stent was rinsed in deionized water and kept in 70% ethanol until further use or evaluation. The stent was then imaged using SEM. Representative SEM images of the resulting metal oxide nanostructures are shown in FIGS. 29A-B.

Example 11. Forming Metal Oxide Nanostructures on a Nickel Titanium Stent at Low Voltages and Discrete Short Times Followed by a Lower Voltage Step in a Substantially Fluoride-Free Electrolyte An electrolyte solution was prepared containing 0.8 vol % deionized water ($H_2O$) (e.g., 0.8 ml), 0.20 wt % ammonium fluoride ($NH_4F$) (e.g., 0.20 g) (Sigma Aldrich), and 99.2 vol % ethylene glycol (e.g., 99.2 ml) (Sigma Aldrich). The electrolyte solution was brought to and maintained at 22° C.

A 40 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 $mm^2$.

Figure 43:
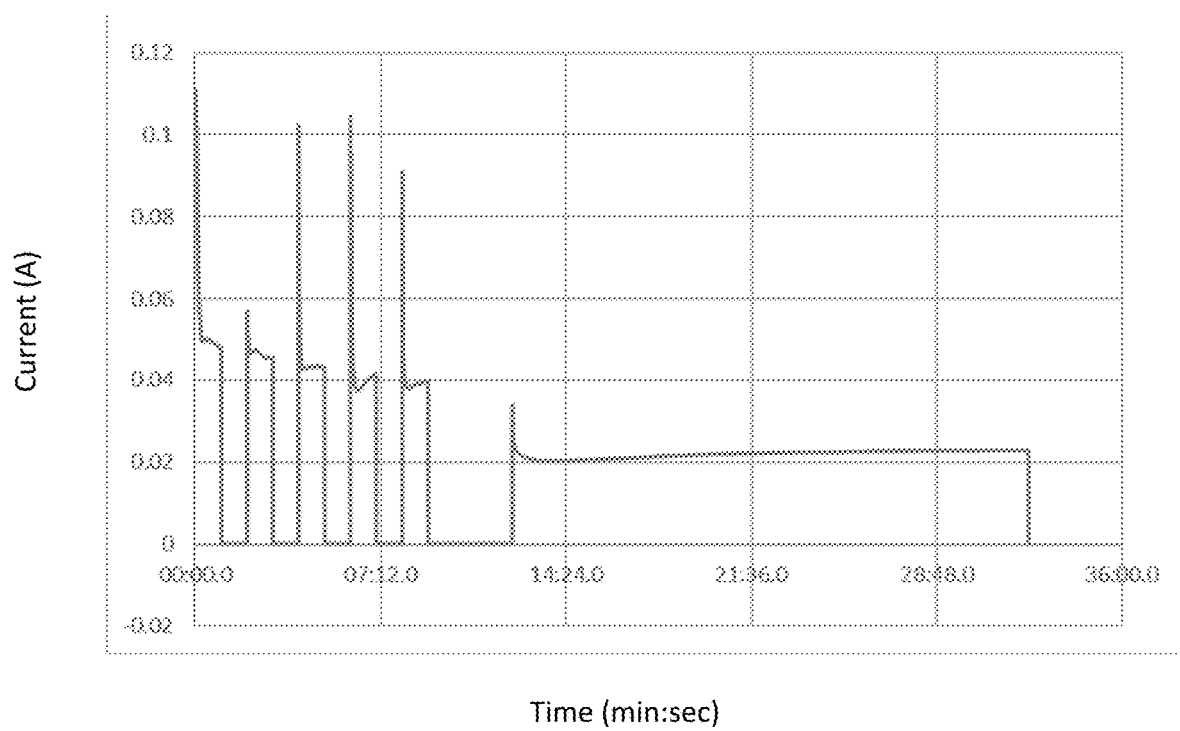
FIG. 43 shows a representative current profile resulting from performing the method described in Example 11.

A power supply (Agilent Technologies) provided a voltage of 25V between the anode (nitinol stent) and platinum cathodes for 5 discrete 1-minute time periods, with a 1-minute dwell time at 0V in between each 1-minute time period of 25V. The anodization was stopped, and the electrolyte was replaced with an electrolyte containing 0.8 vol % deionized water ($H_2O$) (e.g., 0.8 ml), 1.10 wt % lithium lactate (e.g., 1.10 g) (Sigma Aldrich), and 99.2 vol % ethylene glycol (e.g., 99.2 ml) (Sigma Aldrich). The electrolyte solution was brought to and maintained at 22° C. The anodization was then continued for 20 minutes at a voltage of 10V. During this time, the current was variable as monitored by a digital multimeter (Agilent Technologies) connected to a desktop computer running BenchVue 3.1 (Keysight Technologies). A representative current profile is shown in FIG. 43.

Figure 30A:
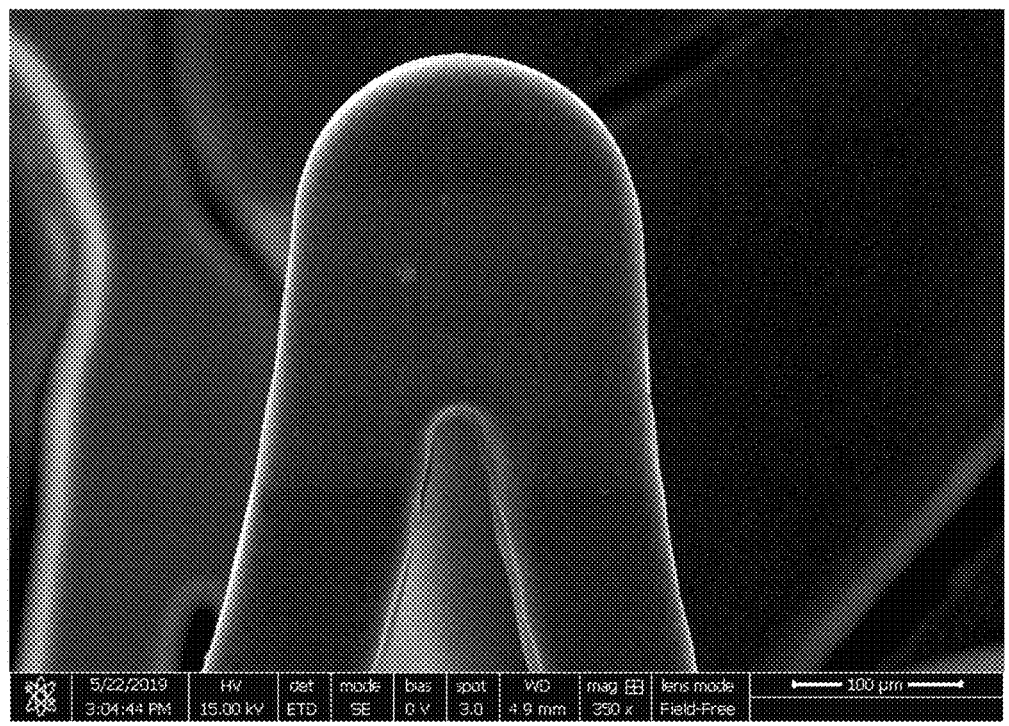
FIGS. 30A-B show representative SEM images of a metal oxide surface resulting from the method described in Example 11.
Figure 30B:
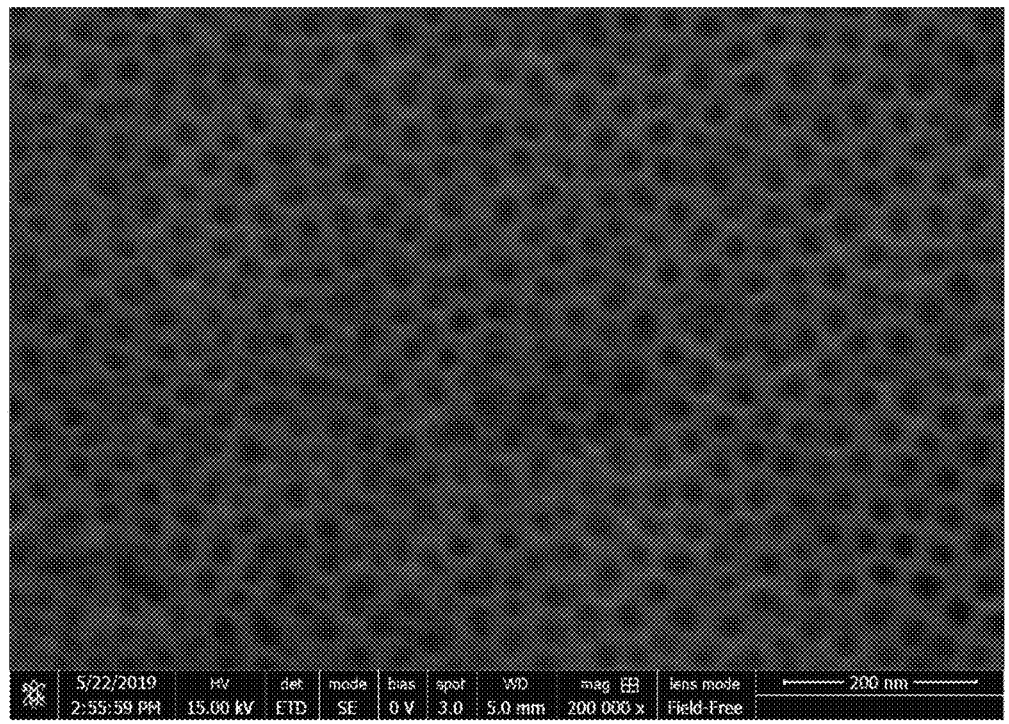

After the anodization, the stent was rinsed in deionized water and kept in 70% ethanol until further use or evaluation. The stent was then imaged using SEM. Representative SEM images of the resulting metal oxide nanostructures are shown in FIGS. 30A-B.

Example 12. Forming Metal Oxide Nanostructures on a Nickel Titanium Stent at Low Voltages and Discrete Short Times Followed by a Lower Voltage Step in a Substantially Fluoride-Free Electrolyte An electrolyte solution was prepared containing 0.8 vol % deionized water ($H_2O$) (e.g., 0.8 ml), 0.20 wt % ammonium fluoride ($NH_4F$) (e.g., 0.20 g) (Sigma Aldrich), and 99.2 vol % ethylene glycol (e.g., 99.2 ml) (Sigma Aldrich). The electrolyte solution was brought to and maintained at 22° C.

A 40 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the θembodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 mm$^2$.

Figure 44:
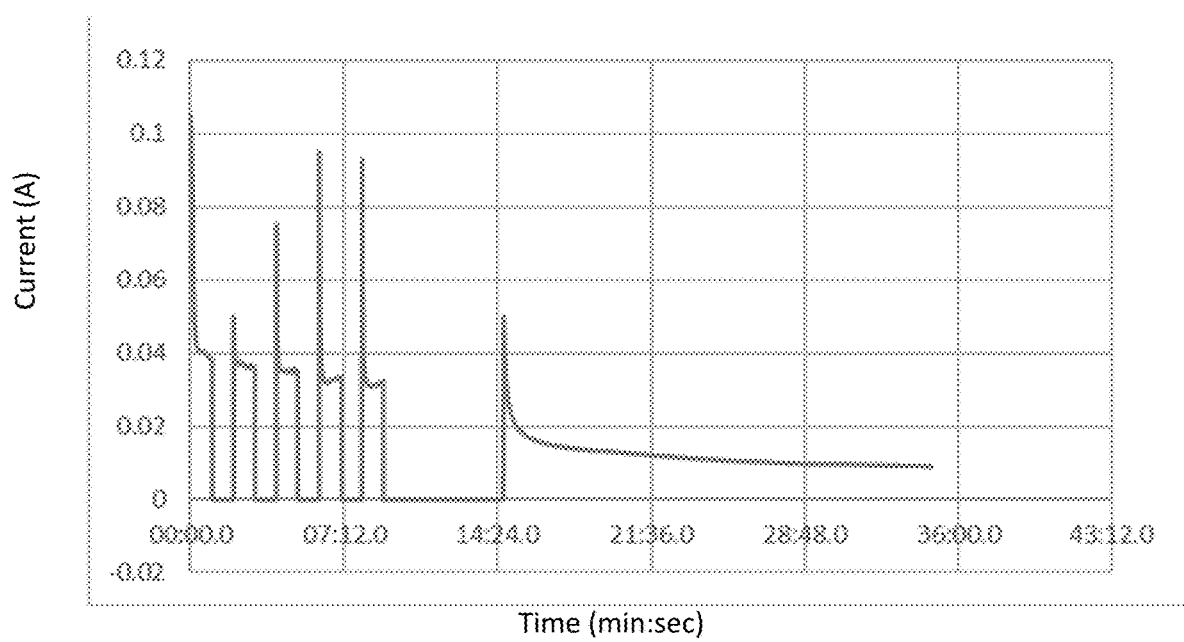
FIG. 44 shows a representative current profile resulting from performing the method described in Example 12.

A power supply (Agilent Technologies) provided a voltage of 25V between the anode (nitinol stent) and platinum cathodes for 5 discrete 1-minute time periods, with a 1-minute dwell time at 0V in between each 1-minute time period of 25V. The anodization was stopped, and the electrolyte was replaced with an electrolyte containing 0.8 vol % deionized water ($H_2O$) (e.g., 0.8 ml), 1.74 wt % dipotassium hydrogen phosphate (e.g., 1.74 g) (Sigma Aldrich), and 99.2 vol % ethylene glycol (e.g., 99.2 ml) (Sigma Aldrich). The electrolyte solution was brought to and maintained at 22° C. The anodization was then continued for 20 minutes at a voltage of 10V. During this time, the current was variable as monitored by a digital multimeter (Agilent Technologies) connected to a desktop computer running BenchVue 3.1 (Keysight Technologies). A representative current profile is shown in FIG. 44.

Figure 31A:
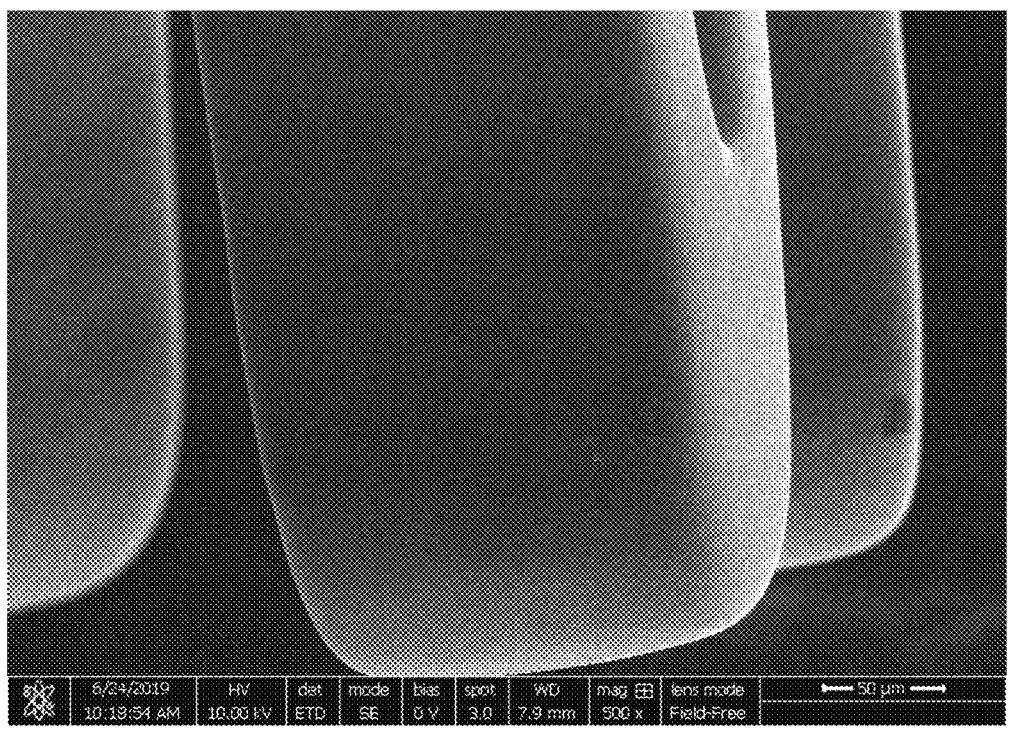
FIGS. 31A-B show representative SEM images of a metal oxide surface resulting from the method described in Example 12.
Figure 31B:
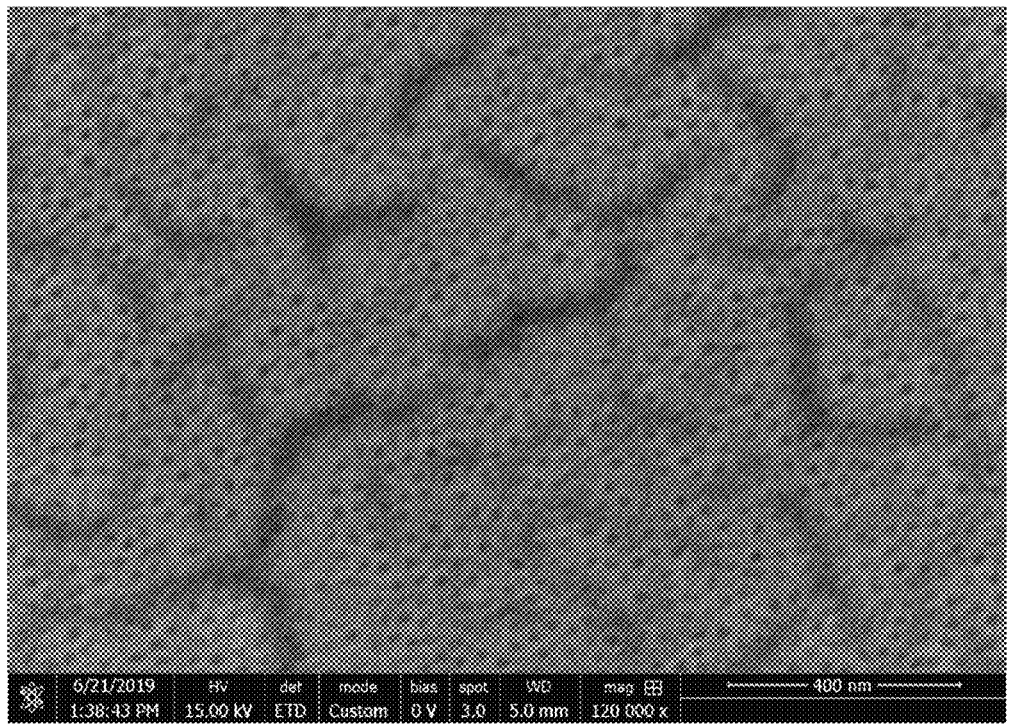

After the anodization, the stent was rinsed in deionized water and kept in 70% ethanol until further use or evaluation. The stent was then imaged using SEM. Representative SEM images of the resulting metal oxide nanostructures are shown in FIGS. 31A-B.

Example 13. Forming Metal Oxide Nanostructures on a Nickel Titanium Stent at Low Voltages and Discrete Short Times An electrolyte solution was prepared containing 0.8 vol % deionized water ($H_2O$) (e.g., 0.8 ml), 0.20 wt % ammonium fluoride ($NH_4F$) (e.g., 0.20 g) (Sigma Aldrich), and 99.2 vol % ethylene glycol (e.g., 99.2 ml) (Sigma Aldrich). The electrolyte solution was brought to and maintained at 22° C.

A 60 mm×7 mm (length×diameter) nitinol stent (Relucent, Inc.) was ultrasonically cleaned with acetone, ethanol, and deionized water for 5 minutes each. It was then kept in 70% ethanol until further use. Prior to anodization, the stent was rinsed in deionized water and air dried.

For anodization, the stent was secured in an apparatus similar to the embodiment shown in FIG. 14. The center of the secured nitinol stent was positioned approximately 2 cm from the platinum cathodes (Sigma Aldrich). The area of the 5 exposed platinum cathodes was 5×5 mm×40 mm=1000 mm$^2$.

Figure 45:
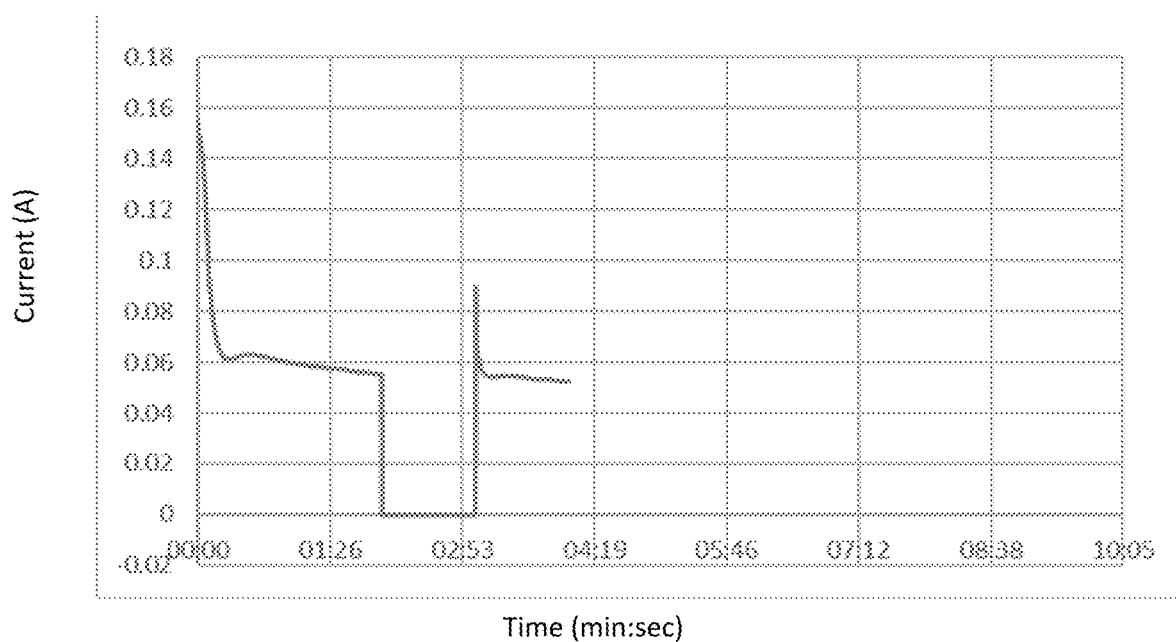
FIG. 45 shows a representative current profile resulting from performing the method described in Example 13.

A power supply (Agilent Technologies) provided a voltage of 25V between the anode (nitinol stent) and platinum cathodes for 2 minutes, followed by a 1-minute dwell time at 0V, followed by a 1-minute period of 25V. During this time, the current was variable as monitored by a digital multimeter (Agilent Technologies) connected to a desktop computer running BenchVue 3.1 (Keysight Technologies). A representative current profile is shown in FIG. 45.

Figure 32A:
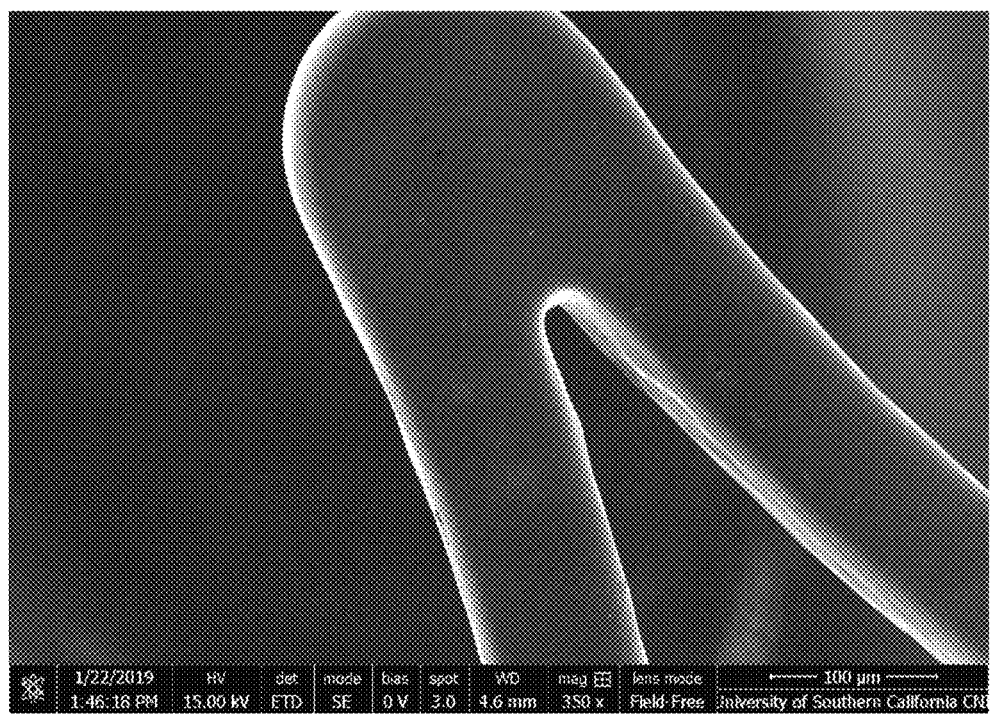
FIGS. 32A-B show representative SEM images of a metal oxide surface resulting from the method described in Example 13.
Figure 32B:
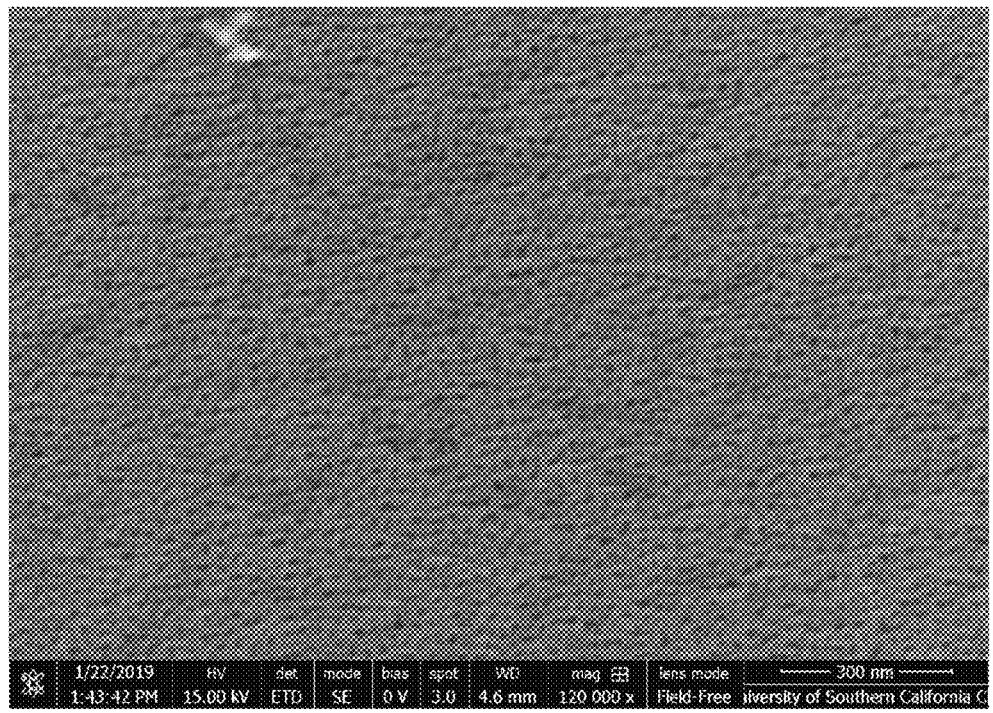

After the anodization, the stent was rinsed in deionized water and kept in 70% ethanol until further use or evaluation. The stent was then imaged using SEM. Representative SEM images of the resulting metal oxide nanostructures are shown in FIGS. 32A-B.

Additional Embodiments

In some embodiments, a method of preparing a biocompatible surface is provided, the method comprising placing an anode and one or more cathodes in electrical contact through a first electrolyte solution, and applying a voltage across the anode and cathode (s) through the first electrolyte solution for a first time period.

Some embodiments include the method of preparing a biocompatible surface of any one or more preceding embodiments, wherein the first electrolyte solution includes an organic solvent, a fluoride-bearing species, and water.

Some embodiments include the method of preparing a biocompatible surface of any one or more preceding embodiments, further comprising providing an anode and one or more cathodes.

Some embodiments include the method of preparing a biocompatible surface of any one or more preceding embodiments, wherein at least two cathodes are placed into electrical contact with the anode through the first electrolyte solution.

Some embodiments include the method of preparing a biocompatible surface of any one or more preceding embodiments, wherein the first time period is between about 1 minute and about 30 minutes.

Some embodiments include the method of preparing a biocompatible surface of any one or more preceding embodiments, wherein the first time period is between about 2 minutes and about 25 minutes.

Some embodiments include the method of preparing a biocompatible surface of any one or more preceding embodiments, wherein the anode comprises an alloy of nickel and titanium.

Some embodiments include the method of preparing a biocompatible surface of any one or more preceding embodiments, wherein the anode is a stent.

Some embodiments include the method of preparing a biocompatible surface of any one or more preceding embodiments, further comprising providing at least one guard electrode.

Some embodiments include the method of preparing a biocompatible surface of any one or more preceding embodiments, wherein the anode comprises a substrate and a guard electrode.

Some embodiments include the method of preparing a biocompatible surface of any one or more preceding embodiments, wherein the guard electrode is positioned near the substrate such that an electric field generated when the first voltage is applied during the first time period is modified by the presence of the guard electrode.

Some embodiments include the method of preparing a biocompatible surface of any one or more preceding embodiments, wherein the voltage applied across the substrate and the at least one cathode is controlled independently of the voltage applied across the guard electrode and the at least one cathode.

Some embodiments include the method of preparing a biocompatible surface of any one or more preceding embodiments, further comprising at least a second cathode.

Some embodiments include the method of preparing a biocompatible surface of any one or more preceding embodiments, wherein the voltages applied across the anode and each of the at least two cathodes can be controlled independently of one another.

Some embodiments include the method of preparing a biocompatible surface of any one or more preceding embodiments, wherein the voltage applied across the anode and at least one cathode is a waveform (e.g., variable) voltage.

Some embodiments include the method of preparing a biocompatible surface of any one or more preceding embodiments, wherein the waveform voltage comprises a voltage modulating between a positive voltage and zero voltage.

Some embodiments include the method of preparing a biocompatible surface of any one or more preceding embodiments, wherein the waveform voltage comprises a voltage modulating between a positive voltage, followed by zero voltage, and followed by a negative voltage.

Some embodiments include the method of preparing a biocompatible surface of any one or more preceding embodiments, wherein the waveform voltage comprises a voltage modulating between a positive voltage, followed by zero voltage, followed by a negative voltage, followed by zero voltage.

Some embodiments include the method of preparing a biocompatible surface of any one or more preceding embodiments, wherein the first electrolyte solution further comprises a surface-active species.

Some embodiments include the method of preparing a biocompatible surface of any one or more preceding embodiments, wherein the surface-active species is TERGITOL© series, triton X-100, DOWFAXES, pluronics, or an alkyl vicinal diol.

Some embodiments include the method of preparing a biocompatible surface of any one or more preceding embodiments, wherein a first metal oxide nanostructure is formed during the first time period.

Some embodiments include the method of preparing a biocompatible surface of any one or more preceding embodiments, further comprising removing the first metal oxide nanostructure.

Some embodiments include the method of preparing a biocompatible surface of any one or more preceding embodiments, further comprising applying a second voltage across the anode and cathode through a second electrolyte solution for a second time period.

Some embodiments include the method of preparing a biocompatible surface of any one or more preceding embodiments, wherein a second metal oxide nanostructure is formed during the second time period.

Some embodiments include the method of preparing a biocompatible surface of any one or more preceding embodiments, wherein removing the first metal oxide nanostructure comprises exposing the anode with the first metal oxide nanostructure to ultrasonic energy.

Some embodiments include the method of preparing a biocompatible surface of any one or more preceding embodiments, wherein removing the first metal oxide nanostructure comprises mechanically removing the first metal oxide nanostructure.

Some embodiments include the method of preparing a biocompatible surface of any one or more preceding embodiments, wherein removing the first metal oxide nanostructure comprises soaking the anode with the first metal oxide nanostructure in a chemical etchant.

Some embodiments include the method of preparing a biocompatible surface of any one or more preceding embodiments, wherein the anode is soaking in a solvent after removing of the first metal oxide nanostructure and prior to applying a second voltage across the anode and the at least one cathode.

Some embodiments include the method of preparing a biocompatible surface of any one or more preceding embodiments, wherein the position of the anode changes relative to the position of the cathode(s) during the first time period.

Some embodiments include the method of preparing a biocompatible surface of any one or more preceding embodiments, wherein the anode is moved relative to the cathode(s).

Some embodiments include the method of preparing a biocompatible surface of any one or more preceding embodiments, wherein the anode is rotated relative to the cathode(s).

Some embodiments include the method of preparing a biocompatible surface of any one or more preceding embodiments, wherein the cathode(s) are moved relative to the anode.

In some embodiments, an apparatus comprising at least one cathode is provided, wherein the apparatus is configured to hold an anode, and wherein the anode and at least one cathode are configured to be placed into electrical contact with one another through an electrolyte solution.

Some embodiments include the apparatus of any one or more preceding embodiments, further comprising at least one guard electrode.

Some embodiments include the apparatus of any one or more preceding embodiments, wherein the at least one guard electrode is in direct physical contact with the anode.

Some embodiments include the apparatus of any one or more preceding embodiments, wherein the at least one guard electrode is not in direct physical contact with the anode.

Some embodiments include the apparatus of any one or more preceding embodiments, wherein the at least one guard electrode is configured to modify the electric field created around the anode when a voltage is applied across the cathode and the anode.

Some embodiments include the apparatus of any one or more preceding embodiments, further comprising at least a second cathode.

Some embodiments include the apparatus of any one or more preceding embodiments, wherein each of the plurality of cathodes can be independently controlled such that a different voltage can be applied across each of the plurality of cathodes and the anode.

Some embodiments include the apparatus of any one or more preceding embodiments, wherein the at least one guard electrode is in direct physical contact with the anode.

Some embodiments include the apparatus of any one or more preceding embodiments, wherein the at least one guard electrode is not in direct physical contact with the anode.

Some embodiments include the apparatus of any one or more preceding embodiments, wherein the at least one guard electrode is configured to modify the electric field created around the anode when a voltage is applied across at least one of the plurality of cathodes and the anode.

Some embodiments include the apparatus of any one or more preceding embodiments, wherein the apparatus is configured such that the anode can change relative to the position of the cathode(s) during the first time period.

Some embodiments include the apparatus of any one or more preceding embodiments, wherein the anode is moved relative to the cathode(s).

Some embodiments include the apparatus of any one or more preceding embodiments, wherein the anode is rotated relative to the cathode(s).

Some embodiments include the apparatus of any one or more preceding embodiments, wherein the cathode(s) are moved relative to the anode.

Any combination of methods, devices, systems, and features disclosed above are within the scope of this disclosure.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

While certain embodiments of the invention have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed may be:

1. A method of preparing a biocompatible surface on a nitinol substrate, comprising:
   providing an anode and a cathode in a first electrolyte solution;
   applying a waveform voltage across the anode and the cathode through the first electrolyte solution for a first time period, thereby forming a first metal oxide nanostructure;
   removing the first metal oxide nanostructure after the first metal oxide nanostructure is formed;
   modifying the first electrolyte solution or replacing the first electrolyte solution with a second electrolyte solution after the first metal oxide nanostructure is formed; and
   applying a second voltage across the anode and the cathode through the second electrolyte solution for a second time period,
   wherein:
   the first electrolyte solution comprises an organic solvent, a fluoride-bearing species, and water, and
   the anode comprises the nitinol substrate.

2. The method of claim 1, wherein the waveform voltage modulates between a positive voltage and zero voltage.

3. The method of claim 1, wherein the first time period is in a range of 15 seconds to 30 minutes.

4. The method of claim 1, wherein the anode further comprises at least one guard electrode.

5. The method of claim 1, wherein the anode further comprises at least one guard electrode, and wherein the at least one guard electrode is positioned near the substrate such that an electric field generated when the waveform voltage is applied is modified by the presence of the at least one guard electrode.

6. The method of claim 1, wherein the nitinol substrate is a stent.

7. The method of claim 1, wherein the method further comprises changing the position of the anode relative to the position of the cathode during the first time period.

8. The method of claim 1, wherein the method further comprises providing a plurality of cathodes in the electrolyte solution.

9. The method of claim 1, wherein the method further comprises providing a plurality of cathodes in the electrolyte solution; and
   wherein the method further comprises changing the position of the anode relative to the position of the plurality of cathodes during the first time period.

10. The method of claim 1, wherein the removing the first metal oxide nanostructure comprises exposing the anode with the first metal oxide nanostructure to ultrasonic energy, mechanically removing the first metal oxide nanostructure, soaking the anode with the first metal oxide nanostructure in a chemical etchant, or any combination thereof.

11. The method of claim 1, wherein the second voltage is a waveform voltage.

12. The method of claim 1, wherein the first time period is in a range of 15 seconds to 30 minutes.

13. The method of claim 1, wherein the anode further comprises at least one guard electrode.

* * * * *